US012331106B2

(12) United States Patent
Koh et al.

(10) Patent No.: US 12,331,106 B2
(45) Date of Patent: Jun. 17, 2025

(54) ANTI-ANGIOPOIETIN-2 ANTIBODIES THAT INDUCE TIE2 ACTIVATION

(71) Applicants: Institute for Basic Science, Daejeon (KR); Korea Advanced Institute of Science and Technology, Daejeon (KR)

(72) Inventors: Gou Young Koh, Daejeon (KR); Jeomil Bae, Daejeon (KR); Mi Jeong Kim, Daejeon (KR); Jin-Sung Park, Daejeon (KR); Su Jin Seo, Daejeon (KR); Jaeryung Kim, Daejeon (KR); Jang Ryul Park, Daejeon (KR); Pilhan Kim, Daejeon (KR); Wangyuhl Oh, Daejeon (KR)

(73) Assignees: Institute for Basic Science, Daejeon (KR); Korea Advanced Instritute of Science and Technology, Daejeon (KR)

( * ) Notice: Subject to any disclaimer, the term of this patent is extended or adjusted under 35 U.S.C. 154(b) by 0 days.

(21) Appl. No.: 18/045,964

(22) Filed: Oct. 12, 2022

(65) Prior Publication Data

US 2023/0272057 A1   Aug. 31, 2023

Related U.S. Application Data

(60) Division of application No. 16/995,707, filed on Aug. 17, 2020, now Pat. No. 11,498,962, which is a continuation of application No. PCT/KR2019/001983, filed on Feb. 19, 2019.

(60) Provisional application No. 62/633,038, filed on Feb. 20, 2018.

(30) Foreign Application Priority Data

Feb. 18, 2019   (KR) ........................ 10-2019-0018769

(51) Int. Cl.
*C07K 16/22* (2006.01)
*A61K 39/395* (2006.01)
*A61K 45/06* (2006.01)
*A61P 35/00* (2006.01)
*A61K 39/00* (2006.01)

(52) U.S. Cl.
CPC .......... *C07K 16/22* (2013.01); *A61K 39/3955* (2013.01); *A61K 45/06* (2013.01); *A61P 35/00* (2018.01); *A61K 2039/505* (2013.01); *C07K 2317/24* (2013.01); *C07K 2317/565* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 7,658,924 B2 | 2/2010 | Oliner et al. |
| 8,987,420 B2 | 3/2015 | Thurston et al. |
| 9,505,841 B2 | 11/2016 | Kim et al. |
| 9,828,422 B2 | 11/2017 | Kim et al. |
| 10,047,154 B2 | 8/2018 | Kim et al. |
| 11,498,962 B2 | 11/2022 | Koh et al. |
| 2010/0159587 A1 | 6/2010 | Brinkmann et al. |
| 2013/0129722 A1 | 5/2013 | Lowy et al. |
| 2013/0209492 A1 | 8/2013 | Thurston |
| 2015/0030603 A1 | 1/2015 | Kim et al. |
| 2015/0125455 A1 | 5/2015 | Green et al. |
| 2017/0247441 A1 | 8/2017 | Dengl et al. |
| 2018/0273613 A1 | 9/2018 | Kim et al. |

FOREIGN PATENT DOCUMENTS

| CN | 101602806 A | 12/2009 |
| CN | 102257008 A | 11/2011 |
| EP | 2832746 A1 | 2/2015 |
| KR | 1020150032075 A | 3/2015 |

OTHER PUBLICATIONS

Clark (Protein Engineering of Antibody Molecules for Prophylactic and Therapeutic Applications in Man, 1993, pp. 4-5).*
Cho et al., "COMP-Ang1: A designed angiopoietin-1 variant with nonleaky angiogenic activity," PNAS, 2004, 101(15): 5547-5552.
David S et al., "Effects of a synthetic PEG-ylated Tie-2 agonist peptide on endotoxemic lung injury and mortality," 2011, Am J Physiol Lung Cell Mol Physiol, 300: L851-L862.
Frye M, "Interfering with VE-PTP stabilizes endothelial junctions in vivo via Tie-2 in the absence of VE-cadherin," J. Exp. Med. 2015, 212(13): 2267-2287.
Goel S et al., "Effects of Vascular-Endothelial Protein Tyrosine Phosphatase Inhibition on Breast Cancer Vasculature and Metastatic Progression," 2013, J Natl Cancer Inst, 105(16): 1188-1201.

(Continued)

*Primary Examiner* — Christine J Saoud
(74) *Attorney, Agent, or Firm* — McNeill PLLC

(57) ABSTRACT

The present invention relates to mouse antibodies that bind to angiopoietin-2 (Ang2), humanized anti-Ang2 antibodies derived therefrom, and the use thereof. The anti-Ang2 antibodies have a dual function of activating the Tie2 receptor together with neutralizing Ang2. The anti-Ang2 antibodies show the property of normalizing abnormal and pathological blood vessels, and thus exhibits therapeutic efficacy against various diseases and disorders associated with abnormal blood vessels. The present invention further provides an angiogenesis inhibitor and a composition for treatment of diseases associated with abnormal Ang2 expression and Tie2 dysregulation, which comprise the antibody as an active ingredient, and a composition for diagnosing diseases associated with Ang2 inhibition and Tie2 activation, which comprises the antibody.

11 Claims, 14 Drawing Sheets

Specification includes a Sequence Listing.

(56) References Cited

OTHER PUBLICATIONS

Hansbury, et al., "Production and characterization of a Tie2 agonist monoclonal antibody," Angiogenesis, 2001, 4(1):29-36.
Hayashi M, et al., "VE-PTP regulates VEGFR2 activity in stalk cells to establish endothelial cell polarity and lumen formation," Nature Communication, 2013, 4:1-15.
Marth C et al., "ENGOT-ov-6/TRINOVA-2: Randomised, double-blind, phase 3 study of pegylated liposomal doxorubicin plus trebananib or placebo in women with recurrent partially platinum-sensitive or resistant ovarian cancer," 2017, Eur. J. Cancer, 70:111-121.
Mellberg S et al., "Transcriptional profiling reveals a critical role for tyrosine phosphatase VE-PTP in regulation of VEGFR2 activity and endothelial cell morphogenesis," 2009, FASEB J., 23: 1490-1502.
Park et al., "Normalization of Tumor Vessels by TIE2 Activation and Ang2 Inhibition Enhances Drug Delivery and Produces a Favorable Tumor Microenvironment," Cancer Cell, 2016, 30(6):953-967.
Saharinen P et al., "Therapeutic targeting of the angiopoietin-TIE pathway," 2017, Nature Review Drug Discovery, 16: 636-661.
Extended European Search Report for EP 19757411.4, Jan. 19, 2022, 7 pages.
International Search Report for International Application No. PCT/KR2019/001983, May 27, 2019, 14 pages.
Daly et al., "Angiopoietin-2 Functions as a Tie2 Agonist in Tumor Models, Where it Limits the Effects of VEGF Inhibition," Cancer Res., 2013, 73(1):108-118.
Martin-Liberal et al., "First-in-human, dose-escalation, phase 1 study of anti-angiopoietin-2 LY3127804 as monotherapy and in Combination with ramucirumab in patients with advanced solid tumours," British J Cancer, 2020, 123:1235-1243.
Martin-Liberal et al., "First-in-human, dose-escalation, phase 1 study of anti-angiopoietin-2 LY3127804 as monotherapy and in Combination with ramucirumab in patients with advanced solid tumours," British J Cancer, 2020, 123:1235-1243, Supplemental Information, 11 pages.
Oliner et al., "Suppression of angiogenesis and tumor growth by selective inhibition of angiopoietin-2," Cancer Cell, 2004, 6:507-516.
Papadopoulos et al., "A Phase I First-in-Human Study of Nesvacumab (REGN910), a Fully Human Anti-Angiopoietin-2 (Ang2) Monoclonal Antibody, in Patients with Advanced Solid Tumors," Clin Cancer Res, 2016, 22(6): 1348-1355.

\* cited by examiner

Crystal structure of Human Angiopoietin 2 RBD (PDB : 2GY7)

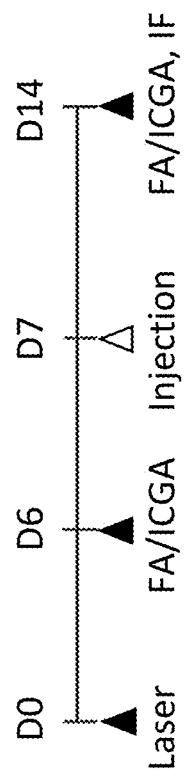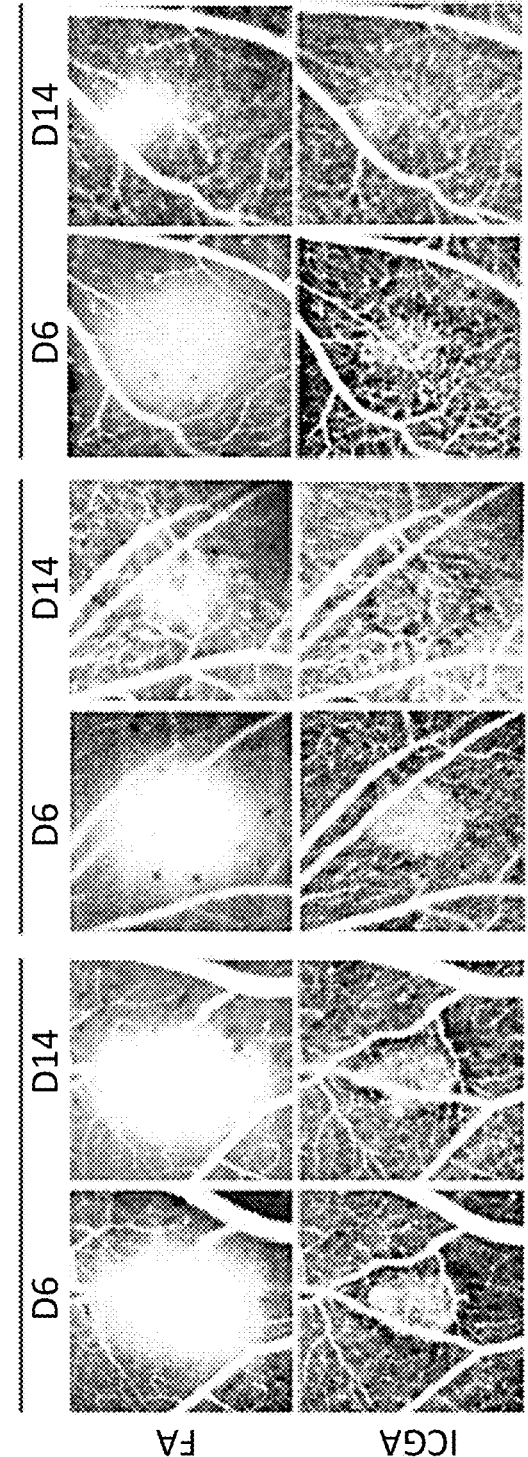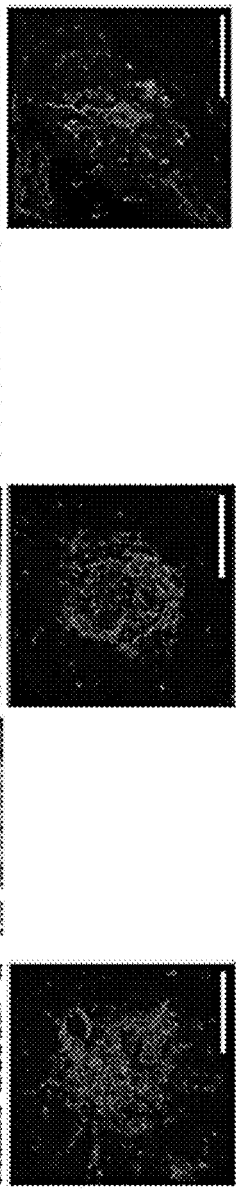
FIG. 13A
FIG. 13B

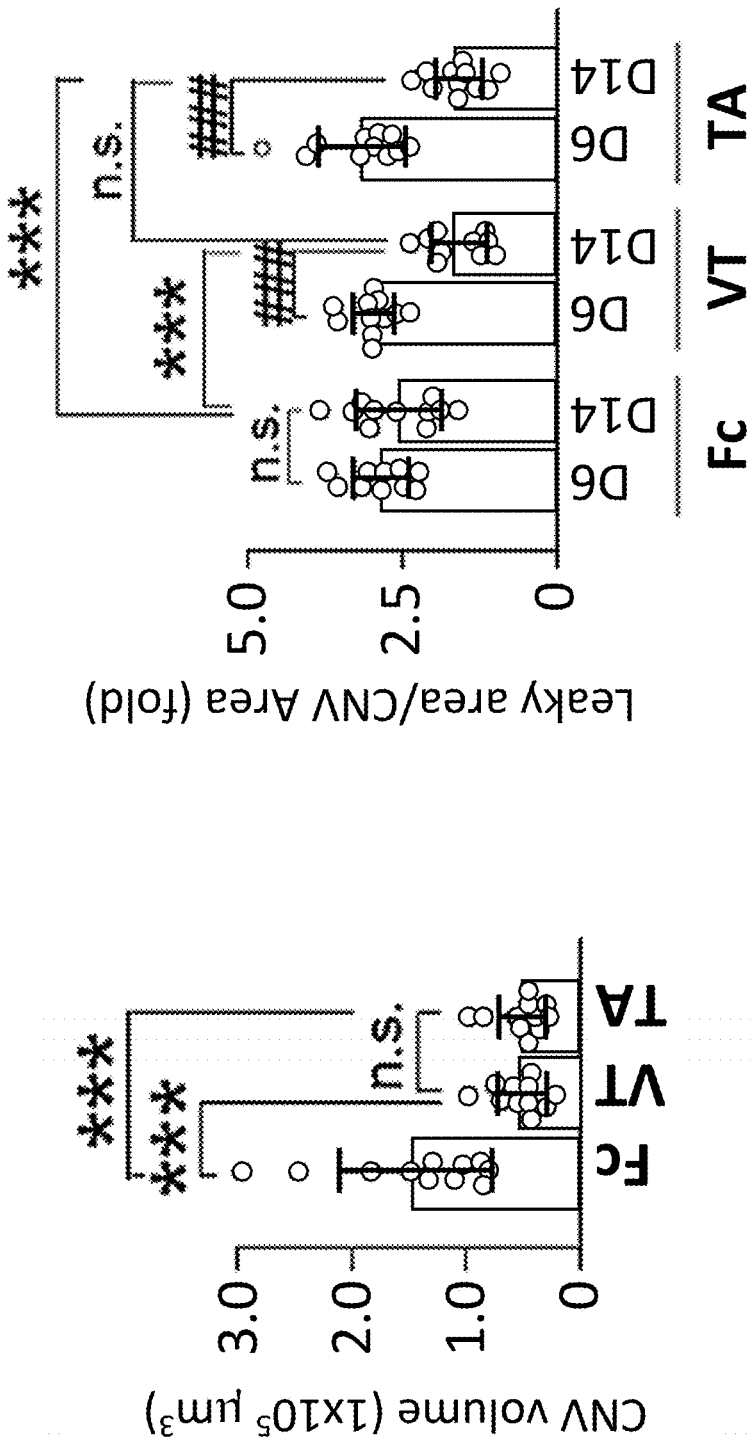
FIG. 13C
FIG. 13D
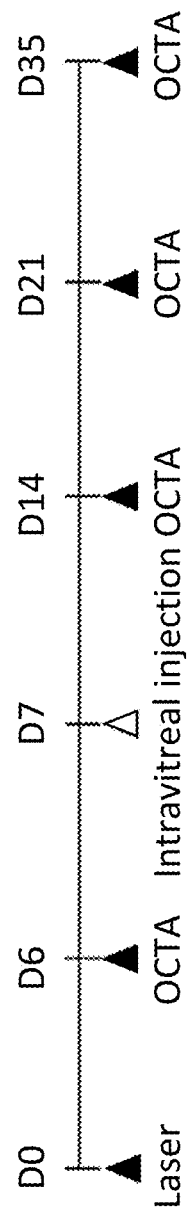
FIG. 14A

ANTI-ANGIOPOIETIN-2 ANTIBODIES THAT INDUCE TIE2 ACTIVATION

CROSS REFERENCE TO RELATED APPLICATIONS

This application is a divisional of U.S. application Ser. No. 16/995,707, filed Aug. 17, 2020, which is a continuation of International Patent Application No. PCT/KR2019/001983, filed Feb. 19, 2019, which claims priority from Korean Patent Application No. 10-2019-0018769, filed Feb. 18, 2019 and U.S. Provisional Application No. 62/633,038, filed Feb. 20, 2018, the contents of each of which are incorporated herein by reference in their entirety.

SEQUENCE LISTING

This instant application contains a Sequence Listing which has been submitted electronically in XML format and is hereby incorporated by reference in its entirety. Said XML copy, created on Aug. 15, 2022, is named "2022-08-15_01262-0002-01US_Seq_List_ST26.xml," and is 165,792 bytes in size.

FIELD OF THE INVENTION

The present invention includes an anti-Ang2 antibodies or an antigen-binding fragment thereof, which bind specifically to angiopoietin-2 (Ang2) known as a ligand that controls blood vessel formation and maintenance, a pharmaceutical composition containing the same, a nucleic acid encoding the same, a vector including the nucleic acid, an host cell transformed with the vector, and a method for producing the antibody or antigen-binding fragment thereof.

BACKGROUND ART

Angiogenesis occurs dynamically by a variety of regulatory factors during the development, growth, maintenance, and homeostasis of an organism. Blood vessels newly formed in this process act as transport channels for various biomaterials such as nutrients, oxygen, and hormones in the surrounding cells. Functionally and structurally abnormal blood vessels are the direct or indirect cause for the initiation and progression of various diseases. Tumor blood vessels aggravate hypoxia due to their defective function and structure, resulting in tumor progression and metastasis to other tissues, and also in the poor delivery of anticancer drugs into the core of the tumor mass. Defective blood vessels are also found in other various diseases and conditions, in addition to cancer. Examples thereof include various ocular diseases (e.g., diabetic macular edema, wet age-related macular degeneration), viral infections, and acute inflammatory responses such as sepsis. Thus, if a therapeutic agent capable of normalizing pathologic blood vessels is available, it can be applied to the treatment of various patients with vascular abnormalities.

The angiopoietin family plays an important role in the formation and maintenance of blood vessels, and is comprised of four angiopoietins (Ang1, Ang2, Ang3, and Ang4). Angiopoietin-1 (Ang1) binds to the Tie2 receptor present on the surface of vascular endothelial cells to phosphorylate and activate Tie2 receptor, resulting in stabilization of blood vessels. On the other hand, angiopoietin-2 (Ang2) binds to the Tie2 receptor, but acts as an antagonist to induce inactivation of the Tie2 receptor, resulting in destabilization of blood vessels and leakage of blood vessels. It was reported that the expression level of Ang2 is highly increased in the blood of cancer patients, ocular diseases, viral and bacterial infections and inflammatory diseases (Saharinen P et al., 2017, Nature Review Drug Discovery). However, Ang2 is also known to act as an agonist to induce activation of the Tie2 receptor in several processes, including lymphatic tube formation and maintenance, and thus it is believed that Ang2 performs various functions depending on the context.

Ang2-binding antibodies have been reported in several literatures (e.g., U.S. Pat. Nos. 7,658,924, and 8,987,420). It is known that most of the Ang2 antibodies reported so far inhibit the binding of Ang2 to Tie2 and thus inhibiting the formation of new blood vessel through such Ang2 neutralization efficacy. Currently, various Ang2 antibodies are being clinically tested in various cancer patients, but their anti-cancer efficacy is known to be insufficient. For example, Phase 3 clinical trials conducted by Amgen showed that the anti-cancer efficacy of the Ang2 antibody in ovarian cancer patients was insignificant (Marth C et al., 2017, Eur. J. Cancer).

In addition to antibodies, recombinant proteins that bind directly to the Tie2 receptor to induce phosphorylation and activation of Tie2 have also been reported. Examples thereof include COMP-Ang1 (Cho et al., 2004, PNAS) and Vasculotide (David S et al., 2011, Am J Physiol Lung Cell Mol Physiol) peptide consisting of five angiopoietin-1 protein fragments. However, it is considered that these proteins have a very short half-life and unstable physicochemical properties. In addition, there is a phosphatase called VE-PTP that removes a phosphate group from phosphorylated Tie2 to inactivate the Tie2, and a low molecular compound (AKB-9778) was also developed, which indirectly maintains Tie2 activity by inhibiting the activity of the enzyme VE-PTP (Goel S, 2013, J Natl Cancer Inst). However, this compound has the disadvantage of activating other receptors besides Tie2 (Frye M, 2015, J Exp. Med, Hayashi M, 2013, Nature Communication, Mellberg S et al., 2009, FASEB J.).

SUMMARY OF THE INVENTION

The present invention is directed to an antibody or antigen-binding fragment thereof that specifically binds human Angiopoietin-2 and induces Tie2 activation, wherein the antibody or antigen-binding fragment thereof binds to amino acids 289-299 of SEQ ID NO: 1, amino acids 316-322 of SEQ ID NO: 1, or amino acids 336-353 of SEQ ID NO: 1, as determined by hydrogen/deuterium exchange method.

The antibody or antigen-binding fragment thereof may bind to human and mouse Ang2. The antibody may be polyclonal or monoclonal. The antigen-binding fragment may be scFv or Fab. The antibody or fragment thereof may be humanized.

In another aspect, the invention is directed to an antibody or antigen-binding fragment that includes:
 (a) the complementarity determining regions (CDRs) of a heavy chain variable region having the HCDR1 amino acid sequence of SEQ ID NO: 3, the HCDR2 amino acid sequence of SEQ ID NO: 4, and the HCDR3 amino acid sequence of SEQ ID NO: 5; and
 (b) the CDRs of a light chain variable region comprising the LCDR1 amino acid sequence of SEQ ID NO: 6, the LCDR2 amino acid sequence of SEQ ID NO: 7, and the LCDR3 amino acid sequence of SEQ ID NO: 8.

In another aspect, the invention is directed to an antibody or antigen-binding fragment that includes:

(a) the complementarity determining regions (CDRs) of a heavy chain variable region having the HCDR1 amino acid sequence of SEQ ID NO: 13, the HCDR2 amino acid sequence of SEQ ID NO: 14, and the HCDR3 amino acid sequence of SEQ ID NO: 15; and (b) the CDRs of a light chain variable region comprising the LCDR1 amino acid sequence of SEQ ID NO: 16, the LCDR2 amino acid sequence of SEQ ID NO: 17, and the LCDR3 amino acid sequence of SEQ ID NO: 18.

In one aspect, the invention is directed to an antibody or antigen-binding fragment thereof that comprises the complementarity determining regions (CDRs) of an antibody produced from a cell line deposited with accession number KCLRF-BP-00417 or KCLRF-BP-00418.

In yet another aspect, the invention is directed to a pharmaceutical composition comprising a pharmaceutically effective amount of the antibody or antigen-binding fragment thereof described above, in association with a pharmaceutically acceptable carrier. The pharmaceutical composition may further include a small molecule inhibitor used in chemotherapy or a vascular endothelial growth factor (VEGF) antagonist. In one aspect, the VEGF antagonist may be an anti-VEGF antibody, a VEGF inhibiting fusion protein, or a small molecule kinase inhibitor.

In yet another aspect, the invention is directed to a method for inhibiting tumor growth in a patient, comprising administering to the patient a pharmaceutical composition comprising an antibody or antigen-binding fragment described above. The method may further include administering a small molecule inhibitor used in chemotherapy or a vascular endothelial growth factor (VEGF) antagonist simultaneously or step-wise with the administration of the inventive antibody or fragment thereof. The VEGF antagonist may be an anti-VEGF antibody, a VEGF inhibiting fusion protein, or a small molecule kinase inhibitor.

In yet another aspect, the invention is directed to a method for suppressing choroidal neovascularization, inhibiting ocular vascular leakage, or simultaneously triggering regeneration of choriocapillary in an ocular disease patient, the method comprising administering to the patient the pharmaceutical composition described above. The method may further include administering a small molecule inhibitor used in chemotherapy or a vascular endothelial growth factor (VEGF) antagonist simultaneously or step-wise with the administration of the inventive antibody or fragment thereof. The VEGF antagonist may be an anti-VEGF antibody, a VEGF inhibiting fusion protein, or a small molecule kinase inhibitor. The ocular disease is wet age-related macular degeneration (wAMD), diabetic macular edema (DME), or diabetic retinopathy (DR).

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

Vascular permeability was assessed by measuring FITC fluorescence in the lower chamber after adding FITC-dextran for 20 min into the upper chamber. Values are mean±SD. *p<0.05, p<0.01, *p<0.001 by one-way ANOVA.

Figure 8A:
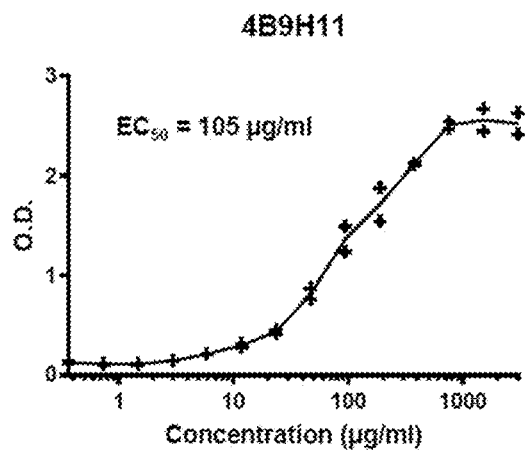
Figure 8B:
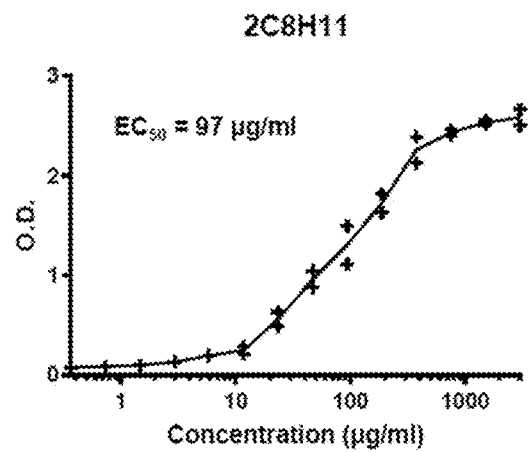

FIGS. 8A-8B. EC50 values of anti-Ang2 antibodies against mouse Ang2 by ELISA. The binding affinities of humanized anti-Ang2 antibodies for mouse Ang2 (mAng2) were measured by analyzing EC50 with ELISA. The recombinant mAng2 was coated and incubated with serially diluted anti-Ang2 antibodies, 4B9H11 and 2C8H11. Next, the plate was reacted with anti-human IgG (Fab)-HRP secondary antibody. The plate was treated with TMB solution and absorbance was measured at 450 nm for anti-Ang2 antibodies, 4B9H11 (FIG. 8A) and 2C8H11 (FIG. 8B). EC50 value was analyzed using WorkOut 2.5 program PerkinElmer™).

Figure 9:
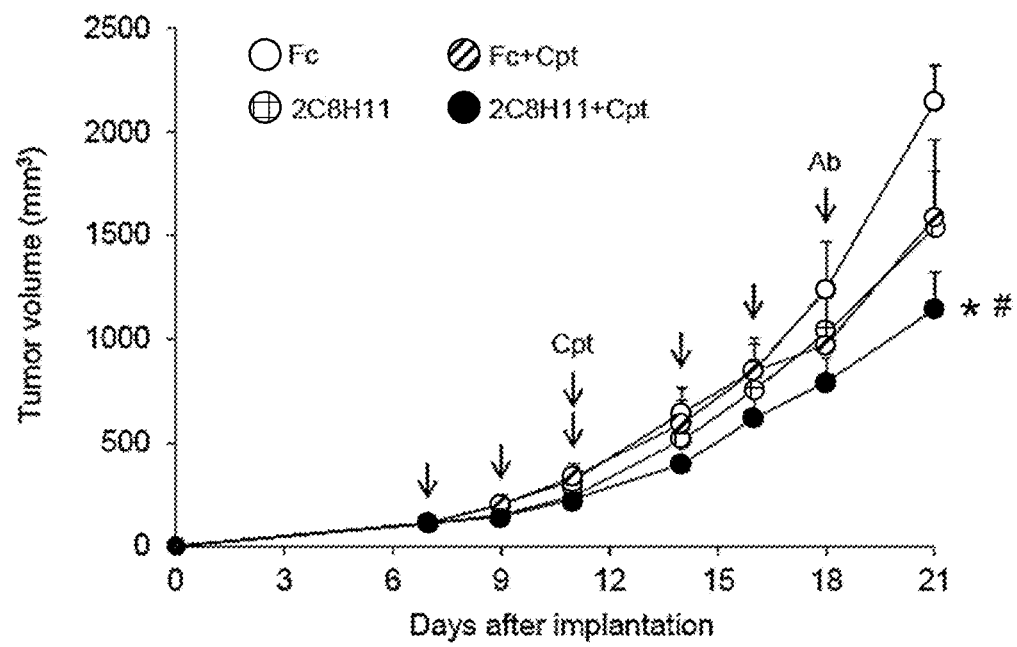

FIG. 9. Inhibition of tumor growth by humanized 2C8H11 antibodies and Cisplatin (Cpt) in LLC tumor model. LLC tumor growths were compared in mice treated as indicated, starting 7 days after tumor implantation. Black arrows indicate injections of antibodies, while red arrow indicate single injection of Cpt. n=7~9 for each group. Values are mean±SD. *p<0.05 versus Fc; #p<0.05 versus Fc+Cpt.

Figure 10A:
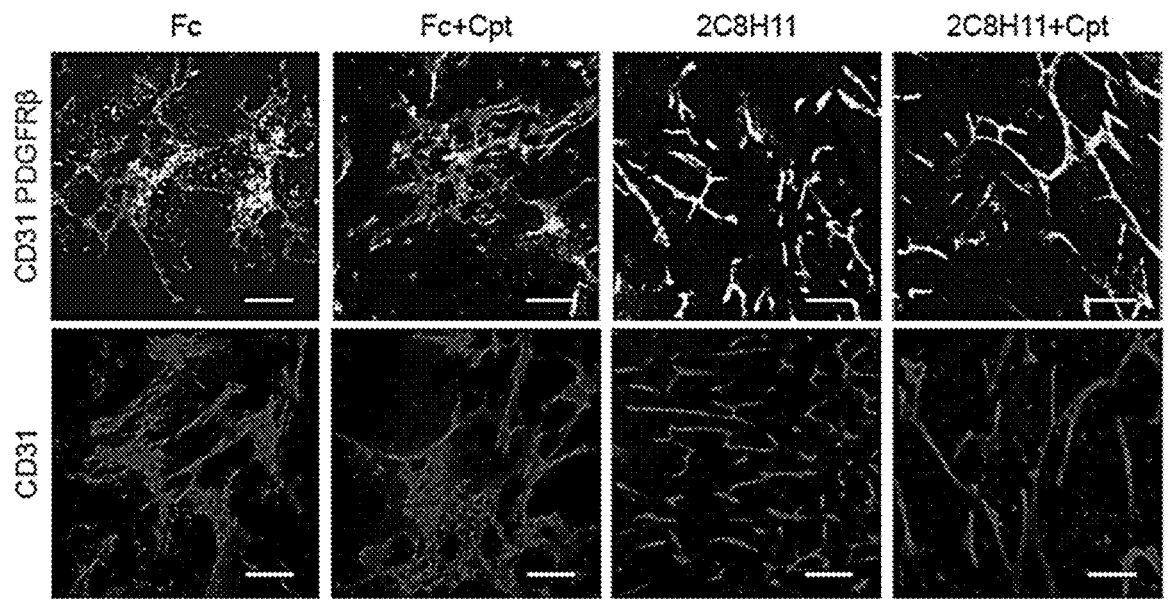
Figure 10B:
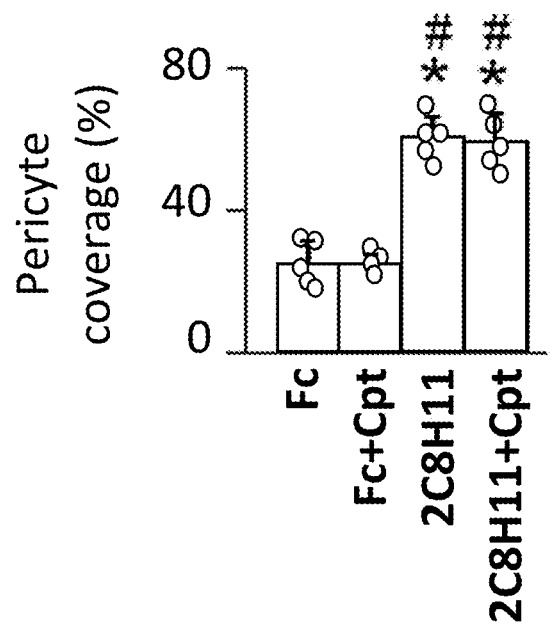
Figure 10C:
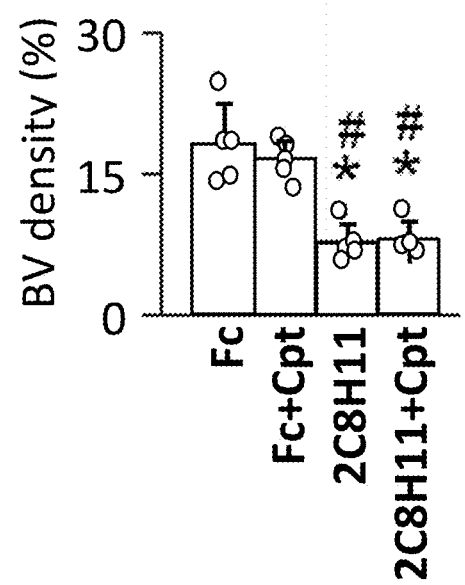

FIGS. 10A-10C. Tumor vessel normalization effect by humanized 2C8H11 antibody. PDGFRβ$^+$ pericyte coverage (FIGS. 10A and 10B) on tumor and CD31$^+$ BVs (FIGS. 10A and 10C) in intratumoral region were compared in LLC subcutaneous tumor model. Scale bar, 100 µm. n=5 for each group. Values are mean±SD. *p<0.05 versus Fc; #p<0.05 versus Fc+Cpt.

Figure 11A:
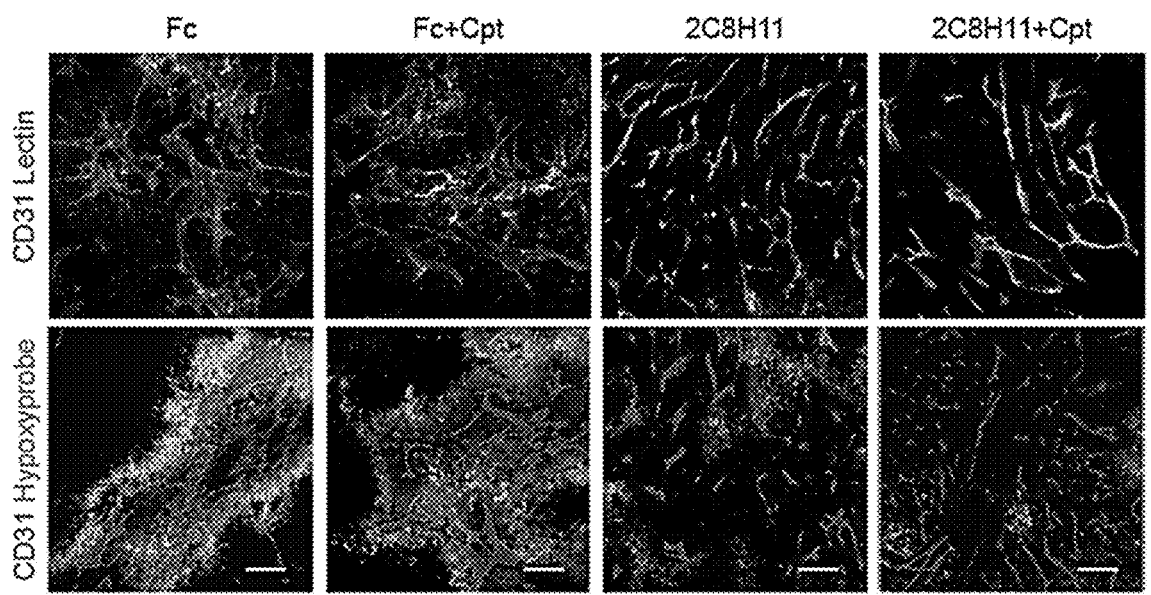
Figure 11B:
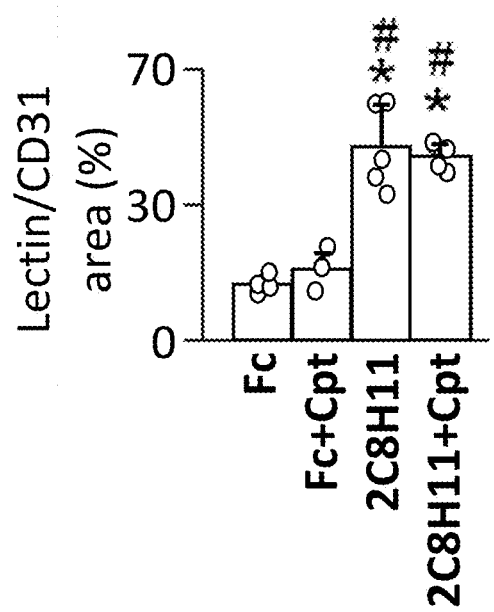
Figure 11C:
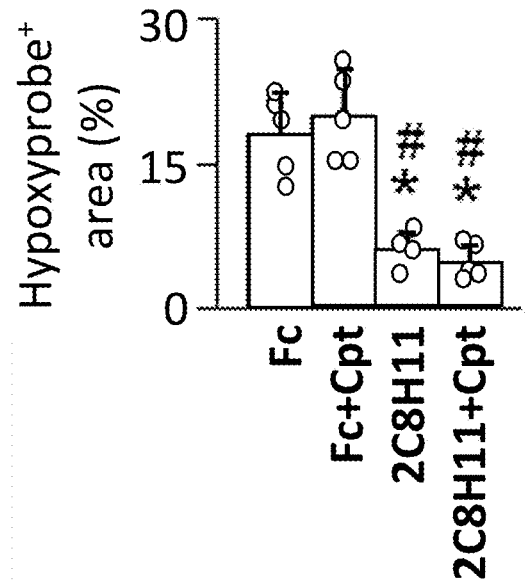

FIGS. 11A-11C. Hypoxia reduction and perfusion increase in tumor blood vessels by humanized 2C8H11 antibody. Lectin perfusion of tumor vessels (FIGS. 11A and 11B) and HYPOXYPROBE™+ (pimonidazole hydrochloride) hypoxic area (FIGS. 11A and 11C) were analyzed and compared in LLC tumor. HYPOXYPROBE™+area is presented as a percentage per total sectional area. Scale bar, 100 µm. n=5 for each group. Values are mean±SD. * p<0.05 versus Fc; #p<0.05 versus Fc+Cpt.

Figure 12A:
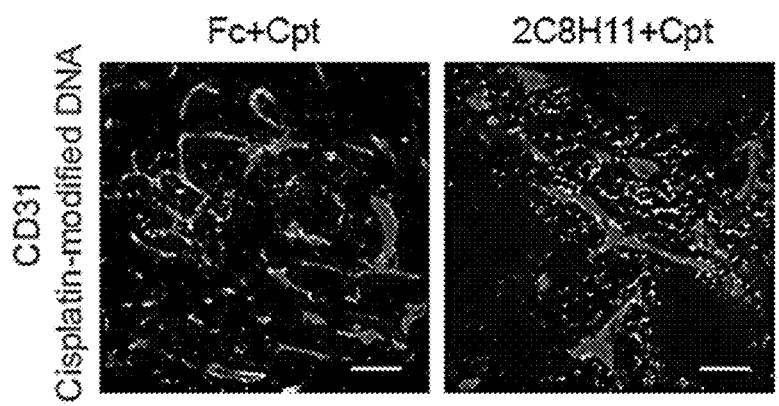
Figure 12B:
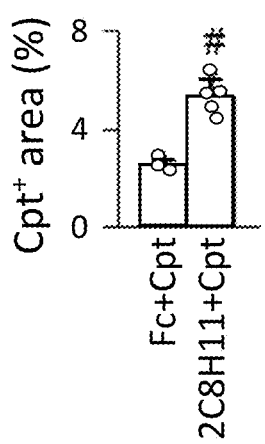

FIGS. 12A-12B. Enhanced Cpt drug delivery into the tumor core by humanized 2C8H11 antibody. Cpt$^+$ area was imaged in tumor harvested on day 21, using anti Cpt-modified DNA antibody (FIG. 12A). Cpt$^+$ area was measured as a percentage per total sectional area (FIG. 12B). Scale bar, 100 µm. n=5 for each group. Values are mean±SD. #p<0.05 versus Fc+Cpt.

FIGS. 13A-13D. CNV regression and vascular leakage suppression by intravitreous injection of 2C8H11 antibody in laser-induced CNV model. The intravitreal administration of antibodies was performed at 7 days after laser photocoagulation (FIG. 13A-13B). CD31$^+$ CNV volumes (FIG. 13C) were measured and leaky areas around CNV were calculated as the total measured hyperfluorescent areas in FA images divided by the total measured CNV areas in ICGA images at 6 and/or 14 days after laser photocoagulation (FIG. 13D). Scale bar, 100 µm. n=11 for each group. Values are mean±SD. ***p<0.001 by one-way ANOVA followed by Student-Newman-Keuls post-test; ###p<0.001 by paired Student's t-test.

Figure 14B:
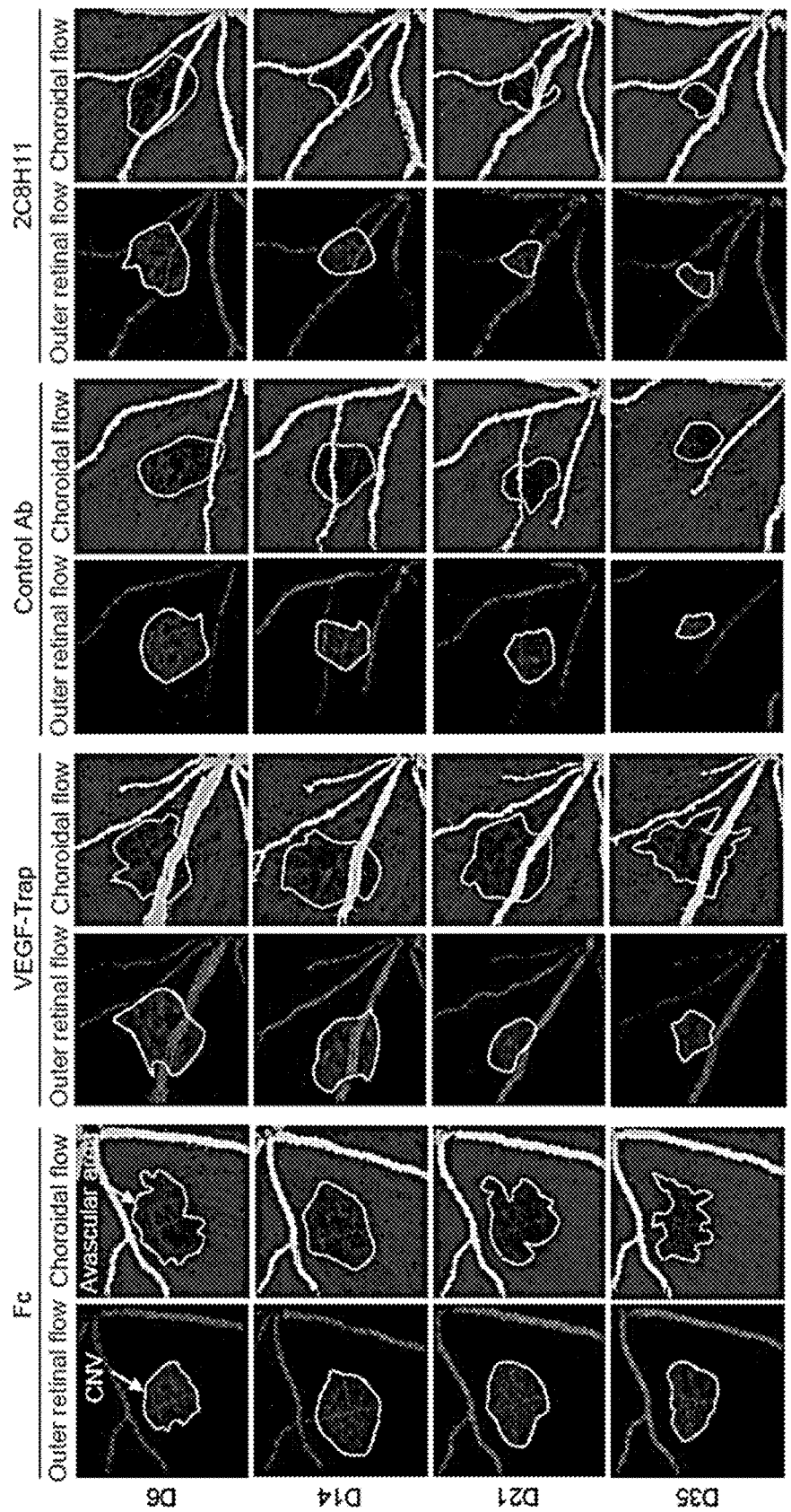
Figure 14C:
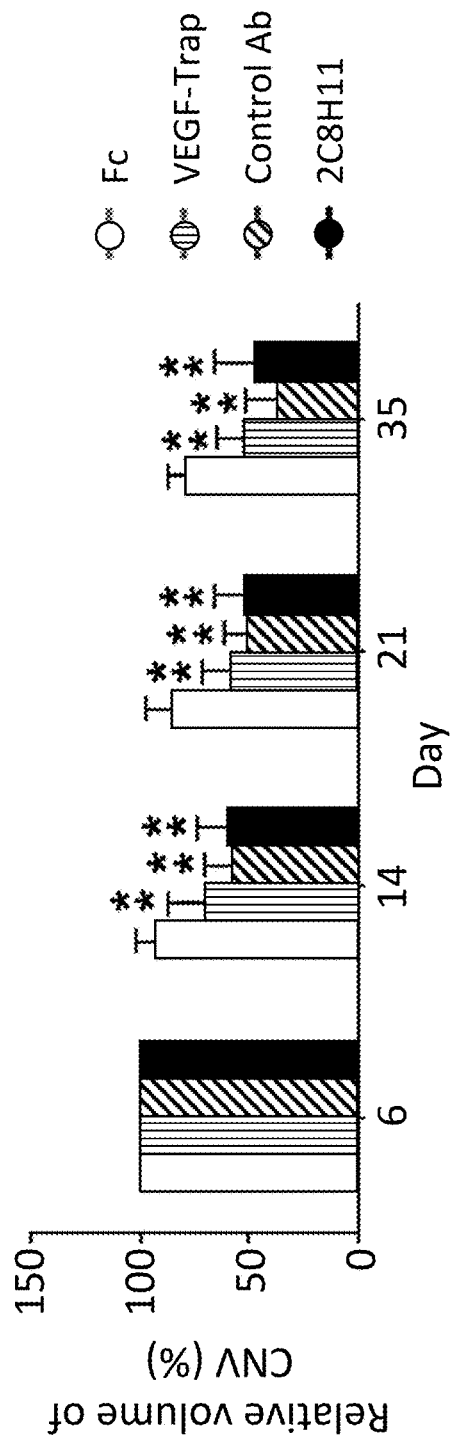
Figure 14D:
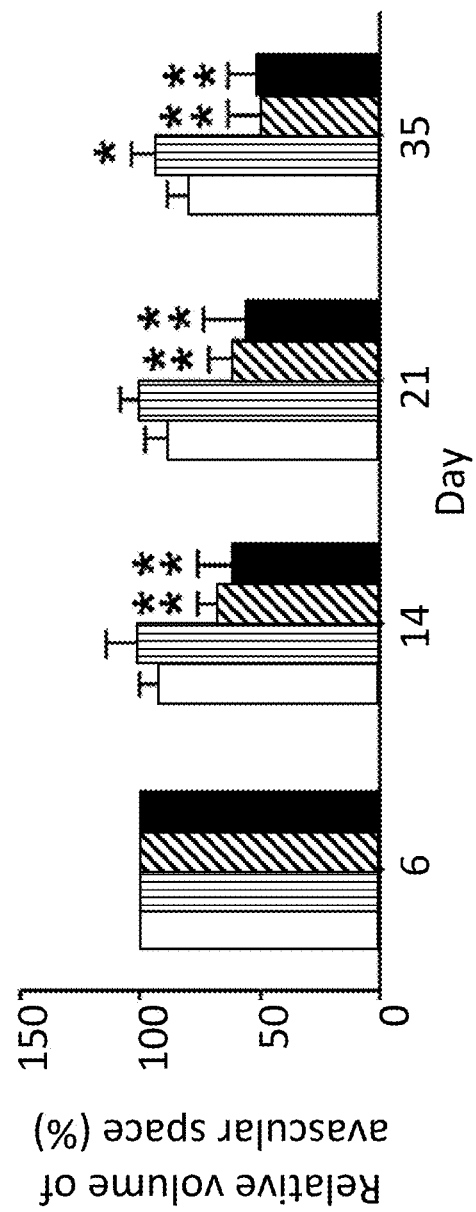

FIGS. 14A-14D. CNV regression and choriocapillary regeneration by intravitreous injection of 2C8H11 antibody. The intravitreal administration of antibodies was performed at 7 days after laser photocoagulation (FIGS. 14A-14B). The CNV volumes (area demarcated by the white dotted boundary) (FIGS. 14B-14C) and the avascular space (area demarcated by the white dotted boundary) (FIGS. 14B and 14D) surrounding the CNV were measured by OCTA imaging of eyes at 6, 14, 21 and 35 days after laser photocoagulation. n=11 for each group. Values are mean±SD. *p<0.05, **p<0.005 vs. Fc by one-way ANOVA followed by Student-Newman-Keuls post-test.

Figure 15A:
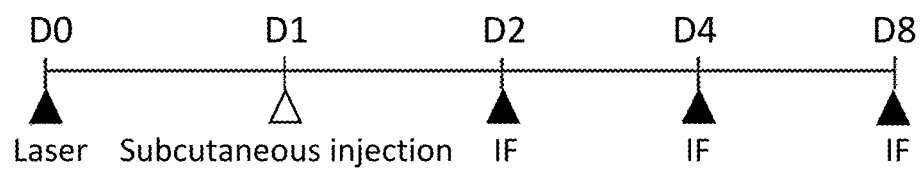
Figure 15B:
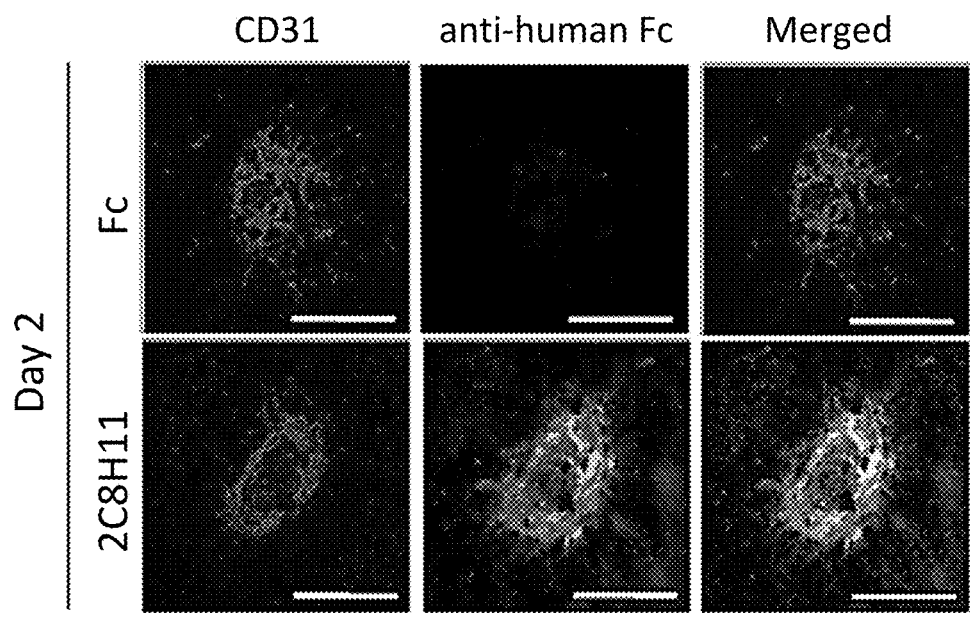
Figure 15C:
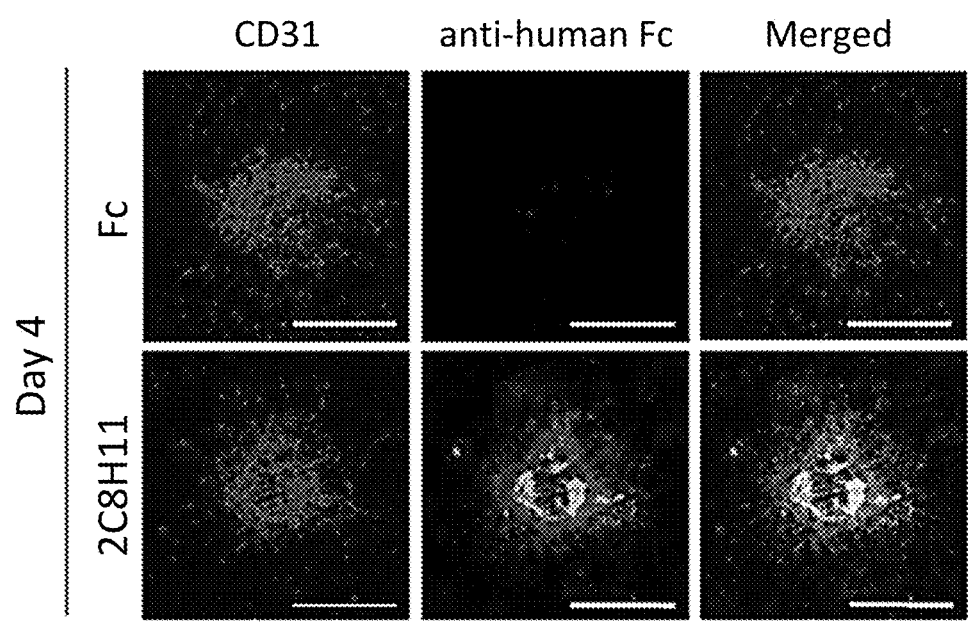
Figure 15D:
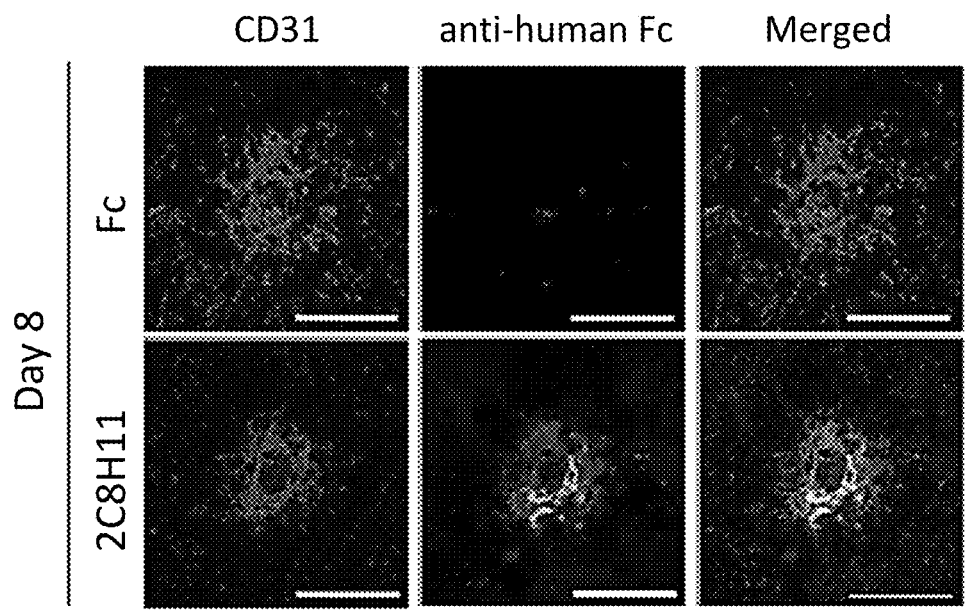

FIGS. 15A-15D. Co-localization of 2C8H11 antibody and CD31 in endothelial cells of CNV. The subcutaneous administration of 208H11 antibody was performed at 1 day after laser photocoagulation (FIG. 15A). The co-localization of 2C8H11 antibody and CD31 in endothelial cells of CNV was directly detected by anti-human IgG antibody at 2, 4, and 8 days after laser photocoagulation (FIGS. 15A-15D).

Figure 16A:
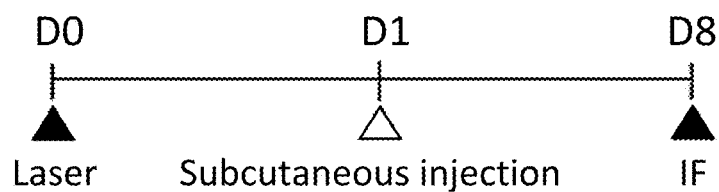
Figure 16B:
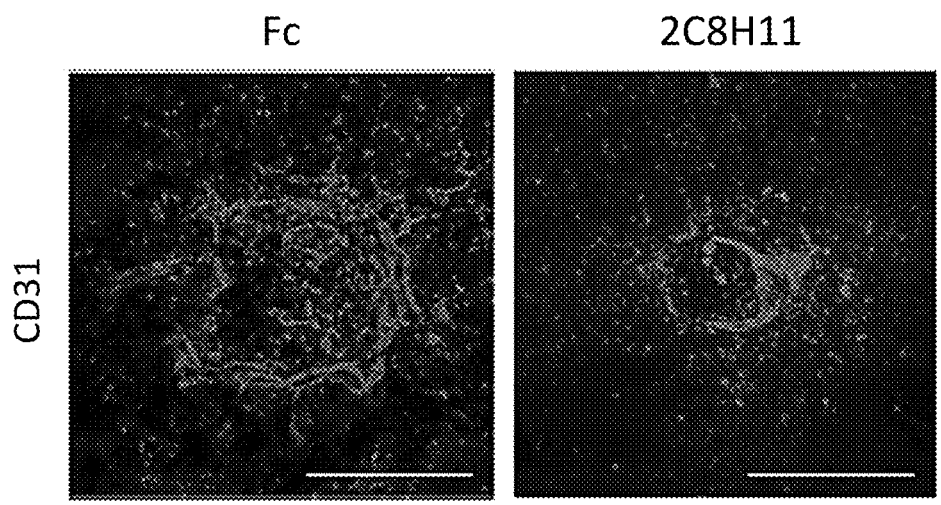
Figure 16C:
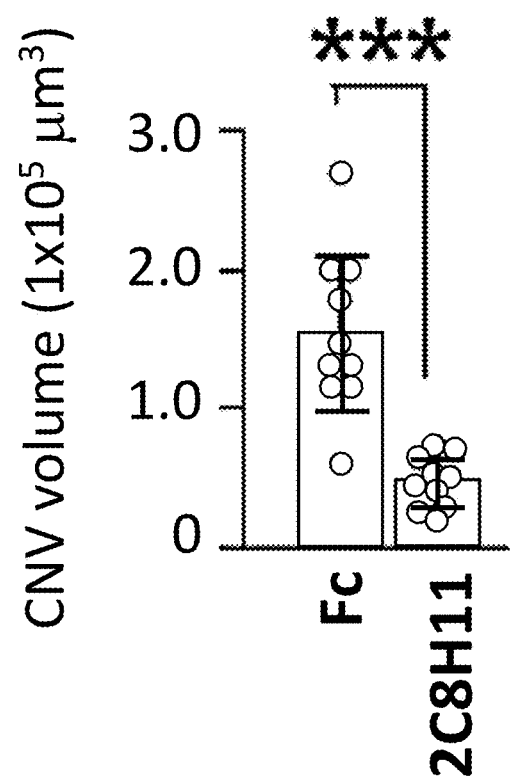

FIGS. 16A-16C. CNV inhibition effect of subcutaneously injected 2C8H11 antibody. The subcutaneous administration of 2C8H11 antibody was performed at 1 day after laser photocoagulation (FIG. 16A). CD31$^+$ CNV volumes were measured at 8 days after laser photocoagulation (FIGS. 16A-16C). Scale bar, 100 µm. n=10 for each group. Values are mean±SD. ***p<0.001 by unpaired Student's t-test.

DETAILED DESCRIPTION OF THE INVENTION

Unless defined otherwise, all technical and scientific terms used herein have the same meaning as those appreciated by those skilled in the field to which the present disclosure pertains. In general, nomenclature used herein is well-known in the art and is ordinarily used.

In the present application, "a" and "an" are used to refer to both single and a plurality of objects.

In one aspect, the present invention is directed to an antibody or antigen-binding fragment thereof that specifically binds human Angiopoietin-2 and induces Tie2 activation, wherein the antibody or antigen-binding fragment thereof binds to amino acids of SEQ ID NO: 115, amino acids of SEQ ID NO: 116, or amino acids of SEQ ID NO: 117.

The amino acids of SEQ ID NO: 115 is corresponding to the amino acids 336-353 of SEQ ID NO: 1, the amino acids of SEQ ID NO: 116 is corresponding to the amino acids 289-299 of SEQ ID NO: 1, and the amino acids of SEQ ID NO: 117 is corresponding to the amino acids 316-322 of SEQ ID NO: 1.

As herein used, the term "antibody specifically binding to Ang2" refers to antibody that binds to Ang2 resulting in inhibition of the biological activity of Ang2, and is used interchangeably with "anti-Ang2 antibody", "Ang2-binding antibody".

The "antibody" used herein is an immunoglobulin molecule which is immunologically reactive to a specific antigen, and means a protein molecule acting as a receptor that specifically recognizes an antigen, and may include all of a polyclonal antibody, a monoclonal antibody (single clone antibody), a whole antibody, and an antibody fragment. Further, the antibody may include a chimeric antibody (e.g., humanized murine antibody) and a bivalent or bispecific molecule (e.g., bispecific antibody), a diabody, a triabody, and a tetrabody.

The whole antibody has a structure having two full length light chains and two full length heavy chains, and each light chain may be linked to a heavy chain via a disulfide bond. The whole antibody includes IgA, IgD, IgE, IgM, and IgG, and the IgG is a subtype, and includes IgG1, IgG2, IgG3, and IgG4.

In the present disclosure, the antibody or antigen-binding fragment thereof may bind to human and mouse Ang2.

The antibody fragment means a fragment retaining an antigen-binding function, and includes Fab, Fab', F(ab')2, scFv, and Fv, etc.

The Fab has a structure of variable regions of a light chain and a heavy chain and a constant region of the light chain and a first constant region (CH1 domain) of the heavy chain, and has one antigen-binding site. The Fab' is different from the Fab in that the Fab' has a hinge region including one or more cysteine residues at C terminal of a heavy chain CH1 domain. The F(ab')2 antibody is produced by achieving the disulfide bonding of the cysteine residue in the hinge region of the Fab'.

The Fv (variable fragment) refers to the minimum antibody fragment only having the heavy chain variable region and the light chain variable region. In double-stranded Fv (dsFv), the heavy chain variable region and the light chain variable region are linked by the disulfide bond. In the single chain Fv (scFv), the heavy chain variable region and the light chain variable region generally are linked by a covalent bond using a peptide linker. These antibody fragment may be obtained by using a proteolytic enzyme (for example, the Fab may be obtained by restriction-cutting the whole antibody with papain, and F(ab')2 fragment may be obtained by cutting with pepsin), and may be constructed by a recombinant DNA technology (for example, amplification by PCR (Polymerase Chain Reaction) method using DNA encoding the heavy chain of the antibody or the variable region thereof and DNA encoding the light chain or the variable region thereof as a template and using a primer pair, and amplification with combination of the DNA encoding the peptide linker of the primer pair allowing both ends thereof to link to the heavy chain or the variable region thereof and the light chain or the variable region thereof, respectively).

In the present disclosure, the antibody or antigen-binding fragment thereof may be humanized. Preferably, the anti-Ang2 antibody according to the present invention may be a fully human antibody selected from a human antibody library, but is not limited thereto.

The antibody or antigen-binding fragment thereof according to the present invention is characterized by containing a heavy chain variable region including a heavy chain CDR1 having an amino acid sequence of SEQ ID NO: 3, a heavy chain CDR2 having an amino acid sequence of SEQ ID NO: 4, a heavy chain CDR3 having an amino acid sequence of SEQ ID NO: 5; and a light chain variable region including a light chain CDR1 having an amino acid sequence of SEQ ID NO: 6, a light chain CDR2 having an amino acid sequence of SEQ ID NO: 7, a light chain CDR3 having an amino acid sequence of SEQ ID NO: 8.

The antibody or antigen-binding fragment thereof according to the present invention is characterized by containing a heavy chain variable region including a heavy chain CDR1 having an amino acid sequence of SEQ ID NO: 13, a heavy chain CDR2 having an amino acid sequence of SEQ ID NO: 14, a heavy chain CDR3 having an amino acid sequence of SEQ ID NO: 15; and a light chain variable region including a light chain CDR1 having an amino acid sequence of SEQ ID NO: 16, a light chain CDR2 having an amino acid sequence of SEQ ID NO: 17, a light chain CDR3 having an amino acid sequence of SEQ ID NO: 18.

In the present invention, the antibody or antigen-binding fragment thereof is characterized by containing the heavy chain variable region including the amino acid sequence of SEQ ID NOs: 9, 19, 43, 47, 51, 55, 59, 63, 67, 71, 75, 79, 83, 87, 91, 95, 99, 103, 107 or 111; and the light chain variable region including the amino acid sequence of SEQ ID NOs: 11, 21, 44, 48, 52, 56, 60, 64, 68, 72, 76, 80, 84, 88, 92, 96, 100, 104, 108 or 112, but is not limited thereto.

The amino acid sequence of the antibody may be substituted by conservative substitution. The "conservative substitution" refers to modification of polypeptide including substitution of at least one amino acid with an amino acid having similar biochemical properties to corresponding polypeptide without causing loss of biological or biochemical function. "Conservative amino acid substitution" refers to a substitution in which an amino acid residue is replaced with an amino acid residue having similar side chains. Classes of the amino acid residues having similar side chains are defined in the art. These classes include amino acids having basic side chains (e.g., lysine, arginine, histidine), amino acids having acidic side chains (e.g., aspartic acid, glutamic acid), amino acids having uncharged polar side chains (e.g., glycine, asparagine, glutamine, serine, threonine, tyrosine, cysteine), amino acids having non-polar side chains (e.g., alanine, valine, leucine, isoleucine, proline, phenylalanine, methionine, tryptophan), amino acids having beta-branched side chains (e.g., threonine, valine, isoleucine), and amino acids having aromatic side chains (e.g., tyrosine, phenylalanine, tryptophan, histidine). It is anticipated that the antibody of the present invention is able to still retain an activity while having the conservative amino acid substitution.

In the present invention, the antibody or antigen-binding fragment thereof is characterized by containing the complementary determining regions (CDRs) of an antibody produced from a cell line deposited with accession number KCLRF-BP-00417 or KCLRF-BP-00418.

The inventive anti-Ang2 antibody sequences may vary from the sequences provided in the present application. For example, amino sequences may vary from those set out above in that (a) the variable regions may be segregated away from the constant domains of the light chains, (b) the amino acids may vary from those set out above while not drastically affecting the chemical properties of the residues thereby (so-called conservative substitutions), (c) the amino acids may vary from those set out above by a given percentage, e.g., 80%, 85%, 90%, 91%, 92%, 93%, 94%, 95%, 96%, 97%, 98% or 99% homology. Alternatively, the nucleic acids encoding the antibodies may (a) be segregated away from the constant domains of the light chains, (b) vary from those set out above while not changing the residues coded thereby, or (c) may vary from those set out above by a given percentage, e.g., 70%, 75%, 80%, 85%, 90%, 91%, 92%, 93%, 94%, 95%, 96%, 97%, 98% or 99% homology.

In making conservative changes in amino acid sequence, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is also understood in the art that the substitution of like amino acids can be made effectively on the basis of hydrophilicity. For instance, the greatest local average hydrophilicity of a protein, as governed by the hydrophilicity of its adjacent amino acids, correlates with a biological property of the protein. It is understood that an amino acid can be substituted for another having a similar hydrophilicity and produce a biologically or immunologically modified protein. In such changes, the substitution of amino acids whose hydrophilicity values are within +/−2 is preferred, those that are within +/−1 are particularly preferred, and those within +/−0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

In another aspect, the present invention relates to a pharmaceutical composition containing the antibody or antigen-binding fragment thereof as an active ingredient.

The pharmaceutical composition is characterized by containing a pharmaceutically effective amount of the antibody or an antigen-binding fragment thereof according to the invention and a pharmaceutically acceptable carrier.

The pharmaceutical composition may further include a small molecule inhibitor used in chemotherapy or a vascular endothelial growth factor (VEGF) antagonist. The VEGF antagonist may be an anti-VEGF antibody, a VEGF inhibiting fusion protein, or a small molecule kinase inhibitor.

In another aspect, the present invention relates to a pharmaceutical composition for preventing or treating ocular disease containing the antibody or antigen-binding fragment thereof as an active ingredient.

In another aspect, the present invention relates to a method for suppressing choroidal neovascularization, inhibiting ocular vascular leakage, or simultaneously triggering regeneration of choriocapillary in an ocular disease patient, the method comprising administering to the patient the pharmaceutical composition described above.

The pharmaceutical composition for preventing or treating ocular disease may further include a small molecule inhibitor used in chemotherapy or a vascular endothelial growth factor (VEGF) antagonist. The VEGF antagonist may be an anti-VEGF antibody, a VEGF inhibiting fusion protein, or a small molecule kinase inhibitor.

The method may further include administering a small molecule inhibitor used in chemotherapy or a vascular endothelial growth factor (VEGF) antagonist simultaneously or step-wise with the administration of the inventive antibody or fragment thereof. The VEGF antagonist may be an anti-VEGF antibody, a VEGF inhibiting fusion protein, or a small molecule kinase inhibitor.

The anti-Ang2 antibody or antigen-binding fragment thereof has a function of inhibiting abnormal angiogenesis by inhibiting the function of Ang2, and thus has an effect of preventing or treating ocular diseases accompanied by vascular abnormalities.

As herein used, the term "preventing" refers to any action that inhibits or slows the progression of ocular diseases by administration of a composition according to the present invention, and the term "treating" refers to inhibiting, alleviating, or eliminating the development of ocular diseases.

In the present invention, the ocular disease is wet age-related macular degeneration (wAMD), diabetic macular edema (DME), or diabetic retinopathy (DR), but is not limited thereto.

As herein used, the term "macular degeneration" refers to a condition in which neovascularization abnormally grows, so causes macula damage and affects vision. Macular degeneration occurs mainly in over 50 years of age and is divided into non-exudative (dry type) or exudative (wet type). In particular, in the case of wet AMD, blindness can be caused.

The cause of the AMD has not yet been clarified, but it is known that risk factors are age; and environmental factors including smoking, hypertension, obesity, genetic predisposition, excessive UV exposure, low serum antioxidant concentrations and the like.

As herein used, the term "macular edema" refers to the swelling of the macula of the retina, and the swelling occurs due to fluid leakage from the retinal blood vessels. Blood leaks from the weak blood vessel wall, enters the localized area of the retinal macula which is the color-sensing nerve ending and in which the retinal conic is abundant. The image is then faded to the right of the center or center of the center area. Visual acuity decreases gradually over several months.

As herein used, the term "diabetic retinopathy" refers to a complication of the eye in which visual acuity is reduced due to disturbance of microcirculation of the retina due to peripheral circulatory disorder caused by diabetes. Initially, it can cause light problems of visual acuity, but eventually it can cause blindness. Diabetic retinopathy can occur in anyone with Type 1 diabetes or Type 2 diabetes.

The present invention provides a pharmaceutical composition including a therapeutically effective amount of anti-Ang2 antibody and a pharmaceutically acceptable carrier. The "pharmaceutically acceptable carrier" is a material that is able to be added in the active ingredient to help formulation or stabilization of the preparation, and it does not cause significant adverse toxicological effects to patients.

The carrier refers to a carrier or diluent that does not inhibit biological activity and properties of an administered compound without stimulating the patients. The pharmaceutically acceptable carrier in the composition to be formulated as a liquid solution is sterilized and is suitable for a living body. Saline, sterile water, Ringer's solution, buffered saline, albumin injection solution, dextrose solution, maltodextrin solution, glycerol, ethanol may be used as the carrier, or at least one component thereof may be mixed to be used, and other conventional additives such as an antioxidant, buffer, a bacteriostatic agent, etc., may be added as needed. In addition, the composition may be prepared into formulations for injection, such as an aqueous solution, suspension, emulsion, etc., pill, a capsule, a granule or a tablet by further adding diluent, dispersant, surfactant, binder and lubricant thereto. Other carriers are described in, for example, [Remington's Pharmaceutical Sciences (E. W. Martin)]. The composition may contain the therapeutically effective amount of at least one anti-Ang2 antibody.

The pharmaceutically acceptable carrier includes sterile aqueous solution or dispersion and sterile powder for preparing extemporaneous sterile injectable solution or dispersion. The use of such media and agents for pharmaceutical active materials is known in the art. The composition is preferably formulated for parenteral injection. The composition may be formulated as a solution, a micro-emulsion, a liposome, or other ordered structures suitable for high drug concentration. The carrier may be, for example, a solvent or dispersion medium containing water, ethanol, polyol (for example, glycerol, propylene glycol and liquid polyethylene glycol, etc.,) and suitable mixtures thereof. In some cases, the composition may include, isotonic agent, for example, sugar, polyalcohols such as mannitol, sorbitol, or sodium chloride. The sterile injectable solution may be prepared by incorporating a required amount of active compound into an appropriate solvent with one kind of the above-described components or a combination thereof, followed by sterile micro filtration as needed. In general, the dispersion is prepared by incorporating the active compound into a sterile vehicle containing basic dispersion medium and other required components from the above-described components. The sterile powder for preparing the sterile injectable solution is obtained by vacuum drying and freeze-drying (lyophilization) active ingredient powder and any additional desirable component powder from previously sterile-filtered solution.

The pharmaceutical composition may be administered orally or parenterally in the dosage and frequency that may vary depending on severity of suffering patients. The composition may be administered to a patient as a bolus or by continuous infusion as needed. For example, the bolus administration of the antibody of the present invention which is presented as a Fab fragment may have an amount of 0.0025 to 100 mg/kg body weight, 0.025 to 0.25 mg/kg, 0.010 to 0.10 mg/kg or 0.10 to 0.50 mg/kg. For the continuous infusion, the antibody of the present invention which is presented as the Fab fragment may be administered at 0.001 to 100 mg/kg kg/min, 0.0125 to 1.25 mg/kg/min, 0.010 to 0.75 mg/kg/min, 0.010 to 1.0 mg/kg/min or 0.10 to 0.50 mg/kg/min for 1 to 24 hours, 1 to 12 hours, 2 to 12 hours, 6 to 12 hours, 2 to 8 hours, or 1 to 2 hours. When the antibody of the present invention which is presented as a full-length antibody (having a complete constant region is administered, an administration amount may be about 1 to 10 mg/kg body weight, 2 to 8 mg/kg, or 5 to 6 mg/kg. The full-length antibody is typically administered via injection that lasts for 30 minutes to 35 minutes. An administration frequency depends on the severity of the condition. The frequency may be 3 times every week to once in a week or in two weeks.

In addition, the composition may be administered to a patient via a subcutaneous injection. For example, the anti-Ang2 antibody having an administration amount of 10 to 100 mg may be weekly, biweekly, or monthly administered to a patient through subcutaneous injection.

As used herein, the "therapeutically effective amount" means an amount sufficient to treat diseases at a reasonable benefit/risk ratio applicable for medical treatment, and an amount of a combination of the anti-Ang2 antibody. The exact amount may vary depending on a number of factors that include components and physical characteristics of a therapeutic composition, intended patient population, individual patient considerations, etc., but are not limited thereto, and may be easily determined by those skilled in the art. When completely considering these factors, it is important to administer the minimum amount sufficient to obtain the maximum effect without the side effect, and this dosage may be easily determined by an expert in the field.

The dosage of the pharmaceutical composition of the present invention is not specifically limited, but is changed according to various factors including a health state and weight, severity of the disease of a patient, and a drug type, an administration route, and administration time. The composition may be administered in routes that are typically allowed in mammals including rat, mouse, cattle, human, etc., for example, orally, rectally, intravenously, subcutaneously, intrauterinely or intracerebrovascularly in a single dose amount or multidose per day.

In another aspect, the present invention relates to a pharmaceutical composition for preventing or treating cancer containing the antibody or antigen-binding fragment thereof as an active ingredient.

In another aspect, the present invention relates to a method for inhibiting tumor growth and treating cancer in a patient, comprising administering to the patient a pharmaceutical composition comprising the antibody or antigen-binding fragment described above. The method may further include administering a small molecule inhibitor used in chemotherapy or a vascular endothelial growth factor (VEGF) antagonist simultaneously or step-wise with the administration of the inventive antibody or fragment thereof. The VEGF antagonist may be an anti-VEGF antibody, a VEGF inhibiting fusion protein, or a small molecule kinase inhibitor.

As herein used, the term "cancer" or "tumor" typically refers to or describes a physiological condition of mammals characterized by cell growth/proliferation that is not controlled.

The cancer that can be treated with the composition of the present invention is not particularly limited, and includes both solid cancer and blood cancer. Examples of such cancers include squamous cell carcinoma, small cell lung cancer, non-small cell lung cancer, adenocarcinoma of the lung, squamous cell carcinoma of the lung, peritoneal cancer, skin cancer, skin or intraocular melanoma, rectal cancer, anal cancer, esophageal cancer, small intestine cancer, endocrine cancer, parathyroid cancer, adrenal cancer, soft tissue sarcoma, urethral cancer, chronic or acute leukemia, lymphoma, hepatocellular carcinoma, gastrointestinal cancer, pancreatic cancer, glioma, cervical cancer, ovarian cancer, liver cancer, bladder cancer, liver tumors, breast cancer, colon cancer, endometrial or uterine cancer, salivary gland cancer, kidney cancer, prostate cancer, vulva cancer, thyroid cancer, head and neck cancer, brain cancer, osteosarcoma and the like, but are not limited to.

The composition for preventing or treating cancer comprises the anti-Ang2 antibody and the constitution thereof is the same as the composition included in the composition for preventing or treating eye disease, so the description of each constitution applies equally to a composition for preventing or treating cancer.

Present application also contemplates using anti-Ang2 antibodies described herein in conjunction with chemo- or radiotherapeutic intervention, or other treatments. It also may prove effective, in particular, to combine anti-Ang2 antibodies with other therapies that target different aspects of Ang2 function.

In another embodiment, the inventive antibodies may be linked to at least one agent to form an antibody conjugate in order to increase the efficacy of antibody molecules as diagnostic or therapeutic agents.

In another aspect of the present invention, the present invention relates to a nucleic acid encoding the antibody or antigen-binding fragment thereof.

The nucleic acid used herein may be present in a cell, a cell lysate, or may also be present in a partially purified form or a substantially pure form. The nucleic acid is "isolated" or "is substantially pure" when it is purified from other cell components or other contaminants, for example, other cell nucleic acid or protein by standard techniques including alkaline/SDS treatment, CsCl banding, column chromatography, agarose gel electrophoresis, and other techniques well-known in the art. The nucleic acid of the present invention may be, for example, DNA or RNA, and may include an intron sequence, or may not include the intron sequence.

In still another aspect of the present invention, the present invention relates to a recombinant expression vector including the nucleic acid.

For expression of the antibody or fragments thereof, DNA encoding the light chain and the heavy chain having a partial length or a full length may be obtained by standard molecular biology techniques (for example, PCR amplification or cDNA cloning using a hybridoma that expresses a target antibody), and the DNA may be "operably bound" to transcription and translation control sequences to be inserted into the expression vector.

Term "operably bound" used herein may indicate that an antibody gene is ligated into the vector so that the transcription and translation control sequences in the vector have an intended function to control transcription and translation of the antibody gene. The expression vector and an expression control sequence are selected so as to have compatibility with a host cell for expression to be used. The light chain gene of the antibody and the heavy chain gene of the antibody are inserted into a separate vector, or both genes are inserted into the same expression vector. The antibody is inserted into the expression vector by a standard method (for example, ligation of an antibody gene fragment and a complementary restriction enzyme site on a vector or when the restriction enzyme site is not present at all, blunt end ligation). In some cases, the recombinant expression vector may encode a signal peptide that facilitates secretion of the antibody chain from the host cell. The antibody chain gene may be cloned into the vector so that the signal peptide is bound to an amino terminal of the antibody chain genes according to a frame. The signal peptide may be an immunoglobulin signal peptide or a heterologous signal peptide (i.e. signal peptide derived from proteins except for immunoglobulin). In addition, the recombinant expression vector has a regulatory sequence that controls the expression of the antibody chain genes in the host cell. The "regulatory sequence" may include a promoter, an enhancer and other expression control element (for example, polyadenylation signal) controlling the transcription or translation of the antibody chain gene. Those skilled in the art is able to recognize that design of the expression vector may vary by changing the regulatory sequences according to factors such as selection of the host cell to be transformed, an expression level of the protein, etc.

In still another aspect, the present invention relates to a cell transformed with the recombinant expression vector.

The cell used to produce the antibody of the present disclosure may be a prokaryote, yeast or higher eukaryotic cell, but is not limited thereto.

In particular, strains of the genus *Bacillus* such as *Escherichia coli, Bacillus subtilis* and *Bacillus tuligensis, Streptomyces, Pseudomonas* (for example, *Pseudomonas putida*), and prokaryotic host cells such as *Proteus mirabilis* and *Staphylococcus* (for example, *Staphylococcus carnosus*) can be used.

The interest in animal cells is the largest and examples of useful host cell lines include, but are not limited to, COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, or HT1080.

The nucleic acid or the vector is transfected into the host cell. For the "transfection", various kinds of generally used techniques such as electrophoresis, calcium phosphate precipitation, DEAE-dextran transfection, lipofection, etc., may be used to introduce an exogenous nucleic acid (DNA or RNA) into a prokaryotic host cell or an eukaryotic host cell. The antibody according to the present invention may be expressed in an eukaryotic cell, preferably, in a mammalian host cell, in consideration of applicability into a mammalian cell. The mammalian host cells suitable for expression of the antibody may include a Chinese hamster ovary (CHO) cell (for example, including a dhfr-CHO cell used together with a DHFR selection marker), an NSO myeloma cell, a COS cell, or a SP2 cell, etc., as examples.

In another aspect, the present invention relates to a method for producing the anti-Ang2 antibody or antigen-binding fragment thereof, including culturing the host cells and expressing the antibody or antigen-binding fragment thereof.

When the recombinant expression vector encoding the antibody gene is introduced into the mammalian host cell, the antibody may be produced by culturing the host cell for a sufficient period of time so that the antibody is expressed in the host cell, or more preferably, for a sufficient period of time so that the antibody is secreted into a culture medium in which the host cell is cultured.

In some cases, the expressed antibody may be separated from the host cell and purified for uniformity. The separation or the purification of the antibody may be performed by a separation method, a purification method generally used for protein, for example, chromatography. The chromatography may include, for example, affinity chromatography, ion exchange chromatography or hydrophobic chromatography including protein A column and protein G column. In addition to the chromatography, the antibody may be separated and purified by additionally combining with filtration, ultrafiltration, salting out, dialysis, etc.

EXAMPLES

Hereinafter, the present invention will be described in more detail with reference to the following Examples. However, the following examples are only for exemplifying the present invention and it will be obvious to those skilled in the art that the scope of the present invention is not construed to be limited to these examples.

Example 1: Preparation of Mouse Monoclonal Anti-Ang2 Antibody 1-1: Mouse Immunization with Human Ang2

To be used as an antigen, the receptor binding domain (RBD) of human Ang2 (hAng2, SEQ ID NO: 2) was cloned into a vector containing CMV promotor and transiently expressed by transfecting into HEK293F cell line. After 5 days of incubation, the expressed recombinant human Ang2-RBD was purified by affinity column. Five-week-old BALB/c mice were immunized with purified human Ang2-RBD (100 μg/injection) mixed with an adjuvant twice weekly for 6 weeks. Anti-Ang2 antibody titers in the sera of immunized mice were examined by hAng2 ELISA. When the antibody titer (1:5,000 dilution) suitably increased (OD>1.0), the spleens were extracted from the immunized mice, and B lymphocytes were isolated therefrom and fused with cultured myeloma cells (SP2/0). The fused cells were cultured in a HAT medium containing hypoxanthine, aminopterin and thymidine, and hybridoma cells comprised only of a fusion of myeloma cells and B lymphocytes were selected therefrom and cultured. Survived hybridoma cells were seeded in 96-well plates and the culture supernatants were tested by hAng2 ELISA. Hybridoma pools showing a positive signal were selected for clonal selection through limiting dilution. Finally, about 50 monoclonal hybridoma lines were established. Among them, several Ang2-binding antibodies showed Tie2-activating activity. Candidate antibodies were selected based on Tie2 activating level and high affinity to human Ang2, later processed for humanization.

TABLE 1

Human Angiopoietin-2 full-length (hAng2) and receptor-binding domain (RBD) sequences

| Human Angiopoietin-2 full-length (SEQ ID NO: 1) | |
|---|---|
| MWQIVFFTLSCDLVLAAAYNNFRKSMDSIGKKQYQVQHGSCSYTFLLPEM | 50 |
| DNCRSSSSPYVSNAVQRDAPLEYDDSVQRLQVLENIMENNTQWLMKLENY | 100 |
| IQDNMKKEMVEIQQNAVQNQTAVMIEIGTNLLNQTAEQTRKLTDVEAQVL | 150 |
| NQTTRLELQLLEHSLSTNKLEKQILDQTSEINKLQDKNSFLEKKVLAMED | 200 |
| KHIIQLQSIKEEKDQLQVLVSKQNSIIEELEKKIVTATVNNSVLQKQQHD | 250 |
| LMETVNNLLTMMSTSNSAKDPTVAKEEQISFRDCAEVFKSGHTTNGIYTL | 300 |
| TFPNSTEEIKAYCDMEAGGGGWTIIQRREDGSVDFQRTWKEYKVGFGNPS | 350 |
| GEYWLGNEFVSQLTNQQRYVLKIHLKDWEGNEAYSLYEHFYLSSEELNYR | 400 |
| IHLKGLTGTAGKISSISQPGNDFSTKDGDNDKCICKCSQMLTGGWWFDAC | 450 |
| GPSNLNGMYYPQRQNTNKFNGIKWYYWKGSGYSLKATTMMIRPADF | 496 |
| | |
| Human Angiopoietin-2 receptor-binding domain(RBD)(SEQ ID NO: 2) | |
| EEQISFRDCAEVFKSGHTTNGIYTLTFPNSTEEIKAYCDMEAGGGGWTII | 50 |
| QRREDGSVDFQRTWKEYKVGFGNPSGEYWLGNEFVSQLTNQQRYVLKIHL | 100 |
| KDWEGNEAYSLYEHFYLSSEELNYRIHLKGLTGTAGKISSISQPGNDFST | 150 |
| KDGDNDKCICKCSQMLTGGWWFDACGPSNLNGMYYPQRQNTNKFNGIKWY | 200 |
| YWKGSGYSLKATTMMIRPADF | 221 |

1-2: Production and Purification of Mouse Monoclonal Anti-Ang2 Antibodies

In order to produce the anti-Ang2 antibody selected based on the ELISA positive reaction, hybridoma cells were cultured in 10% FBS-containing DMEM (Dulbecco's Modified Eagle's Medium) in a T75 (75 cm² area) flask. When the confluency of the cells reached about 90%, the cells were washed with PBS, incubated with 50 ml of serum-free medium (SFM, GIBCO™ and cultured at 37° C. for 3 days. Then, the culture medium in which the antibody was secreted from each monoclonal hybridoma was collected, centrifuged to remove the cells, and the culture supernatant was collected and filtered. The antibody was then purified using an AKTA™ purification device (GE Healthcare) equipped with a Protein G affinity column (GE Healthcare). The purified antibody was concentrated by substituting the supernatant with PBS using a centrifugal filter unit (AMICON®)

1-3: Identification and Screening of Tie2 Receptor Activating Anti-Ang2 Antibodies To investigate whether the mouse anti-Ang2 antibodies induce the downstream signaling of the Tie2 receptor in endothelial cells, HUVECs (LONZA™) were treated with a combination of hAng2 protein and anti-Ang2 antibody, and then the level of Akt phosphorylation, the main downstream signaling protein of Tie2 receptor, was analyzed by immunoblotting. As a negative control group, the full-length hAng2 (R&D® Systems) alone was treated into the cells.

Specifically, HUVECs (1×10⁵ cells/ml) were cultured in EGM-2 medium (LONZA™) at 37° C. in a 60 mm culture dish. Cells (90% confluency) were incubated with serum-free EBM-2 medium for 4 hrs for serum starvation. The serum-starved HUVECs were treated with a mixture of anti-Ang2 antibody and hAng2 protein (1 µg/ml, R&D® Systems) and further incubated for 30 min. The cells were washed with cold PBS, treated with lysis buffer, and lysed at 4° C. for 20 min. Then, the cell lysates were prepared by centrifugation at 13000 rpm for 15 min. 5× SDS sample buffer was added to the cell lysate and the cell lysate was boiled at 95° C. for 5 min. Then, the cell lysate was subjected to SDS PAGE and proteins were transferred to a nitrocellulose membrane (GE).

To investigate Akt phosphorylation, the blot was blocked with 5% skim milk-containing TBS-T for 1 hr at room temperature (RT), and incubated with anti-phospho-Akt antibody (S473) at 4° C. for about 8 hrs. The amount of phospho-Akt was visualized by an enhanced chemiluminescence (ECL). Then, the membrane was incubated in a stripping buffer (Thermo) for 15 min, and then reprobed with an anti-Akt antibody to determine the amount of total Akt.

Figure 1:
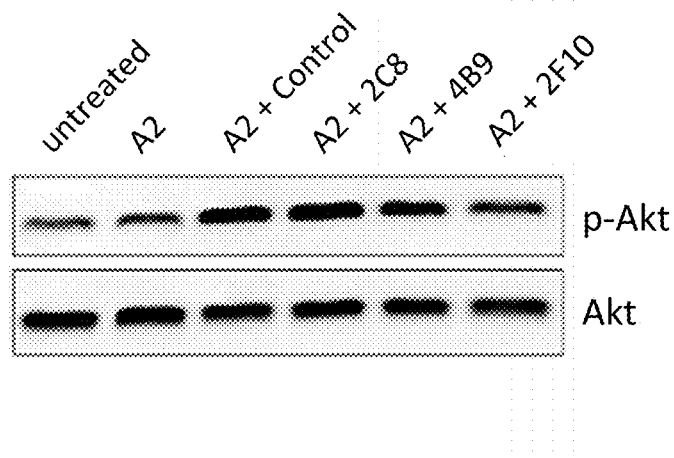
FIG. 1. Akt phosphorylation induced by anti-Ang2 antibodies. HUVECs were serum-starved for 6 hrs and incubated with COMP-Ang1 (CA1, 0.5 µg/ml) or anti-Ang2 antibodies (control, 2C8, 4B9, 2F10 and 4E2 respectively) in the absence or presence of human Ang2 (1 µg/ml) for 30 min. Cell lysates were subjected to SDS-PAGE/Western blotting and blots were probed with anti-phospho-Akt (S473) or anti-Akt antibody.

Akt phosphorylation at S473 was strongly induced in several groups treated with a combination of hAng2 and anti-Ang2 antibody such as 2C8, 4B9, 2F10 and 4E2, respectively (FIG. 1).

1-4: Affinity Measurement of Anti-Ang2 Antibodies Against hAng2 by Octet OCTET® Analysis The affinity of mouse monoclonal antibody against hAng2 was measured using OCTET® system (ForteBio, real-time, label-free bio-layer interferometry system for determination of affinity, kinetics, and concentration). Specifically, buffer and samples were measured in total 200 µl/well using Black 96-well plates (96 well F-type black plates, Greiner). The biosensor used for affinity measurements was hydrated for 10 min before measurement with AR2G tip (ForteBio OCTET®). After the hydration, hAng2 was diluted in 10 mM sodium acetate, pH 6.0 buffer at a concentration of 10 µg/ml, fixed on AR2G biosensor, and blocked with 1M ethanolamine. The mouse monoclonal anti-Ang2 antibodies were diluted to 50, 25, 12.5, 6.25, 3.125, and 0 nM with 1× kinetic buffer, and subjected to association for 300 seconds and dissociation for 900 seconds. For affinity measurement ($K_D$), the association rate (K-on) and dissociation rate (K-off) were analyzed by binding curve (global) and fitted to 1:1 binding model using OCTET® data analysis v9.0.0.10 program. The $K_D$ values were shown in the following Table 2. The affinities to hAng2 of mouse anti-Ang2 antibodies are shown in Table 2.

TABLE 2

Affinities to hAng2 of mouse anti-Ang2 antibodies

| Antibody | Kon (1/Ms) | Koff (1/s) | $K_D$ (M) |
|---|---|---|---|
| 2C8 | 7.78E+04 | 3.54E−06 | 4.55E−11 |
| 2F10 | 1.24E+05 | 1.71E−05 | 1.38E−10 |
| 4B9 | 1.37E+05 | 5.04E−07 | 3.68E−12 |
| 4E2 | 2.83E+04 | 1.34E−04 | 4.74E−09 |

Example 2: DNA Gene Sequence Analysis of Mouse Anti-Ang2 Antibodies

The DNA nucleotide sequence of the antibody (derived from hybridoma cells) selected in Example 1-3 was analyzed. Specifically, hybridoma cells (2× 106 cells/ml) were cultured in 10% FBS-containing DMEM and then total RNA was obtained using RNeasy® mini kit (Qiagen). Next, RNA concentration was measured, and cDNA was synthesized through reverse transcription (RT) reaction. To amplify the heavy and light chain variable region gene sequences of the monoclonal antibodies produced in each hybridoma cell, PCR was carried out using Mouse Ig-Primer set (NOVAGEN®) under the following conditions using above cDNA as a template: 94° C. 5 min; [1 min at 94° C., 1 min at 50° C., 2 min at 72° C.]×35 cycles; 6 min at 72° C.; cooling to 4° C. The PCR product obtained from each reaction was cloned into a TA vector, and subjected to DNA sequencing, thereby obtaining the nucleotide sequences encoding the CDR, heavy-chain variable region and light-chain variable region of each antibody (Tables 3 to 10).

TABLE 3

CDR sequence of mouse anti-Ang2 antibody 4B9

| Antibody | CDR Sequence | | |
|---|---|---|---|
| 4B9 | Heavy Chain CDR Sequence | | |
| | CDRH1-KABAT DYYMY (SEQ ID NO: 3) | CDRH2-KABAT TISVGGSFTYYPDSVKG (SEQ ID NO: 4) | CDRH3-KABAT DWGLRPWFVY (SEQ ID NO: 5) |
| | Light Chain CDR Sequence | | |
| | CDRL1-KABAT KASQDVSTAVA (SEQ ID NO: 6) | CDRL2-KABAT WASTRHT (SEQ ID NO: 7) | CDRL3-KABAT QQHYSTPPT (SEQ ID NO: 8) |

TABLE 4

Variable region sequence of mouse anti-Ang2 antibody 4B9

| Antibody | Variable Region Sequence |
|---|---|
| 4B9 | Heavy Chain Variable Region Sequence<br>EVQLVESGGGLVKPGGSLKLSCAASGFTFSDYYMYWVRQTPE<br>KRLEWVATISVGGSFTYYPDSVKGRFTISRDNAKNNLYLQMSS<br>LKSEDTAMYYCARDWGLRPWFVYWGQGTLVTVSA (SEQ ID NO: 9)<br><br>GAAGTGCAGCTGGTGGAGTCTGGGGGAGGCTTAGTGAAGCCTG<br>GAGGGTCCCTGAAACTCTCCTGTGCAGCCTCTGGATTCACTTTC<br>AGTGACTATTACATGTATTGGGTTCGCCAGACTCCGGAAAAGAG<br>GCTGGAGTGGGTCGCAACCATTAGTGTTGGTGGTAGTTTCACCT<br>ACTATCCAGACAGTGTGAAGGGGCGATTCACCATCTCCAGAGAC<br>AATGCCAAGAACAACCTGTACCTGCAAATGAGCAGTCTGAAGTC<br>TGAGGACACAGCCATGTATTACTGTGCAAGAGACTGGGGATTAC<br>GACCCTGGTTTGTTTACTGGGGCCAAGGGACTCTGGTCACTGTC<br>TCTGCA (SEQ ID NO: 10)<br><br>Light Chain Variable Region Sequence<br>DIVMTQSHKFMSTSVGDRVSITCKASQDVSTAVAWYQQKPGQ<br>SPKLLIYWASTRHTGVPDRFTGSGSGTDYTLTISSVQAEDLA<br>LYYCQQHYSTPPTFGSGTKLEIK (SEQ ID NO: 11)<br><br>GACATTGTGATGACCCAGTCTCACAAATTCATGTCCACATCAGT<br>AGGAGACAGGGTCAGCATCACCTGCAAGGCCAGTCAGGATGTA<br>GTACTGCTGTAGCCTGGTATCAACAAAAACCAGGGCAATCTCCT<br>AAACTACTGATTTACTGGGCATCCACCCGGCACACTGGAGTCCC |

TABLE 4-continued

Variable region sequence of mouse anti-Ang2 antibody 4B9

| Antibody | Variable Region Sequence |
|---|---|
| | TGATCGCTTCACAGGCAGTGGATCTGGGACAGATTATACTCTCA<br>CCATCAGCAGTGTGCAGGCTGAAGACCTGGCACTTTATTACTGT<br>CAGCAACATTATAGCACTCCTCCCACGTTCGGCTCGGGGACAAA<br>GTTGGAAATAAAA<br>(SEQ ID NO: 12) |

TABLE 5

CDR sequence of mouse anti-Ang2 antibody 2C8

| Antibody | CDR Sequence | | |
|---|---|---|---|
| 2C8 | Heavy Chain CDR Sequence | | |
| | CDRH1-KABAT | CDRH2-KABAT | CDRH3-KABAT |
| | SYWMH (SEQ ID NO: 13) | MIDPSDSETRLNQKFKD (SEQ ID NO: 14) | RFYYGSDWYFDV (SEQ ID NO: 15) |
| | Light Chain CDR Sequence | | |
| | CDRL1-KABAT | CDRL2-KABAT | CDRL3-KABAT |
| | KASQDVGTAVA (SEQ ID NO: 16) | WASTRHT (SEQ ID NO: 17) | QQYSSYPLT (SEQ ID NO: 18) |

TABLE 6

Variable region sequence of mouse anti-Ang2 antibody 2C8

| Antibody | Variable Region Sequence |
|---|---|
| 2C8 | Heavy Chain Variable Region Sequence<br>QVQLQQSGPQLVRPGASVKISCKASGYSFTSYWMHWVKQRPGQ<br>GLEWIGMIDPSDSETRLNQKFKDKASLTVDKSSSTAYMQLS<br>SPTSGDSAVYYCARRFYYGSDWYFDVWGAGSTVTVSS<br>(SEQ ID NO: 19)<br><br>CAGGTGCAACTGCAGCAGTCTGGGCCTCAGCTGGTTAGGCCTG<br>GGGCTTCAGTGAAGATATCCTGCAAGGCTTCTGGTTACTCATT<br>CACCAGCTACTGGATGCACTGGGTGAAGCAGAGGCCTGGACAA<br>GGTCTTGAGTGGATTGGCATGATTGATCCTTCCGATAGTGAAA<br>CTAGGTTAAATCAGAAGTTCAAGGACAAGGCCTCATTGACTGT<br>AGACAAATCCTCCAGCACAGCCTACATGCAACTCAGCAGCCCG<br>ACATCTGGGGACTCTGCGGTCTATTACTGTGCAAGACGTTTTT<br>CACTACGGGTGGACTGGTACTTCGATGTCTGGGGCGCAGGGTC<br>CACGGTCACCGTCTCCTCA<br>(SEQ ID NO: 20)<br><br>Light Chain Variable Region Sequence<br>DIVMTQSHKFMSTSVGDRVSITCKASQDVGTAVAWYQQKPG<br>QSPKLLIYWASTRHTGVPDRFTGSGSGTDFTLTISNVQSED<br>LADYFCQQYSSYPLTFGSGTKLEIK (SEQ ID NO: 21)<br><br>GACATTGTGATGACCCAGTCTCACAAATTCATGTCCACATCAG<br>TAGGAGACAGGGTCAGCATCACCTGCAAGGCCAGTCAGGATGT<br>GGGTACTGCTGTAGCCTGGTATCAACAGAAACCAGGTCAATCT<br>CCTAAACTACTGATTTACTGGGCATCCACCCGGCACACTGGAG<br>TCCCTGATCGCTTCACAGGCAGTGGATCTGGGACAGATTTCAC<br>TCTCACCATTAGCAATGTGCAGTCTGAAGACTTGGCAGATTAT<br>TTCTGTCAGCAATATAGCAGCTATCCTCTCACGTTCGGCTCGG<br>GGACAAAGTTGGAAATAAAA (SEQ ID NO: 22) |

TABLE 7

CDR sequence of mouse anti-Ang2 antibody 2F10

| Antibody | CDR Sequence | | |
|---|---|---|---|
| | Heavy Chain CDR Sequence | | |
| 2F10 | CDRH1-KABAT | CDRH2-KABAT | CDRH3-KABAT |
| | DYYMY (SEQ ID NO: 23) | TINDGGSYTYYPDSVKG (SEQ ID NO: 24) | DWGLRPWFVY (SEQ ID NO: 25) |
| | Light Chain CDR Sequence | | |
| | CDRL1-KABAT | CDRL2-KABAT | CDRL3-KABAT |
| | KASQDVSTAVA (SEQ ID NO: 26) | WASTRHT (SEQ ID NO: 27) | QQHYTTPPT (SEQ ID NO: 28) |

TABLE 8

Variable region sequence of mouse anti-Ang2 antibody 2F10

| Antibody | Variable Region Sequence |
|---|---|
| 2F10 | Heavy Chain Variable Region Sequence<br>QVQLVESGGGLVKPGGSLKLSCAASGFTFSDYYMYWIRQTPEK<br>RLEWVATINDGGSYTYYPDSVKGRFTISRDNAKNNLYLQMSS<br>LKSEDTAMYYCARDWGLRPWFVYWGQGTLVTVSA<br>(SEQ ID NO: 29)<br><br>GAAGTGCAGCTGGTGGAGTCTGGGGGAGGCTTAGTGAAGCCTG<br>GAGGGTCCCTGAAACTCTCCTGTGCAGCCTCTGGATTCACTTTC<br>AGTGACTATTACATGTATTGGATTCGCCAGACTCCGGAAAAGAGG<br>CTGGAGTGGGTCGCAACCATTAATGATGGTGGTAGTTACACCTAC<br>TATCCAGACAGTGTGAAGGGGCGATTCACCATCTCCAGAGACAA<br>TGCCAAGAACAACCTGTACCTGCAAATGAGCAGTCTGAAGTCTG<br>AGGACACAGCCATGTATTACTGTGCAAGAGACTGGGGATTACGA<br>CCCTGGTTTGTTTACTGGGGCCAAGGGACTCTGGTCACTGTCTC<br>TGCA (SEQ ID NO: 30)<br><br>Light Chain Variable Region Sequence<br>DIVMTQSHKFMSTSVGDRVSITCKASQDVSTAVAWYQQKPGQS<br>PKLLIYWASTRHTGVPDRFTGSGSGTDYTLTISSVQAEDLALY<br>YCQQHYTTPPTFGSGTKLEIK (SEQ ID NO: 31)<br><br>GACATTGTGATGACCCAGTCTCACAAATTCATGTCCACATCAGTA<br>GGAGACAGGGTCAGCATCACCTGCAAGGCCAGTCAGGATGTGA<br>GTACTGCTGTAGCCTGGTATCAACAAAAACCAGGGCAATCTCCTA<br>AACTACTGATTTACTGGGCATCCACCCGGCACACTGGAGTCCCT<br>GATCGCTTCACAGGCAGTGGATCTGGGACAGATTATACTCTCAC<br>CATCAGCAGTGTGCAGGCTGAAGACCTGGCACTTTATTACTGTC<br>AGCAACATTATACCACTCCTCCCACGTTCGGCTCGGGGACAAAG<br>TTGGAAATAAAA (SEQ ID NO: 32) |

TABLE 9

CDR sequence of mouse anti-Ang2 antibody 4E2

| Antibody | CDR Sequence | | |
|---|---|---|---|
| | Heavy Chain CDR Sequence | | |
| 4E2 | CDRH1-KABAT | CDRH2-KABAT | CDRH3-KABAT |
| | GYNMN (SEQ ID NO: 33) | NIDPYYGGTSYNQKFKG (SEQ ID NO: 34) | YGNYVDY (SEQ ID NO: 35) |
| | Light Chain CDR Sequence | | |
| | CDRL1-KABAT | CDRL2-KABAT | CDRL3-KABAT |
| | KASQDVSTAVA (SEQ ID NO: 36) | WASTRHT (SEQ ID NO: 37) | QQHYNTPPT (SEQ ID NO: 38) |

TABLE 10

Variable region sequence of mouse anti-Ang2 antibody 4E2

| Antibody | Variable Region Sequence |
|---|---|
| 4E2 | Heavy Chain Variable Region Sequence<br>EVQLQQSGPELEKPGASVKISCKASGYSFTGYNMNWKQSNGKS<br>LEWIGNIDPYYGGTSYNQKFKGKATLTVDKSSSTAYMQLKSL<br>TSEDSAVYYCVRYGNYVDYWGQGTTLTVSS (SEQ ID NO: 39)<br><br>CAGCTGCAGCAGTCTGGACCTGAGCTGGAGAAGCCTGGCGCTT<br>CAGTGAAGATATCCTGCAAGGCTTCTGGTTACTCATTCACTGG<br>CTACAACATGAACTGGGTGAAGCAGAGCAATGGAAAGAGCCTT<br>GAGTGGATTGGAAATATTGATCCTTACTATGGTGGTACTAGCT<br>ACAACCAGAAGTTCAAGGGCAAGGCCACATTGACTGTAGACAA<br>ATCCTCCAGCACAGCCTACATGCAGCTCAAGAGCCTGACATCT<br>GAGGACTCTGCAGTCTATTACTGTGTAAGGTATGGTAACTACG<br>TGGACTACTGGGGCCAAGGCACCACTCTCACAGTCTCCTCA<br>(SEQ ID NO: 40)<br><br>Light Chain Variable Region Sequence<br>DIVMTQSHKFMSTSVGDRVSITCKASQDVSTAVAWYQQKPGQS<br>PKLLIYWASTRHTGVPDRFTGSGSGTDYTLTISSVQAEDLALY<br>YCQQHYNTPPTFGSGTKLEIK (SEQ ID NO: 41)<br><br>GACATTGTGATGACCCAGTCCCACAAATTCATGTCCACATCAG<br>TAGGAGACAGGGTCAGCATCACCTGCAAGGCCAGTCAGGATGT<br>GAGTACTGCTGTAGCCTGGTATCAACAAAAACCAGGGCAATCT<br>CCTAAACTACTGATTTACTGGGCATCCACCCGGCACACTGGAG<br>TCCCTGATCGCTTCACAGGCAGTGGATCTGGGACAGATTATAC<br>TCTCACCATCAGCAGTGTGCAGGCTGAAGACCTGGCACTTTAT<br>TACTGTCAGCAACATTATAACACTCCTCCCACGTTCGGCTCGG<br>GGACAAAGTTGGAAATAAAA (SEQ ID NO: 42) |

Example 3: Epitope Mapping of Mouse Anti-Ang2 Antibody Against hAng2

The antigenic determinants (epitopes) of hAng2 recognized by mouse monoclonal antibodies, 2C8 and 4B9, were analyzed by HDX-MS (Hydrogen/deuterium exchange-mass spectrometry) technique. HDX-MS analysis methods are described in the following articles; Houde D, Engen J R (2013) Methods Mol. Biol. 988: 269-89 and Houde et al. (2011) J. Pharm. Sci. 100 (6), 2071.

Recombinant hAng2-RBD protein was used to analyze the epitopes of antibodies 2C8 and 4B9. Before deuterium labeling reaction, hAng2-RBD/antibody mixtures were incubated for more than 3 hrs to be maintained to the maximum binding (100%) under 15× diluted deuterium labeling buffer ($K_D$=25 nM). The prepared hAng2-RBD/antibody complexes were diluted 15 times with deuterium labeling buffer, labeled at various time, and then quenched with the same volume of quenching buffer. The labeling reaction time was 0 min (undeuterium), 0.33 min, 10 min, 60 min and 240 min. However, in undeuterium condition, the deuterium labeling buffer was replaced with equilibrium buffer and the reaction was immediately stopped with quenching buffer. For mass spectrometry, the deuterium labeled hAng2-RBD/antibody samples were loaded on a pepsin column and peptide digestion was proceeded. Mass spectrometry analysis showed that 13 peptides at the N-terminal of hAng2-RBD and peptic peptides corresponding to 25-40 amino acids were not detected at all, and 83.7% coverage data was obtained from a total of peptic peptides.

The deuterium uptake difference between hAng2-RBD alone and the hAng2-RBD-antibody complex conditions was comparatively analyzed, and a region showing a distinct decrease in the deuterium uptake is either a peptide to which the antibody binds directly, or a structurally changed region. When the deuterium uptake difference between hAng2-RBD alone and the hAng2-RBD-antibody complex was 0.5-1 Da or more, it was considered significant.

Figure 2:
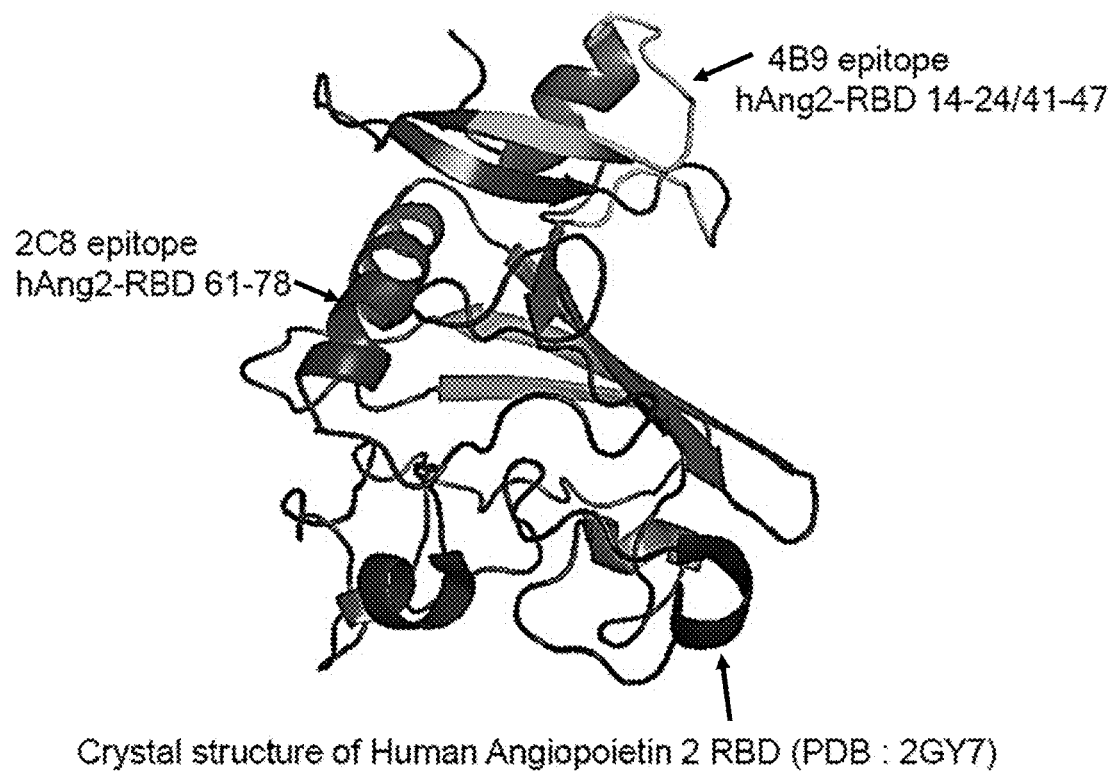
FIG. 2. Schematic showing epitopes of anti-Ang2 antibodies, which were analyzed by hydrogen/deuterium exchange-mass spectrometry. Recombinant hAng2-RBD alone or hAng2-RBD/Ang2-antibody complex was labeled with deuterium. The labeled proteins were digested in pepsin column and were analyzed by mass spectrometry. The deuterium uptake of hAng2-RBD alone and hAng2-RBD/Ang-2 antibody complex was analyzed and the difference in deuterium uptake was compared. A peptide with mass difference over 0.5-1 Da in deuterium uptake was determined to be a specific epitope which mediate the binding to anti-Ang2 antibodies. 2C8 epitope and 4B9 epitope were visualized in the image of Ang2-RBD crystal structure (PDB:2GY7) which was generated using PyMol software.

Analysis of the deuterium uptake difference indicated that the epitope to which antibody 2C8 binds is residues 61 to 78 of SEQ ID NO: 2—QRTWKEYKVGFGNPSGEY (SEQ ID NO: 115) of hAng2-RBD (Table 11), and the epitope to which antibody 4B9 binds is residues 14 to 24 of SEQ ID NO: 2—KSGHTTNGIYT (SEQ ID NO: 116) and residues 41 to 47 of SEQ ID NO: 2—EAGGGGW (SEQ ID NO: 117) (Table 12). In the case of antibody 4B9, it cannot be ruled out that an undetermined region (residues 25 to 40 of SEQ ID NO: 2) can be included in the scope of the epitope. The epitope analysis results for each antibody are shown in different colors on the 3D structure of hAng2-RBD, which was generated using PyMol software (FIG. 2).

TABLE 11

Epitope mapping analysis for 2C8 binding to hAng2 by HDX-MS
2C8 binding to hAng2-RBD

| Residues (SEQ ID NO: 2) | Exposure Time (min) | Relative Uptake (Da) | | |
|---|---|---|---|---|
| | | hAng2-RBD alone | hAng2-RBD + 2C8 | Δ |
| 52-60 | 0.00 | 0.79 | 0.64 | 0.15 |
| 52-60 | 0.33 | 1.36 | 1.14 | 0.21 |
| 52-60 | 10.00 | 1.92 | 1.51 | 0.41 |
| 52-60 | 60.00 | 2.10 | 1.96 | 0.14 |
| 52-60 | 240.00 | 2.35 | 2.28 | 0.08 |
| 61-77 | 0.00 | 1.23 | 1.15 | 0.08 |
| 61-77* | 0.33 | 2.93 | 1.75 | 1.18 |
| 61-77* | 10.00 | 4.71 | 2.93 | 1.78 |
| 61-77* | 60.00 | 5.16 | 3.80 | 1.36 |
| 61-77* | 240.00 | 5.53 | 4.22 | 1.31 |
| 61-78 | 0.00 | 1.27 | 1.21 | 0.06 |
| 61-78* | 0.33 | 3.01 | 1.87 | 1.15 |
| 61-78* | 10.00 | 4.77 | 2.97 | 1.80 |
| 61-78* | 60.00 | 5.22 | 3.90 | 1.33 |
| 61-78* | 240.00 | 5.59 | 4.25 | 1.34 |
| 67-77 | 0.00 | 0.85 | 0.96 | −0.12 |
| 67-77* | 0.33 | 2.13 | 1.24 | 0.89 |
| 67-77* | 10.00 | 3.09 | 1.51 | 1.58 |
| 67-77* | 60.00 | 3.26 | 2.05 | 1.21 |
| 67-77* | 240.00 | 3.53 | 2.46 | 1.07 |
| 67-78 | 0.00 | 1.12 | 0.82 | 0.30 |
| 67-78* | 0.33 | 2.39 | 1.44 | 0.95 |
| 67-78* | 10.00 | 3.30 | 1.64 | 1.66 |
| 67-78* | 60.00 | 3.48 | 2.15 | 1.33 |
| 67-78* | 240.00 | 3.72 | 2.68 | 1.04 |
| 78-84 | 0.00 | 0.59 | 0.59 | 0.00 |
| 78-84 | 0.33 | 0.69 | 0.70 | −0.01 |
| 78-84 | 10.00 | 0.71 | 0.69 | 0.01 |
| 78-84 | 60.00 | 0.83 | 0.73 | 0.11 |
| 78-84 | 240.00 | 1.07 | 0.72 | 0.36 |

TABLE 12

Epitope mapping analysis for 4B9 binding to hAng2 by HDX-MS
4B9 binding to hAng2-RBD

| Residues (SEQ ID NO: 2) | Exposure Time (min) | Relative Uptake (Da) | | |
|---|---|---|---|---|
| | | hAng2-RBD alone | hAng2-RBD + 4B9 | Δ |
| 14-23 | 0.00 | 0.80 | 0.55 | 0.25 |
| 14-23* | 0.33 | 1.31 | 0.97 | 0.34 |
| 14-23* | 10.00 | 2.21 | 1.38 | 0.83 |
| 14-23* | 60.00 | 2.27 | 1.49 | 0.78 |
| 14-23* | 240.00 | 2.26 | 1.66 | 0.60 |
| 14-24 | 0.00 | 0.77 | 0.76 | 0.01 |
| 14-24* | 0.33 | 1.59 | 1.27 | 0.33 |
| 14-24* | 10.00 | 3.25 | 1.75 | 1.50 |
| 14-24* | 60.00 | 3.40 | 2.05 | 1.35 |
| 14-24* | 240.00 | 3.41 | 2.61 | 0.80 |
| 41-47 | 0.00 | 0.30 | 0.16 | 0.15 |
| 41-47* | 0.33 | 1.22 | 0.20 | 1.02 |
| 41-47* | 10.00 | 1.35 | 0.43 | 0.92 |
| 41-47* | 60.00 | 1.69 | 0.54 | 1.15 |
| 41-47* | 240.00 | 1.80 | 0.61 | 1.18 |
| 47-60 | 0.00 | 1.01 | 0.96 | 0.05 |
| 47-60 | 0.33 | 1.81 | 1.94 | −0.13 |
| 47-60 | 10.00 | 2.47 | 2.53 | −0.06 |
| 47-60 | 60.00 | 2.68 | 2.69 | −0.01 |
| 47-60 | 240.00 | 2.95 | 3.06 | −0.11 |

Example 4: Humanization of Mouse Anti-Ang2 Antibody and Full-Length IgG Conversion To eliminate the immunogenicity of mouse anti-Ang2 antibodies 2C8 and 4B9 when administered into human, the antibodies were humanized as follows.

4-1: Heavy Chain Humanization

The human antibody heavy chain variable gene showing 64% homology to the heavy chain sequence of antibody 2C8 was IGHV1-46-01. Based on these analysis, the CDR region of the 2C8 antibody was transplanted into the human antibody heavy chain variable gene IGHV1-46-01. In this process, 5 humanized heavy chain antibody genes were designed (Table 13). Back mutations to mouse sequence were introduced in heavy chain genes of humanized 2C8, indicated as bold in protein sequence of Table 13.

The human antibody heavy chain variable gene showing 80% homology to the heavy chain sequence of antibody 4B9 was IGHV3-11-01. Based on the analysis, the CDR region of the 4B9 antibody was transplanted into the human antibody heavy chain variable gene IGHV3-11-01. As the result, 3 humanized heavy chain antibody genes were designed in this process (Table 13). Back mutations to mouse sequence were introduced in heavy chain genes of humanized 4B9, indicated as bold in protein sequence of Table 13.

4-2: Light Chain Humanization

The human antibody light chain variable gene showing homology of 67% to the light chain sequence of antibody 2C8 was IGKV1-9-01. Based on these analyses, the CDR region of 2C8 antibody was transplanted into the human antibody light chain variable gene IGKV1-9-01. 3 humanized light chain antibody genes were designed in this process (Table 13). Back mutations to mouse sequence were introduced in light chain genes of humanized 2C8, indicated as bold in protein sequence of Table 13.

The human antibody light chain variable gene showing 70% homology to the light chain sequence of antibody 4B9 was IGKV1-39-01. Based on these analyses, the CDR region of 4B9 antibody was transplanted into the human antibody light chain variable gene IGKV1-39-01. 1 humanized light chain antibody gene was designed in this process (Table 13).

4-3: Humanized Gene Synthesis and Cloning to Human Full-Length IgG Antibody

The humanized variable regions of antibodies in Table 15 were incorporated into the heavy chain and the light chain vector of the human IgG1 antibody. Coding nucleotides corresponding to the humanized heavy chain variable region of the antibodies (VH) were synthesized by Bioneer, Inc. so as to consist of 'EcoRI-signal sequence-VH-NheI—CH-XhoI'. Coding nucleotides corresponding the humanized light chain variable region of the antibodies (VL) were synthesized by Bioneer, Inc. so as to consist of 'EcoRI-signal sequence-VL-BsiWI-CL-XhoI'. The polynucleotides encoding the heavy chain were respectively cloned into a vector of pOptiVEC™-TOPO™ TA Cloning™ Kit (for TOPO® Cloning of PCR products into a bicistronic vector) included in OptiCHO™ Antibody Express Kit (Invitrogen, designed for efficient growth and transfection of dihydrofolate reductase-deficient (DHFR) Chinese hamster ovary (CHO) DG44 cells in suspension culture), and the polynucleotides encoding the light chain were respectively cloned into a vector of pcDNA™3.3-TOPO™ TA CloningIM Kit (Invitrogen, TOPO™-adapted plasmid vector, all reagents for cloning, and One Shot™ TOP10 competent cells), using EcoRI and XhoI to establish vectors for expressing full-length human IgG antibodies. For construction of human IgG4 class antibody of 2C8H11 and 4B9H11, each named 2C8H11G4 and 4B9H11G4, the constant regions (CH1-hinge-CH2-CH3) of 2C8H11 heavy chain gene and 4B9 heavy chain gene were replaced by the polynucleotide encoding IgG4 class heavy chain constant region.

TABLE 13

Humanized anti-Ang2 antibodies originated from mouse 4B9 and 2C8 antibodies

| Antibody | Antibody Sequence (VH) | Antibody Sequence (VL) |
|---|---|---|
| 4B9H11 | (Protein Sequence)<br>QVQLVESGGGLVKPGGSLRL<br>SCAASGFTFSDYYMYWIRQA<br>PGKGLEWVSTISVGGSFTYY<br>PDSVKGRFTISRDNAKNSLYL<br>QMNSLRAEDTAVYYCARDW<br>GLRPWFVYWGQGTLVTVSS<br>(SEQ ID NO: 43)<br>(Coding Nucleotide Sequence)<br>CAGGTACAGCTCGTGGAGT<br>CTGGTGGAGGCTTGGTGAA<br>ACCTGGAGGGTCCCTGAGA<br>CTTAGCTGTGCAGCTTCCG<br>GCTTCACATTTTCAGACTATT<br>ATATGTATTGGATCAGACAG<br>GCTCCCGGGAAGGGCTTGG<br>AGTGGGTTTCAACCATTAGT<br>GTTGGCGGATCTTTTACTTA<br>CTACCCAGACAGTGTGAAG<br>GGGAGATTCACAATCTCCAG<br>GGATAACGCGAAAAACAGC<br>CTGTATCTCCAAATGAATAG<br>CCTGAGAGCCGAAGATACC<br>GCCGTGTACTACTGCGCCA<br>GAGACTGGGGATTACGGCC<br>CTGGTTCGTGTACTGGGGC<br>CAGGGAACCCTGGTCACCG<br>TCTCCTCA<br>(SEQ ID NO: 45) | (Protein Sequence)<br>DIQMTQSPSSLSASVGDRVTI<br>TCKASQDVSTAVAWYQQKPG<br>KAPKLLIYWASTRHTGVPSRF<br>SGSGSGTDFTLTISSLQPEDF<br>ATYYCQQHYSTPPTFGQGTK<br>VEIK<br>(SEQ ID NO: 44)<br>(Coding Nucleotide Sequence)<br>GACATCCAGATGACACAGTC<br>CCCAAGCTCCCTGTCTGCAT<br>CTGTGGGAGACCGGGTGAC<br>CATCACTTGTAAGGCCTCAC<br>AGGATGTTTCTACTGCTGTC<br>GCATGGTACCAGCAAAAGC<br>CGGGTAAAGCTCCCAAGCT<br>TTTGATATACTGGGCCAGCA<br>CCAGGCACACAGGCGTGCC<br>ATCAAGATTCAGTGGGTCCG<br>GATCCGGCACGGATTTTACA<br>CTCACTATTAGCTCACTGCA<br>ACCTGAAGACTTTGCCACCT<br>ATTACTGCCAGCAGCATTATA<br>GCACCCCTCCCACCTTCGG<br>TCAGGGCACTAAAGTAGAAA<br>TCAAA<br>(SEQ ID NO: 46) |
| 4B9H21 | (Protein Sequence)<br>QVQLVESGGGLVKPGGSLRL<br>SCAASGFTFSDYYMYWVRQ<br>APGKGLEWVSTISVGGSFTY<br>YPDSVKGRFTISRDNAKNSLY<br>LQMNSLRAEDTAVYYCARDW<br>GLRPWFVYWGQGTLVTVSS<br>(SEQ ID NO: 47)<br>(Coding Nucleotide Sequence)<br>CAGGTCCAGCTGGTGGAAT<br>CCGGCGGAGGCTTGGTGAA<br>GCCTGGAGGCAGCCTAAGA<br>CTCTCCTGTGCAGCCTCTG<br>GCTTCACCTTCTCTGACTAT<br>TACATGTATTGGGTCCGCCA<br>GGCTCCAGGGAAGGGCTC<br>GAGTGGGTTTCAACAATTAG<br>TGTAGGTGGAAGCTTCACCT<br>ACTATCCTGACTCCGTGAAA<br>GGAAGATTTACGATCTCTAG<br>GGATAATGCCAAGAACTCAC<br>TGTACCTTCAGATGAACAGC<br>CTGAGAGCGGAGGACACAG | (Protein Sequence)<br>DIQMTQSPSSLSASVGDRVTI<br>TCKASQDVSTAVAWYQQKPG<br>KAPKLLIYWASTRHTGVPSRF<br>SGSGSGTDFTLTISSLQPEDF<br>ATYYCQQHYSTPPTFGQGTK<br>VEIK<br>(SEQ ID NO: 48)<br>(Coding Nucleotide Sequence)<br>GACATCCAGATGACACAGTC<br>CCCAAGCTCCCTGTCTGCAT<br>CTGTGGGAGACCGGGTGAC<br>CATCACTTGTAAGGCCTCAC<br>AGGATGTTTCTACTGCTGTC<br>GCATGGTACCAGCAAAAGC<br>CGGGTAAAGCTCCCAAGCT<br>TTTGATATACTGGGCCAGCA<br>CCAGGCACACAGGCGTGCC<br>ATCAAGATTCAGTGGGTCCG<br>GATCCGGCACGGATTTTACA<br>CTCACTATTAGCTCACTGCA<br>ACCTGAAGACTTTGCCACCT<br>ATTACTGCCAGCAGCATTATA |

TABLE 13-continued

Humanized anti-Ang2 antibodies originated from mouse 4B9 and 2C8 antibodies

| Antibody | Antibody Sequence (VH) | Antibody Sequence (VL) |
|---|---|---|
| | CCGTGTACTACTGCGCTAGA<br>GATTGGGGATTAAGACCCTG<br>GTTTGTTTATTGGGGCCAGG<br>GAACCCTGGTCACCGTCTC<br>CTCA<br>(SEQ ID NO: 49) | GCACCCCTCCCACCTTCGG<br>TCAGGGCACTAAAGTAGAAA<br>TCAAA<br>(SEQ ID NO: 50) |
| 4B9H31 | (Protein Sequence)<br>QVQLVESGGGLVKPGGSLRL<br>SCAASGFTFSDYYMYWVRQ<br>APGKGLEWVA<u>TISVGGSFTY<br>YPDSVKGRFTISRDNAKNSLY<br>LQMNSLRAEDTAVYYCARDW<br>GLRPWFVYWGQGTLVTVSS</u><br>(SEQ ID NO: 51)<br>(Coding Nucleotide Sequence)<br>CAGGTGCAGCTGGTCGAAT<br>CTGGAGGAGGCTTGGTGAA<br>ACCTGGGGGTCCCTGAGA<br>CTCTCTTGTGCAGCCTCCG<br>GCTTTACCTTTTCTGACTACT<br>ACATGTATTGGGTTCGCCAG<br>GCTCCCGGTAAGGGGTTAG<br>AGTGGGTGGCTACCATTAGT<br>GTTGGCGGTTCATTTACTTA<br>TTACCCAGATAGTGTGAAAG<br>GACGGTTCACCATCAGCAG<br>GGACAATGCAAAGAACTCA<br>CTCTATCTACAAATGAATAGC<br>CTGAGAGCCGAGGATACAG<br>CGGTGTATTACTGCGCCAGA<br>GATTGGGGACTTCGACCAT<br>GGTTCGTCTACTGGGGCCA<br>GGGAACCCTGGTCACCGTC<br>TCCTCA<br>(SEQ ID NO: 53) | (Protein Sequence)<br>DIQMTQSPSSLSASVGDRVTI<br>TCKAS<u>Q</u>DVSTAVAWYQQKPG<br>KAPKLLIYWASTRHTGVPSRF<br>SGSGSGTDFTLTISSLQPEDF<br>ATYYC<u>QQ</u>HYSTPPTFGQGTK<br>VEIK<br>(SEQ ID NO: 52)<br>(Coding Nucleotide Sequence)<br>GACATCCAGATGACACAGTC<br>CCCAAGCTCCCTGTCTGCAT<br>CTGTGGGAGACCGGGTGAC<br>CATCACTTGTAAGGCCTCAC<br>AGGATGTTTCTACTGCTGTC<br>GCATGGTACCAGCAAAAGC<br>CGGGTAAAGCTCCCAAGCT<br>TTTGATATACTGGGCCAGCA<br>CCAGGCACACAGGCGTGCC<br>ATCAAGATTCAGTGGGTCCG<br>GATCCGGCACGGATTTTACA<br>CTCACTATTAGCTCACTGCA<br>ACCTGAAGACTTTGCCACCT<br>ATTACTGCCAGCAGCATTATA<br>GCACCCCTCCCACCTTCGG<br>TCAGGGCACTAAAGTAGAAA<br>TCAAA<br>(SEQ ID NO: 54) |
| 2C8H11 | (Protein Sequence)<br>QVQLVQSGAEVKKPGASVKV<br>SCKASGYTFTSYWMHWVRQ<br>APGQGLEWVG<u>MIDPSDSET<br>RLNQKFKDRVTMTRDTSTST<br>VYMELSSLRSEDTAVYYCAR<br>RFYYGSDWYFDV</u>WGQGTLV<br>TVSS<br>(SEQ ID NO: 55)<br>(Coding Nucleotide Sequence)<br>CAGGTGCAGCTGGTGCAGA<br>GTGGAGCTGAGGTAAAAAA<br>GCCCGGCGCCAGTGTGAAG<br>GTTAGTTGCAAGGCCTCTG<br>GATACACCTTCACAAGCTAT<br>TGGATGCACTGGGTGCGAC<br>AAGCTCCTGGGCAGGGGCT<br>TGAGTGGATGGGAATGATC<br>GACCCATCCGATTCAGAAAC<br>TAGGCTCAACCAGAAATTCA<br>AAGATAGAGTGACTATGACC<br>AGGGACACCTCCACGAGCA<br>CAGTCTACATGGAATTGTCA<br>AGCCTGCGCTCTGAGGACA<br>CAGCCGTGTACTATTGTGCA<br>AGACGGTTTTACTATGGTAG<br>CGATTGGTACTTTGATGTTT<br>GGGGCCAGGGAACCCTGGT<br>CACCGTCTCCTCA<br>(SEQ ID NO: 57) | (Protein Sequence)<br>DIQLTQSPSFLSASVGDRVTIT<br>CKAS<u>Q</u>DVGTAVAWYQQKPG<br>KAPKLLIYWASTRHTGVPSRF<br>SGSGSGTEFTLTISSLQPEDF<br>ATYYC<u>QQ</u>YSSYPLTFGQGTK<br>VEIK<br>(SEQ ID NO: 56)<br>(Coding Nucleotide Sequence)<br>GACATACAGTTGACCCAGTC<br>TCCTTCCTTCCTGTCCGCCT<br>CCGTGGGCGATAGAGTTAC<br>CATTACTTGCAAAGCTAGTC<br>AGGACGTGGGTACCGCAGT<br>GGCCTGGTATCAGCAGAAA<br>CCAGGTAAAGCCCCTAAGCT<br>CCTGATCTACTGGGCATCAA<br>CACGGCACAGGGGTCCC<br>AAGCAGGTTTTCTGGCAGC<br>GGATCAGGAACCGAATTTAC<br>ACTGACGATCTCGTCTCTGC<br>AGCCCGAGGATTCGCTACT<br>TACTACTGTCAACAATATAGT<br>AGCTATCCCCTCACTTTCGG<br>TCAGGGCACTAAAGTAGAAA<br>TCAAA<br>(SEQ ID NO: 58) |
| 2C8H21 | (Protein Sequence)<br>QVQLVQSGAEVKKPGASVKV<br>SCKASGYSFTSYWMHWVRQ<br>APGQGLEWIG<u>MIDPSDSETR<br>LNQKFKDRVTMTRDTSTSTV<br>YMELSSLRSEDTAVYYCAR<u>R</u></u> | (Protein Sequence)<br>DIQLTQSPSFLSASVGDRVTIT<br>CKAS<u>Q</u>DVGTAVAWYQQKPG<br>KAPKLLIYWASTRHTGVPSRF<br>SGSGSGTEFTLTISSLQPEDF<br>ATYYC<u>QQ</u>YSSYPLTFGQGTK |

TABLE 13-continued

Humanized anti-Ang2 antibodies originated from mouse 4B9 and 2C8 antibodies

| Antibody | Antibody Sequence (VH) | Antibody Sequence (VL) |
|---|---|---|
| | FYYGSDWYFDVWGQGTLVT VSS (SEQ ID NO: 59) (Coding Nucleotide Sequence) CAGGTGCAACTCGTGCAGT CTGGAGCTGAAGTGAAGAA ACCCGGGGCCTCAGTGAAG GTGAGTTGCAAAGCATCTG GGTACTCATTTACCAGCTATT GGATGCACTGGGTGCGGCA GGCCCCAGGACAAGGCCTG GAGTGGATTGGCATGATCGA CCCTTCCGATAGTGAAACGA GGCTGAACCAGAAGTTTAAA GATCGCGTCACCATGACCA GGGACACAAGTACTTCTACA GTCTACATGGAGTTGAGCAG CCTGAGATCAGAGGACACA GCCGTTTACTACTGTGCTAG ACGATTCTATTATGGCAGCG ACTGGTATTTCGATGTATGG GGCCAGGGAACCCTGGTCA CCGTCTCCTCA (SEQ ID NO: 61) | VEIK (SEQ ID NO: 60) (Coding Nucleotide Sequence) GACATACAGTTGACCCAGTC TCCTTCCTTCCTGTCCGCCT CCGTGGGCGATAGAGTTAC CATTACTTGCAAAGCTAGTC AGGACGTGGGTACCGCAGT GGCCTGGTATCAGCAGAAA CCAGGTAAAGCCCCTAAGCT CCTGATCTACTGGGCATCAA CACGGCACACAGGGGTCCC AAGCAGGTTTTCTGGCAGC GGATCAGGAACCGAATTTAC ACTGACGATCTCGTCTCTGC AGCCCGAGGATTTCGCTACT TACTACTGTCAACAATATAGT AGCTATCCCCTCACTTTCGG TCAGGGCACTAAAGTAGAAA TCAAA (SEQ ID NO: 62) |
| 2C8H31 | (Protein Sequence) QVQLVQSGAEVKKPGASVKV SCKASGYSFTSYWMHWVRQ APGQGLEWIGMIDPSDSETR LNQKFKDKASMTRDTSTSTV YMELSSLRSEDTAVYYCARR FYYGSDWYFDVWGQGTLVT VSS (SEQ ID NO: 63) (Coding Nucleotide Sequence) CAGGTGCAACTGGTGCAGT CTGGTGCTGAGGTGAAGAA ACCAGGCGCTTCAGTCAAG GTAAGCTGCAAAGCAAGTG GATACTCCTTCACCTCTTATT GGATGCACTGGGTTAGACA GGCCCCTGGTCAAGGCCTC GAGTGGATTGGCATGATCGA CCCCTCTGACAGCGAAACT AGGCTGAATCAGAAATTTAA GGACAAGGCCTCCATGACA CGGGATACATCCACAAGCAC CGTTTACATGGAACTGAGCT CGCTGAGAAGTGAGGACAC TGCCGTGTATTACTGTGCGA GACGCTTTTATTACGGGTCA GATTGGTACTTCGATGTGTG GGGCCAGGGAACCCTGGTC ACCGTCTCCTCA (SEQ ID NO: 65) | (Protein Sequence) DIQLTQSPSFLSASVGDRVTIT CKASQDVGTAVAWYQQKPG KAPKLLIYWASTRHTGVPSRF SGSGSGTEFTLTISSLQPEDF ATYYCQQYSSYPLTFGQGTK VEIK (SEQ ID NO: 64) (Coding Nucleotide Sequence) GACATACAGTTGACCCAGTC TCCTTCCTTCCTGTCCGCCT CCGTGGGCGATAGAGTTAC CATTACTTGCAAAGCTAGTC AGGACGTGGGTACCGCAGT GGCCTGGTATCAGCAGAAA CCAGGTAAAGCCCCTAAGCT CCTGATCTACTGGGCATCAA CACGGCACACAGGGGTCCC AAGCAGGTTTTCTGGCAGC GGATCAGGAACCGAATTTAC ACTGACGATCTCGTCTCTGC AGCCCGAGGATTTCGCTACT TACTACTGTCAACAATATAGT AGCTATCCCCTCACTTTCGG TCAGGGCACTAAAGTAGAAA TCAAA (SEQ ID NO: 66) |
| 2C8H41 | (Protein Sequence) QVQLVQSGAEVKKPGASVKV SCKASGYSFTSYWMHWVKQ APGQGLEWIGMIDPSDSETR LNQKFKDKASMTRDTSTSTV YMELSSLRSEDTAVYYCARR FYYGSDWYFDVWGQGTLVT VSS (SEQ ID NO: 67) (Coding Nucleotide Sequence) CAGGTGCAGCTGGTGCAGT CTGGGGCTGAGGTGAAAAA GCCAGGCGCTTCCGTCAAA GTTTCCTGCAAGGCATCTG GTTACTCTTTTACAAGCTATT GGATGCACTGGGTGAAGCA GGCCCCCGGACAAGGGCTC GAGTGGATTGGCATGATCGA TCCTTCCGATAGTGAAACAC | (Protein Sequence) DIQLTQSPSFLSASVGDRVTIT CKASQDVGTAVAWYQQKPG KAPKLLIYWASTRHTGVPSRF SGSGSGTEFTLTISSLQPEDF ATYYCQQYSSYPLTFGQGTK VEIK (SEQ ID NO: 68) (Coding Nucleotide Sequence) GACATACAGTTGACCCAGTC TCCTTCCTTCCTGTCCGCCT CCGTGGGCGATAGAGTTAC CATTACTTGCAAAGCTAGTC AGGACGTGGGTACCGCAGT GGCCTGGTATCAGCAGAAA CCAGGTAAAGCCCCTAAGCT CCTGATCTACTGGGCATCAA CACGGCACACAGGGGTCCC |

TABLE 13-continued

Humanized anti-Ang2 antibodies originated from mouse 4B9 and 2C8 antibodies

| Antibody | Antibody Sequence (VH) | Antibody Sequence (VL) |
|---|---|---|
| | GCTTGAATCAGAAATTCAAG<br>GACAAGGCCAGTATGACCA<br>GGGATACTAGCACAAGCACT<br>GTATATATGGAGCTTAGCTCA<br>CTGAGATCAGAAGACACGG<br>CCGTGTACTACTGTGCGAGA<br>CGGTTTTACTATGGCTCCGA<br>CTGGTATTTCGACGTCTGGG<br>GCCAGGGAACCCTGGTCAC<br>CGTCTCCTCA<br>(SEQ ID NO: 69) | AAGCAGGTTTTCTGGCAGC<br>GGATCAGGAACCGAATTTAC<br>ACTGACGATCTCGTCTCTGC<br>AGCCCGAGGATTTCGCTACT<br>TACTACTGTCAACAATATAGT<br>AGCTATCCCCTCACTTTCGG<br>TCAGGGCACTAAAGTAGAAA<br>TCAAA<br>(SEQ ID NO: 70) |
| 2C8H51 | (Protein Sequence)<br>QVQLVQSGAEVKKPGASVKV<br>SCKASGYSFTSYWMHWVKQ<br>APGQGLEWIGMIDPSDSETR<br>LNQKFKDKASLTVDTSTSTV<br>YMELSSLRSEDTAVYYCARR<br>FYYGSDWYFDVWGQGTLVT<br>VSS<br>(SEQ ID NO: 71)<br>(Coding Nucleotide Sequence)<br>CAGGTGCAGCTGGTGCAGT<br>CTGGCGCTGAGGTGAAGAA<br>ACCTGGGGCCTCAGTGAAG<br>GTTTCCTGTAAAGCAAGTGG<br>ATACTCTTTCACCAGCTACT<br>GGATGCACTGGGTGAAACA<br>GGCCCCCGGCCAAGGGCTT<br>GAGTGGATTGGTATGATCGA<br>TCCATCCGACAGCGAAACTA<br>GGCTCAACCAGAAGTTCAA<br>GGATAAAGCGTCCTTGACAG<br>TAGATACATCCACGAGCACA<br>GTTTATATGGAGCTGTCTAG<br>TCTGCGGTCTGAAGACACC<br>GCCGTGTATTATTGCGCTAG<br>ACGCTTTTATTACGGCTCGG<br>ACTGGTACTTTGACGTCTGG<br>GGCCAGGGAACCCTGGTCA<br>CCGTCTCCTCA<br>(SEQ ID NO: 73) | (Protein Sequence)<br>DIQLTQSPSFLSASVGDRVTIT<br>CKASQDVGTAVAWYQQKPG<br>KAPKLLIYWASTRHTGVPSRF<br>SGSGSGTEFTLTISSLQPEDF<br>ATYYCQQYSSYPLTFGQGTK<br>VEIK<br>(SEQ ID NO: 72)<br>(Coding Nucleotide Sequence)<br>GACATACAGTTGACCCAGTC<br>TCCTTCCTTCCTGTCCGCCT<br>CCGTGGGCGATAGAGTTAC<br>CATTACTTGCAAAGCTAGTC<br>AGGACGTGGGTACCGCAGT<br>GGCCTGGTATCAGCAGAAA<br>CCAGGTAAAGCCCCTAAGCT<br>CCTGATCTACTGGGCATCAA<br>CACGGCACACAGGGGTCCC<br>AAGCAGGTTTTCTGGCAGC<br>GGATCAGGAACCGAATTTAC<br>ACTGACGATCTCGTCTCTGC<br>AGCCCGAGGATTTCGCTACT<br>TACTACTGTCAACAATATAGT<br>AGCTATCCCCTCACTTTCGG<br>TCAGGGCACTAAAGTAGAAA<br>TCAAA<br>(SEQ ID NO: 74) |
| 2C8H12 | (Protein Sequence)<br>QVQLVQSGAEVKKPGASVKV<br>SCKASGYTFTSYWMHWVRQ<br>APGQGLEWMGMIDPSDSET<br>RLNQKFKDRVTMTRDTSTST<br>VYMELSSLRSEDTAVYYCAR<br>RFYYGSDWYFDVWGQGTLV<br>TVSS<br>(SEQ ID NO: 75)<br>(Coding Nucleotide Sequence)<br>CAGGTGCAGCTGGTGCAGA<br>GTGGAGCTGAGGTAAAAAA<br>GCCCGGCGCCAGTGTGAAG<br>GTTAGTTGCAAGGCCTCTG<br>GATACACCTTCACAAGCTAT<br>TGGATGCACTGGGTGCGAC<br>AAGCTCCTGGGCAGGGGCT<br>TGAGTGGATGGGAATGATC<br>GACCCATCCGATTCAGAAAC<br>TAGGCTCAACCAGAAATTCA<br>AAGATAGAGTGACTATGACC<br>AGGGACACCTCCACGAGCA<br>CAGTCTACATGGAATTGTCA<br>AGCCTGCGCTCTGAGGACA<br>CAGCCGTGTACTATTGTGCA<br>AGACGGTTTTACTATGGTAG<br>CGATTGGTACTTTGATGTTT<br>GGGGCCAGGGAACCCTGGT<br>CACCGTCTCCTCA<br>(SEQ ID NO: 77) | (Protein Sequence)<br>DIQLTQSPSFLSASVGDRVSI<br>TCKASQDVGTAVAWYQQKP<br>GKAPKLLIYWASTRHTGVPD<br>RFSGSGSGTEFTLTISSLQPE<br>DFATYYCQQYSSYPLTFGQG<br>TKVEIK<br>(SEQ ID NO: 76)<br>(Coding Nucleotide Sequence)<br>GATATTCAACTCACCCAGAG<br>TCCATCCTTCCTGTCTGCCT<br>CAGTGGGCGACAGAGTGTC<br>AATCACATGCAAGGCAAGCC<br>AGGATGTTGGCACTGCTGT<br>GGCTTGGTATCAGCAAAAAC<br>CAGGTAAGGCCCCCAAACT<br>GCTTATTTACTGGGCATCAA<br>CCCGGCACACGGGTGTCCC<br>CGACAGGTTCAGCGGCAGT<br>GGATCTGGGACAGAGTTTAC<br>CCTGACTATCAGCTCCCTGC<br>AGCCTGAAGACTTTGCCACT<br>TATTACTGTCAGCAGTACTCT<br>AGCTATCCTCTCACCTTCGG<br>TCAGGGCACTAAAGTAGAAA<br>TCAAA<br>(SEQ ID NO: 78) |

TABLE 13-continued

Humanized anti-Ang2 antibodies originated from mouse 4B9 and 2C8 antibodies

| Antibody | Antibody Sequence (VH) | Antibody Sequence (VL) |
|---|---|---|
| 2C8H22 | (Protein Sequence)<br>QVQLVQSGAEVKKPGASVKV<br>SCKASGYSFTSYWMHWVRQ<br>APGQGLEWIGMIDPSDSETR<br>LNQKFKDRVTMTRDTSTSTV<br>YMELSSLRSEDTAVYYCARR<br>FYYGSDWYFDVWGQGTLVT<br>VSS<br>(SEQ ID NO: 79)<br>(Coding Nucleotide Sequence)<br>CAGGTGCAACTCGTGCAGT<br>CTGGAGCTGAAGTGAAGAA<br>ACCCGGGGCCTCAGTGAAG<br>GTGAGTTGCAAAGCATCTG<br>GGTACTCATTTACCAGCTATT<br>GGATGCACTGGGTGCGGCA<br>GGCCCCAGGACAAGGCCTG<br>GAGTGGATTGGCATGATCGA<br>CCCCTTCCGATAGTGAAACGA<br>GGCTGAACCAGAAGTTTAAA<br>GATCGCGTCACCATGACCA<br>GGGACACAAGTACTTCTACA<br>GTCTACATGGAGTTGAGCAG<br>CCTGAGATCAGAGGACACA<br>GCCGTTTACTACTGTGCTAG<br>ACGATTCTATTATGGCAGCG<br>ACTGGTATTTCGATGTATGG<br>GGCCAGGGAACCCTGGTCA<br>CCGTCTCCTCA<br>(SEQ ID NO: 81) | (Protein Sequence)<br>DIQLTQSPSFLSASVGDRVSI<br>TCKASQDVGTAVAWYQQKP<br>GKAPKLLIYWASTRHTGVPD<br>RFSGSGSGTEFTLTISSLQPE<br>DFATYYCQQYSSYPLTFGQG<br>TKVEIK<br>(SEQ ID NO: 80)<br>(Coding Nucleotide Sequence)<br>GATATTCAACTCACCCAGAG<br>TCCATCCTTCCTGTCTGCCT<br>CAGTGGGCGACAGAGTGTC<br>AATCACATGCAAGGCAAGCC<br>AGGATGTTGGCACTGCTGT<br>GGCTTGGTATCAGCAAAAAC<br>CAGGTAAGGCCCCCAAACT<br>GCTTATTTACTGGGCATCAA<br>CCCGGCACACGGGTGTCCC<br>CGACAGGTTCAGCGGCAGT<br>GGATCTGGGACAGAGTTTAC<br>CCTGACTATCAGCTCCCTGC<br>AGCCTGAAGACTTTGCCACT<br>TATTACTGTCAGCAGTACTCT<br>AGCTATCCTCTCACCTTCGG<br>TCAGGGCACTAAAGTAGAAA<br>TCAAA<br>(SEQ ID NO: 82) |
| 2C8H32 | (Protein Sequence)<br>QVQLVQSGAEVKKPGASVKV<br>SCKASGYSFTSYWMHWVRQ<br>APGQGLEWIGMIDPSDSETR<br>LNQKFKDKASMTRDTSTSTV<br>YMELSSLRSEDTAVYYCARR<br>FYYGSDWYFDVWGQGTLVT<br>VSS<br>(SEQ ID NO: 83)<br>(Coding Nucleotide Sequence)<br>CAGGTGCAACTGGTGCAGT<br>CTGGTGCTGAGGTGAAGAA<br>ACCAGGCGCTTCAGTCAAG<br>GTAAGCTGCAAAGCAAGTG<br>GATACTCCTTCACCTCTTATT<br>GGATGCACTGGGTTAGACA<br>GGCCCCTGGTCAAGGCCTC<br>GAGTGGATTGGCATGATCGA<br>CCCCTCTGACAGCGAAACT<br>AGGCTGAATCAGAAATTTAA<br>GGACAAGGCCTCCATGACA<br>CGGGATACATCCACAAGCAC<br>CGTTTACATGGAACTGAGCT<br>CGCTGAGAAGTGAGGACAC<br>TGCCGTGTATTACTGTGCGA<br>GACGCTTTTATTACGGGTCA<br>GATTGGTACTTCGATGTGTG<br>GGGCCAGGGAACCCTGGTC<br>ACCGTCTCCTCA<br>(SEQ ID NO: 85) | (Protein Sequence)<br>DIQLTQSPSFLSASVGDRVSI<br>TCKASQDVGTAVAWYQQKP<br>GKAPKLLIYWASTRHTGVPD<br>RFSGSGSGTEFTLTISSLQPE<br>DFATYYCQQYSSYPLTFGQG<br>TKVEIK<br>(SEQ ID NO: 84)<br>(Coding Nucleotide Sequence)<br>GATATTCAACTCACCCAGAG<br>TCCATCCTTCCTGTCTGCCT<br>CAGTGGGCGACAGAGTGTC<br>AATCACATGCAAGGCAAGCC<br>AGGATGTTGGCACTGCTGT<br>GGCTTGGTATCAGCAAAAAC<br>CAGGTAAGGCCCCCAAACT<br>GCTTATTTACTGGGCATCAA<br>CCCGGCACACGGGTGTCCC<br>CGACAGGTTCAGCGGCAGT<br>GGATCTGGGACAGAGTTTAC<br>CCTGACTATCAGCTCCCTGC<br>AGCCTGAAGACTTTGCCACT<br>TATTACTGTCAGCAGTACTCT<br>AGCTATCCTCTCACCTTCGG<br>TCAGGGCACTAAAGTAGAAA<br>TCAAA<br>(SEQ ID NO: 86) |
| 2C8H42 | (Protein Sequence)<br>QVQLVQSGAEVKKPGASVKV<br>SCKASGYSFTSYWMHWVKQ<br>APGQGLEWIGMIDPSDSETR<br>LNQKFKDKASMTRDTSTSTV<br>YMELSSLRSEDTAVYYCARR<br>FYYGSDWYFDVWGQGTLVT<br>VSS<br>(SEQ ID NO: 87)<br>(Coding Nucleotide Sequence)<br>CAGGTGCAGCTGGTGCAGT<br>CTGGGGCTGAGGTGAAAAA | (Protein Sequence)<br>DIQLTQSPSFLSASVGDRVSI<br>TCKASQDVGTAVAWYQQKP<br>GKAPKLLIYWASTRHTGVPD<br>RFSGSGSGTEFTLTISSLQPE<br>DFATYYCQQYSSYPLTFGQG<br>TKVEIK<br>(SEQ ID NO: 88)<br>(Coding Nucleotide Sequence)<br>GATATTCAACTCACCCAGAG<br>TCCATCCTTCCTGTCTGCCT |

TABLE 13-continued

Humanized anti-Ang2 antibodies originated from mouse 4B9 and 2C8 antibodies

| Antibody | Antibody Sequence (VH) | Antibody Sequence (VL) |
|---|---|---|
| | GCCAGGCGCTTCCGTCAAA<br>GTTTCCTGCAAGGCATCTG<br>GTTACTCTTTTACAAGCTATT<br>GGATGCACTGGGTGAAGCA<br>GGCCCCCGGACAAGGGCTC<br>GAGTGGATTGGCATGATCGA<br>TCCTTCCGATAGTGAAACAC<br>GCTTGAATCAGAAAATTCAAG<br>GACAAGGCCAGTATGACCA<br>GGGATACTAGCACAAGCACT<br>GTATATATGGAGCTTAGCTCA<br>CTGAGATCAGAAGACACGG<br>CCGTGTACTACTGTGCGAGA<br>CGGTTTTACTATGGCTCCGA<br>CTGGTATTTCGACGTCTGGG<br>GCCAGGGAACCCTGGTCAC<br>CGTCTCCTCA<br>(SEQ ID NO: 89) | CAGTGGGCGACAGAGTGTC<br>AATCACATGCAAGGCAAGCC<br>AGGATGTTGGCACTGCTGT<br>GGCTTGGTATCAGCAAAAAC<br>CAGGTAAGGCCCCCAAACT<br>GCTTATTTACTGGGCATCAA<br>CCCGGCACACGGGTGTCCC<br>CGACAGGTTCAGCGGCAGT<br>GGATCTGGGACAGAGTTTAC<br>CCTGACTATCAGCTCCCTGC<br>AGCCTGAAGACTTTGCCACT<br>TATTACTGTCAGCAGTACTCT<br>AGCTATCCTCTCACCTTCGG<br>TCAGGGCACTAAAGTAGAAA<br>TCAAA<br>(SEQ ID NO: 90) |
| 2C8H52 | (Protein Sequence)<br>QVQLVQSGAEVKKPGASVKV<br>SCKASGYSFTSYWMHWVKQ<br>APGQGLEWIG<u>MIDPSDSETR<br>LNQKFKD</u>KASLTVDTSTSTV<br>YMELSSLRSEDTAVYYCARR<br><u>FYYGSDWYFDV</u>WGQGTLVT<br>VSS<br>(SEQ ID NO: 91)<br>(Coding Nucleotide Sequence)<br>CAGGTGCAGCTGGTGCAGT<br>CTGGCGCTGAGGTGAAGAA<br>ACCTGGGGCCTCAGTGAAG<br>GTTTCCTGTAAAGCAAGTGG<br>ATACTCTTTCACCAGCTACT<br>GGATGCACTGGGTGAAACA<br>GGCCCCCGGCCAAGGGCTT<br>GAGTGGATTGGTATGATCGA<br>TCCATCCGACAGCGAAACTA<br>GGCTCAACCAGAAGTTCAA<br>GGATAAAGCGTCCTTGACAG<br>TAGATACATCCACGAGCACA<br>GTTTATATGGAGCTGTCTAG<br>TCTGCGGTCTGAAGACACC<br>GCCGTGTATTATTGCGCTAG<br>ACGCTTTTATTACGGCTCGG<br>ACTGGTACTTTGACGTCTGG<br>GGCCAGGGAACCCTGGTCA<br>CCGTCTCCTCA<br>(SEQ ID NO: 93) | (Protein Sequence)<br>DIQLTQSPSFLSASVGDRVSI<br>TCKASQDVGTAVAWYQQKP<br>G<u>KAPKLLIYWASTRHTGV</u>PD<br>RFSGSGSGTEFTLTISSLQPE<br>DFATYYC<u>QQYSSYPLTF</u>GQG<br>TKVEIK<br>(SEQ ID NO: 92)<br>(Coding Nucleotide Sequence)<br>GATATTCAACTCACCCAGAG<br>TCCATCCTTCCTGTCTGCCT<br>CAGTGGGCGACAGAGTGTC<br>AATCACATGCAAGGCAAGCC<br>AGGATGTTGGCACTGCTGT<br>GGCTTGGTATCAGCAAAAAC<br>CAGGTAAGGCCCCCAAACT<br>GCTTATTTACTGGGCATCAA<br>CCCGGCACACGGGTGTCCC<br>CGACAGGTTCAGCGGCAGT<br>GGATCTGGGACAGAGTTTAC<br>CCTGACTATCAGCTCCCTGC<br>AGCCTGAAGACTTTGCCACT<br>TATTACTGTCAGCAGTACTCT<br>AGCTATCCTCTCACCTTCGG<br>TCAGGGCACTAAAGTAGAAA<br>TCAAA<br>(SEQ ID NO: 94) |
| 2C8H13 | (Protein Sequence)<br>QVQLVQSGAEVKKPGASVKV<br>SCKASGYTFTSYWMHWVRQ<br>APGQGLEWMG<u>MIDPSDSET<br>R</u>LNQKFKDRVTMTRDTSTST<br>VYMELSSLRSEDTAVYYCAR<br><u>RFYYGSDWYFDV</u>WGQGTLV<br>TVSS<br>(SEQ ID NO: 95)<br>(Coding Nucleotide Sequence)<br>CAGGTGCAGCTGGTGCAGA<br>GTGGAGCTGAGGTAAAAAA<br>GCCCGGCGCCAGTGTGAAG<br>GTTAGTTGCAAGGCCTCTG<br>GATACACCTTCACAAGCTAT<br>TGGATGCACTGGGTGCGAC<br>AAGCTCCTGGGCAGGGGCT<br>TGAGTGGATGGGAATGATC<br>GACCCATCCGATTCAGAAAC<br>TAGGCTCAACCAGAAATTCA<br>AAGATAGAGTGACTATGACC<br>AGGGACACCTCCACGAGCA<br>CAGTCTACATGGAATTGTCA<br>AGCCTGCGCTCTGAGGACA<br>CAGCCGTGTACTATTGTGCA | (Protein Sequence)<br>DIQLTQSPSFLSASVGDRVSI<br>TCKASQDVGTAVAWYQQKP<br>G<u>KAPKLLIYWASTRHTGV</u>PD<br>RFSGSGSGTEFTLTISSLQPE<br>DFADYF<u>QQYSSYPLTF</u>GQG<br>TKVEIK<br>(SEQ ID NO: 96)<br>(Coding Nucleotide Sequence)<br>GACATCCAGTTGACCCAATC<br>ACCATCCTTTCTGTCTGCCT<br>CTGTGGGAGATAGAGTCTC<br>CATTACTTGCAAGGCCAGTC<br>AGGATGTGGGGACCGCTGT<br>TGCCTGGTACCAGCAAAAA<br>CCCGGAAAGGCACCTAAAC<br>TCCTTATCTACTGGGCATCC<br>ACCCGGCACACAGGAGTGC<br>CAGACAGGTTTAGCGGGTC<br>AGGCTCTGGTACAGAGTTC<br>ACTCTGACAATTTCTAGCCT<br>GCAGCCTGAAGACTTCGCT<br>GATTATTTCTGTCAGCAGTAT<br>AGCAGTTACCCCCTCACGTT |

TABLE 13-continued

Humanized anti-Ang2 antibodies originated from mouse 4B9 and 2C8 antibodies

| Antibody | Antibody Sequence (VH) | Antibody Sequence (VL) |
|---|---|---|
| | AGACGGTTTTACTATGGTAG<br>CGATTGGTACTTTGATGTTT<br>GGGGCCAGGGAACCCTGGT<br>CACCGTCTCCTCA<br>(SEQ ID NO: 97) | CGGTCAGGGCACTAAAGTA<br>GAAATCAAA<br>(SEQ ID NO: 98) |
| 2C8H23 | (Protein Sequence)<br>QVQLVQSGAEVKKPGASVKV<br>SCKASGYSFTSYWMHWVRQ<br>APGQGLEWIGMIDPSDSETR<br>LNQKFKDRVTMTRDTSTSTV<br>YMELSSLRSEDTAVYYCARR<br>FYYGSDWYFDVWGQGTLVT<br>VSS<br>(SEQ ID NO: 99) | (Protein Sequence)<br>DIQLTQSPSFLSASVGDRVSI<br>TCKASQDVGTAVAWYQQKP<br>GKAPKLLIYWASTRHTGVPD<br>RFSGSGSGTEFTLTISSLQPE<br>DFADYFCQQYSSYPLTFGQG<br>TKVEIK<br>(SEQ ID NO: 100) |
| | (Coding Nucleotide Sequence)<br>CAGGTGCAACTCGTGCAGT<br>CTGGAGCTGAAGTGAAGAA<br>ACCCGGGGCCTCAGTGAAG<br>GTGAGTTGCAAAGCATCTG<br>GGTACTCATTTACCAGCTATT<br>GGATGCACTGGGTGCGGCA<br>GGCCCCAGGACAAGGCCTG<br>GAGTGGATTGGCATGATCGA<br>CCCTTCCGATAGTGAAACGA<br>GGCTGAACCAGAAGTTTAAA<br>GATCGCGTCACCATGACCA<br>GGGACACAAGTACTTCTACA<br>GTCTACATGGAGTTGAGCAG<br>CCTGAGATCAGAGGACACA<br>GCCGTTTACTACTGTGCTAG<br>ACGATTCTATTATGGCAGCG<br>ACTGGTATTTCGATGTATGG<br>GGCCAGGGAACCCTGGTCA<br>CCGTCTCCTCA<br>(SEQ ID NO: 101) | (Coding Nucleotide Sequence)<br>GACATCCAGTTGACCCAATC<br>ACCATCCTTTCTGTCTGCCT<br>CTGTGGGAGATAGAGTCTC<br>CATTACTTGCAAGGCCAGTC<br>AGGATGTGGGGACCGCTGT<br>TGCCTGGTACCAGCAAAAA<br>CCCGGAAAGGCACCTAAAC<br>TCCTTATCTACTGGGCATCC<br>ACCCGGCACACAGGAGTGC<br>CAGACAGGTTTAGCGGGTC<br>AGGCTCTGGTACAGAGTTC<br>ACTCTGACAATTTCTAGCCT<br>GCAGCCTGAAGACTTCGCT<br>GATTATTTCTGTCAGCAGTAT<br>AGCAGTTACCCCCTCACGTT<br>CGGTCAGGGCACTAAAGTA<br>GAAATCAAA<br>(SEQ ID NO: 102) |
| 2C8H33 | (Protein Sequence)<br>QVQLVQSGAEVKKPGASVKV<br>SCKASGYSFTSYWMHWVRQ<br>APGQGLEWIGMIDPSDSETR<br>LNQKFKDKASMTRDTSTSTV<br>YMELSSLRSEDTAVYYCARR<br>FYYGSDWYFDVWGQGTLVT<br>VSS<br>(SEQ ID NO: 103) | (Protein Sequence)<br>DIQLTQSPSFLSASVGDRVSI<br>TCKASQDVGTAVAWYQQKP<br>GKAPKLLIYWASTRHTGVPD<br>RFSGSGSGTEFTLTISSLQPE<br>DFADYFCQQYSSYPLT**FGQG<br>TKVEIK<br>(SEQ ID NO: 104) |
| | (Coding Nucleotide Sequence)<br>CAGGTGCAACTGGTGCAGT<br>CTGGTGCTGAGGTGAAGAA<br>ACCAGGCGCTTCAGTCAAG<br>GTAAGCTGCAAAGCAAGTG<br>GATACTCCTTCACCTCTTATT<br>GGATGCACTGGGTTAGACA<br>GGCCCCTGGTCAAGGCCTC<br>GAGTGGATTGGCATGATCGA<br>CCCCTCTGACAGCGAAACT<br>AGGCTGAATCAGAAATTTAA<br>GGACAAGGCCTCCATGACA<br>CGGGATACATCCACAAGCAC<br>CGTTTACATGGAACTGAGCT<br>CGCTGAGAAGTGAGGACAC<br>TGCCGTGTATTACTGTGCGA<br>GACGCTTTTATTACGGGTCA<br>GATTGGTACTTCGATGTGTG<br>GGGCCAGGGAACCCTGGTC<br>ACCGTCTCCTCA<br>(SEQ ID NO: 105) | (Coding Nucleotide Sequence)<br>GACATCCAGTTGACCCAATC<br>ACCATCCTTTCTGTCTGCCT<br>CTGTGGGAGATAGAGTCTC<br>CATTACTTGCAAGGCCAGTC<br>AGGATGTGGGGACCGCTGT<br>TGCCTGGTACCAGCAAAAA<br>CCCGGAAAGGCACCTAAAC<br>TCCTTATCTACTGGGCATCC<br>ACCCGGCACACAGGAGTGC<br>CAGACAGGTTTAGCGGGTC<br>AGGCTCTGGTACAGAGTTC<br>ACTCTGACAATTTCTAGCCT<br>GCAGCCTGAAGACTTCGCT<br>GATTATTTCTGTCAGCAGTAT<br>AGCAGTTACCCCCTCACGTT<br>CGGTCAGGGCACTAAAGTA<br>GAAATCAAA<br>(SEQ ID NO: 106) |
| 2C8H43 | (Protein Sequence)<br>QVQLVQSGAEVKKPGASVKV<br>SCKASGYSFTSYWMHWVKQ<br>APGQGLEWIGMIDPSDSETR<br>LNQKFKDKASMTRDTSTSTV<br>YMELSSLRSEDTAVYYCARR | (Protein Sequence)<br>DIQLTQSPSFLSASVGDRVSI<br>TCKASQDVGTAVAWYQQKP<br>GKAPKLLIYWASTRHTGVPD<br>RFSGSGSGTEFTLTISSLQPE<br>DFADYFCQQYSSYPLTFGQG |

TABLE 13-continued

Humanized anti-Ang2 antibodies originated from mouse 4B9 and 2C8 antibodies

| Antibody | Antibody Sequence (VH) | Antibody Sequence (VL) |
|---|---|---|
| | FYYGSDWYFDVWGQGTLVT VSS (SEQ ID NO: 107) | TKVEIK (SEQ ID NO: 108) |
| | (Coding Nucleotide Sequence) CAGGTGCAGCTGGTGCAGT CTGGGGCTGAGGTGAAAAA GCCAGGCGCTTCCGTCAAA GTTTCCTGCAAGGCATCTG GTTACTCTTTTACAAGCTATT GGATGCACTGGGTGAAGCA GGCCCCCGGACAAGGGCTC GAGTGGATTGGCATGATCGA TCCTTCCGATAGTGAAACAC GCTTGAATCAGAAATTCAAG GACAAGGCCAGTATGACCA GGGATACTAGCACAAGCACT GTATATATGGAGCTTAGCTCA CTGAGATCAGAAGACACGG CCGTGTACTACTGTGCGAGA CGGTTTTACTATGGCTCCGA CTGGTATTTCGACGTCTGGG GCCAGGGAACCCTGGTCAC CGTCTCCTCA (SEQ ID NO: 109) | (Coding Nucleotide Sequence) GACATCCAGTTGACCCAATC ACCATCCTTTCTGTCTGCCT CTGTGGGAGATAGAGTCTC CATTACTTGCAAGGCCAGTC AGGATGTGGGGACCGCTGT TGCCTGGTACCAGCAAAAA CCCGGAAAGGCACCTAAAC TCCTTATCTACTGGGCATCC ACCCGGCACACAGGAGTGC CAGACAGGTTTAGCGGGTC AGGCTCTGGTACAGAGTTC ACTCTGACAATTTCTAGCCT GCAGCCTGAAGACTTCGCT GATTATTTCTGTCAGCAGTAT AGCAGTTACCCCCTCACGTT CGGTCAGGGCACTAAAGTA GAAATCAAA (SEQ ID NO: 110) |
| 2C8H53 | (Protein Sequence) QVQLVQSGAEVKKPGASVKV SCKASGYSFTSYWMHWVKQ APGQGLEWIGMIDPSDSETR LNQKFKDKASLTVDTSTSTV YMELSSLRSEDTAVYYCARR FYYGSDWYFDVWGQGTLVT VSS (SEQ ID NO: 111) | (Protein Sequence) DIQLTQSPSFLSASVGDRVSI TCKASQDVGTAVAWYQQKP GKAPKLLIYWASTRHTGVPD RFSGSGSGTEFTLTISSLQPE DFADYFCQQYSSYPLTFGQG TKVEIK (SEQ ID NO: 112) |
| | (Coding Nucleotide Sequence) CAGGTGCAGCTGGTGCAGT CTGGCGCTGAGGTGAAGAA ACCTGGGGCCTCAGTGAAG GTTTCCTGTAAAGCAAGTGG ATACTCTTTCACCAGCTACT GGATGCACTGGGTGAAACA GGCCCCCGGCCAAGGGCTT GAGTGGATTGGTATGATCGA TCCATCCGACAGCGAAACTA GGCTCAACCAGAAGTTCAA GGATAAAGCGTCCTTGACAG TAGATACATCCACGAGCACA GTTTATATGGAGCTGTCTAG TCTGCGGTCTGAAGACACC GCCGTGTATTATTGCGCTAG ACGCTTTTATTACGGCTCGG ACTGGTACTTTGACGTCTGG GGCCAGGGAACCCTGGTCA CCGTCTCCTCA (SEQ ID NO: 113) | (Coding Nucleotide Sequence) GACATCCAGTTGACCCAATC ACCATCCTTTCTGTCTGCCT CTGTGGGAGATAGAGTCTC CATTACTTGCAAGGCCAGTC AGGATGTGGGGACCGCTGT TGCCTGGTACCAGCAAAAA CCCGGAAAGGCACCTAAAC TCCTTATCTACTGGGCATCC ACCCGGCACACAGGAGTGC CAGACAGGTTTAGCGGGTC AGGCTCTGGTACAGAGTTC ACTCTGACAATTTCTAGCCT GCAGCCTGAAGACTTCGCT GATTATTTCTGTCAGCAGTAT AGCAGTTACCCCCTCACGTT CGGTCAGGGCACTAAAGTA GAAATCAAA (SEQ ID NO: 114) |

4-4: Production and Purification of Humanized Anti-Ang2 Antibodies

To produce humanized anti-Ang2 antibodies, Expi293F™ (GibeeGIBCO™) cells (human cells are derived from the 293 cell line) capable of producing recombinant proteins with high efficiency were used. Expi293F™ cells (2×106 cells/ml) were cultured in Erlenmeyer flask, and plasmids encoding heavy chain and light chain were co-transfected into Expi293FIM cells with the ExpiFectamine™ 293 transfection kit (GIBCO™, high-efficiency, cationic, lipid-based transfection reagent and transfection enhancers are designed for high protein expression). Cells were cultured at 37° C. under 8% $CO_2$ for 5 days in a shaking incubator (orbital shaker, 125 rpm). The resulting culture medium was collected and centrifuged to remove the cells. The culture supernatant containing secreted antibodies was isolated and stored at 4° C. or immediately purified using an AKTA purification system (GE Healthcare) equipped with an affinity column (Protein A agarose column, GE Healthcare). The purified antibody was concentrated by passing it through a 0.2 μm protein centrifugal filter (AMICON®) while the solution was replaced with PBS.

Example 5: Affinity measurement of humanized anti-Ang2 antibodies against hAng2

The affinity of humanized anti-Ang2 antibody against hAng2 was measured using OCTET® system (ForteBio). Specifically, buffer and samples were measured in total 200 μl/well using Black 96-well plates (96 well F-type black plates, Greiner). The biosensor used for affinity measurements was hydrated for 10 min before measurement with AR2G tip (ForteBio OCTET®). After the hydration, humanized anti-Ang2 antibody was diluted in 10 mM sodium acetate, pH 6.0 buffer at a concentration of 10 µg/ml, fixed on AR2G biosensor, and blocked with 1M ethanolamine. The recombinant hAng2 was diluted to 50, 25, 12.5, 6.25, 3.125, and 0 nM with 1× kinetic buffer, and subjected to association for 300 sec and dissociation for 900 sec. For affinity measurement ($K_D$), association rate (K-on) and dissociation rate (K-off) were analyzed by binding curve (global) and fitted to 1:1 binding model using OCTET® data analysis v9.0.0.10 program. The $K_D$ values were shown in the following Table 14-15.

The affinities of humanized 4B9 antibodies to hAng2 were summarized in Table 14. The affinities of humanized 2C8 antibodies to hAng2 were in Table 15. In addition, IgG4 class 2C8H11G4 and 4B9H11G4 antibodies also showed subnanomolar high affinities to hAng2 antigen (Table 16).

TABLE 14

Affinities of humanized 4B9 antibodies to hAng2

| Antibody | Kon (1/Ms) | Kdis (1/s) | $K_D$ (M) |
|---|---|---|---|
| 4B9H11 | 9.29E+04 | 1.58E−06 | 1.71E−11 |
| 4B9H21 | 7.37E+04 | 8.94E−06 | 1.21E−10 |
| 4B9H31 | 9.39E+04 | 1.56E−05 | 1.67E−10 |

TABLE 15

Affinities of humanized 2C8 antibodies to hAng2

| Antibody | Kon (1/Ms) | Kdis (1/s) | $K_D$ (M) |
|---|---|---|---|
| 2C8H11 | 6.60E+04 | 1.40E−05 | 2.12E−10 |
| 2C8H21 | 1.11E+05 | 1.50E−05 | 1.35E−10 |
| 2C8H31 | 8.32E+04 | 2.21E−05 | 2.66E−10 |
| 2C8H41 | 6.70E+04 | 1.67E−05 | 2.49E−10 |
| 2C8H51 | 7.02E+04 | 9.61E−06 | 1.37E−10 |
| 2C8H12 | 9.52E+04 | 1.33E−05 | 1.39E−10 |
| 2C8H22 | 5.96E+04 | 6.84E−06 | 1.15E−10 |
| 2C8H32 | 7.57E+04 | 1.49E−05 | 1.97E−10 |
| 2C8H42 | 8.06E+04 | 3.07E−05 | 3.81E−10 |
| 2C8H52 | 8.19E+04 | 1.99E−05 | 2.43E−10 |
| 2C8H13 | 1.13E+05 | 2.77E−05 | 2.46E−10 |
| 2C8H23 | 7.95E+04 | 2.28E−05 | 2.87E−10 |
| 2C8H33 | 8.96E+04 | 3.99E−06 | 4.45E−11 |
| 2C8H43 | 7.11E+04 | 2.65E−05 | 3.73E−10 |
| 2C8H53 | 8.09E+04 | 3.11E−05 | 3.84E−10 |

TABLE 16

Affinities of IgG4 class 2C8H11G4 and 4B9H11G4 antibodies to hAng2

| Antibody | Kon (1/Ms) | Kdis (1/s) | $K_D$ (M) |
|---|---|---|---|
| 2C8H11G4 | 4.15E+05 | 4.35E−06 | 1.05E−11 |
| 4B9H11G4 | 4.32E+05 | 3.46E−05 | 8.00E−11 |

Example 6: Analysis of In-Vitro Biological Property of the Selected Humanized Anti-Ang2 Antibodies 6-1: Akt Phosphorylation To investigate whether the humanized anti-Ang2 antibodies induce the downstream signaling of the Tie2 receptor in endothelial cells, HUVECs (LONZA™) were treated with human Ang2 protein together with humanized anti-Ang2 antibody. Then, the level of Akt phosphorylation, the main downstream signaling protein of Tie2 receptor was measured by immunoblotting. To compare the degree of Akt activation, cells were treated with full-length hAng2 (R&D® Systems) alone or antibody alone in the experiment.

Specifically, HUVEC cells ($1 \times 10^5$ cells/ml) were cultured in EGM-2 (LONZA™) at 37° C. in 60 mm culture dish. Cells of 90% confluency were incubated with EBM-2 (LONZA™) for 4 hrs. The serum-starved HUVECs were treated with the mixture of anti-Ang2 antibody and hAng2 protein (1 µg/ml, R&D® Systems), and further incubated for 30 min. The cells were washed with cold PBS, treated with lysis buffer, and lysed at 4° C. for 20 min. Then, the cell lysates were prepared by centrifugation at 13000 rpm for 15 min. 5× SDS sample buffer was added to the cell lysate and the mixture was boiled at 95° C. for 5 min. Then, the mixture was subjected to SDS-PAGE and subsequent Western blotting.

To investigate the phosphorylation of Akt, the membrane was blocked with 5% skim milk-containing TBST for 1 hr at RT, and incubated with anti-phospho-Akt antibody (S473) at 4° C. for about 8 hrs. The amount of phospho-Akt was visualized by enhanced chemiluminescence (ECL). Then, the membrane was incubated in a stripping buffer (Thermo) for 15 min, and then reprobed with an anti-Akt antibody to determine the amount of total Akt.

Figure 3A:
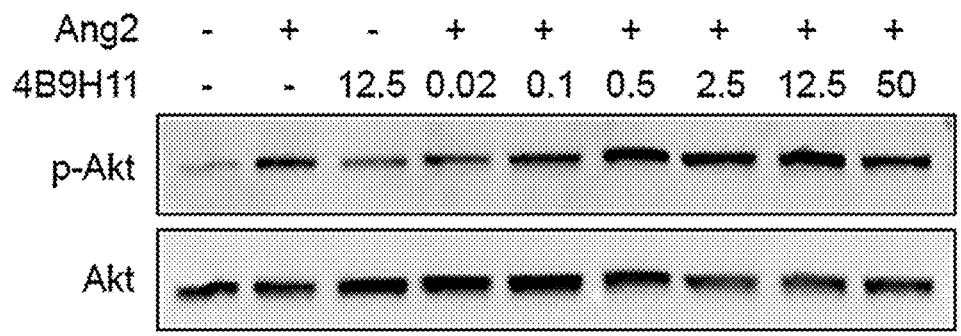
FIGS. 3A-3B. Dose-dependent phosphorylation of Akt (pAkt) by humanized anti-Ang2 antibodies, 4B9H11 (FIG. 3A) and 2C8H11 (FIG. 3B). Serum-starved HUVECs were incubated for 30 min with human Ang2, anti-Ang2 antibodies, or human Ang2 together with various concentrations of anti-Ang2 antibodies. The cell lysates were subjected to SDS-PAGE/Western blotting.
Figure 3B:
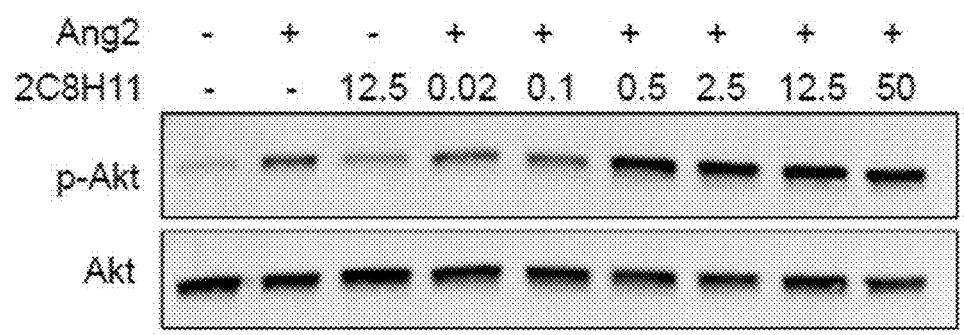

As shown in FIGS. 3A-3B, Akt phosphorylation increased markedly by the treatment of 0.5 µg/ml of anti-Ang2 antibody in the presence of hAng2, and was maintained until 50 µg/ml of antibody concentration in both 4B9H11- and 2C8H11-treated groups. These data indicate that the humanized anti-Ang2 antibodies are able to strongly induce the activation of Akt, the main downstream signaling molecule of Tie2 receptor in endothelial cells. Similar pattern was observed when humanized 4B9H11- or 2C8H11-IgG4 antibodies was tested.

6-2: Tie2 Phosphorylation Induced by Humanized Anti-Ang2 Antibodies

Ang2 binds to the Tie2 receptor and acts as a weak agonist or antagonist. The anti-Ang2 antibody developed in this invention binds to Ang2 to induce Ang2-antibody complexes, further causing clustering of Tie2 receptors and consequently enhancing activation of Tie2 receptor. Experiments were conducted to analyze the effect of anti-Ang2 antibody on Tie2 phosphorylation using HUVECs.

Specifically, HUVECs (LONZA™) were cultured in EGM-2 (LONZA™) at 37° C. and 5% $CO_2$ concentration in a 100 mm culture dish. At 80-90% confluency, the cells were changed to EBM-2 (LONZA™) medium for 2 hrs~ 6 hrs for serum starvation. Humanized anti-Ang2 antibodies at various concentrations (0.02 µg/ml to 50 µg/ml) were mixed with hAng2 protein (1 µg/ml, R&D® Systems) for 30 min. Then, the mixtures were treated with the cultured cells and further incubated for 30 min. The cells were washed twice with cold PBS and then lysed in 1000 µl of lysis buffer (10 mM Tris-Cl pH 7.4, 150 mM NaCl, 5 mM EDTA, 10% glycerol, 1% TRITON™ X-100 (non-ionic polyoxyethylene surfactant), protease inhibitor, phosphatase inhibitor) and then lysed at 4° C. for 60 min. Cell extracts were prepared and centrifuged at 12,000 rpm for 10 min. The supernatant was quantitated by bicinchoninic (BCA) assay.

To 0.5 mg of cell lysate, 1 µg of Tie2 antibody (R&D® Systems, AF313) was added and incubated overnight at 4° C. Then, Dynabeads™ Protein G (Life technologies, uniform, 2.8-µm superparamagnetic beads with recombinant Protein G (~17 kDa) covalently coupled to the surface) was added to react for 2 hrs and immunoprecipitation was performed. The beads were immobilized on one side of the tube using a magnet, washed three times with lysis buffer, and then incubated at 70° C. for 10 min with 2× SDS sample buffer containing reducing agent. The beads were removed from the sample and electrophoresed on a 4-15% SDS protein gel (Bio-Rad) and then transferred to a 0.45 µm PVDF membrane.

Figure 4A:
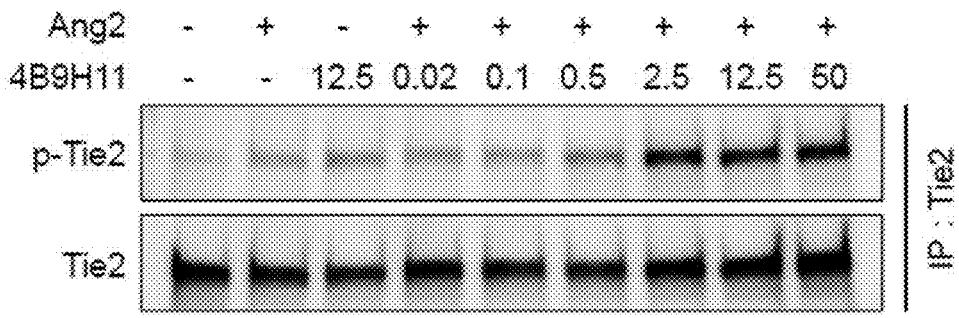
FIGS. 4A-4B. Dose-dependent Tie2 phosphorylation (pTie2) by humanized anti-Ang2 antibodies, 4B9H11 and 2C8H11. The capabilities of 4B9H11 (FIG. 4A) and 2C8H11 (FIG. 4B) antibodies to induce Tie2 phosphorylation were investigated by immunoprecipitation and Western analyses. Serum-starved HUVECs were incubated for 30 min with human Ang2, anti-Ang2 antibody alone, or human Ang2 together with various concentrations of anti-Ang2 antibodies. The cell lysates were subjected to immunoprecipitation with anti-Tie2 antibody, followed by SDS-PAGE/Western blotting analyses.
Figure 4B:
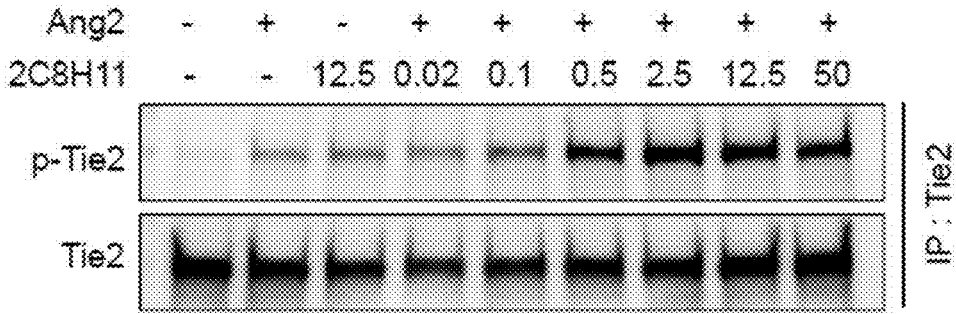

The membrane was blocked with TBS-T mixed with 5% (v/v) BSA for 1 hr at room temperature and incubated with anti-phospho tyrosine antibody (4G10, Millipore®) for 8 hrs at 4° C., followed by the incubation of HRP-conjugated anti-mouse antibody and subsequent Western blotting. To measure the amount of immunoprecipitated Tie2, the membrane was reacted in a stripping buffer (Thermo) for 15 min, then blocked again and reprobed with anti-Tie2 antibody (R&D® Systems, AF313). As shown in FIGS. 4A-4B, when the anti-Ang2 antibody was added together with Ang2 to the HUVEC cells, the phosphorylation of Tie2 was strongly induced in a dose-dependent manner, like in FIGS. 3A-3B. Similar pattern was observed when humanized 4B9H11- or 2C8H11-IgG4 antibodies was tested. These data indicate that the humanized anti-Ang2 antibodies 2C8H11 and 4B9H11 directly induce the activation of Tie2 receptor in human endothelial cells.

6-3: Tie2 Clustering and FOXO1 Translocation in HUVECs

Tie2 clustering at cell-cell junction area and FOXO1 translocation from nucleus to cytosol by anti-Ang2 antibodies were examined in HUVECs by immunofluorescence. Specifically, HUVECs were seeded on 8 well slide chamber (Lab-Tek™ II) and maintained in EGM-2 medium for 2-3 days. At 100% confluence, the cells were serum starved with EBM-2 medium for 4 hrs and then treated with 1 µg/ml anti-Ang2 antibodies together with 1 µg/ml of hAng2 for 30 min. Thereafter, the cells were fixed with 4% formaldehyde in PBS at room temperature (RT) for 10 min, permeabilized with 0.1% TRITON™ X-100 (non-ionic polyoxyethylene surfactant) in PBS, blocked with 1% BSA in PBS at RT for 60 min, and incubated with primary antibodies at RT for 1 hr. The primary antibodies for hTie2, FOXO1, and Human Fc were used. The cells were then incubated with secondary antibodies (Invitrogen) in the dark at RT for 1 hr and mounted with VECTASHIELD® mounting medium with DAPI (Vector Labs, antifade mounting media optimized for immunofluorescence applications). Images were taken with a laser scanning confocal microscope (LSM880, Carl Zeiss).

Figure 5:
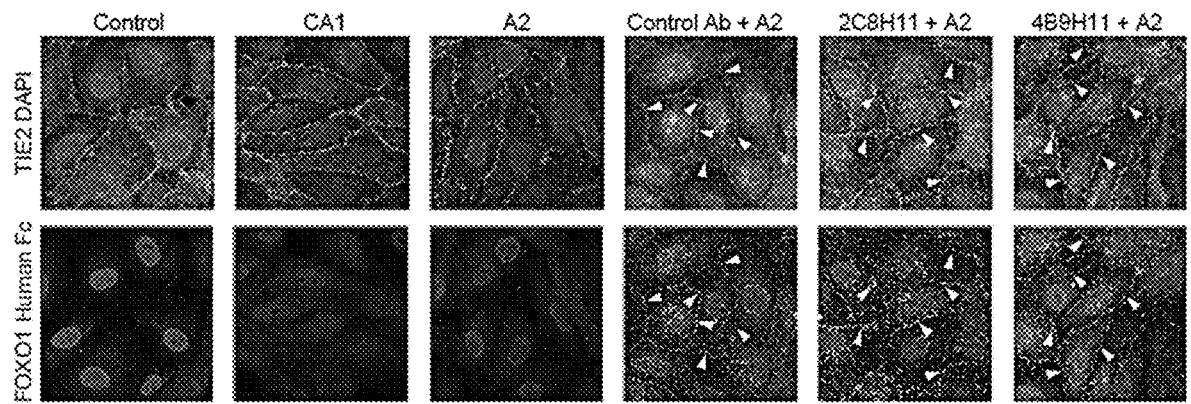
FIG. 5. Tie2 receptor clustering and FOXO1 translocation by humanized Ang2 antibodies. HUVECs were serum starved for 6 hrs and were incubated with COMP-Ang1 (CA1), Ang2 (A2), or Ang2 together with anti-Ang2 antibodies (Control Ab, 2C8H11 or 4B9H11) for 30 min. After fixation, HUVECs were stained with DAPI, anti-Tie2 antibody, anti-FOXO1 antibody and anti-human Fc to investigate Tie2 clustering at cell surface, FOXO1 translocation from nucleus, and the presence of humanized Ang2 antibodies in the cell-cell junction areas. Arrowheads indicate the clustered Tie2 and co-localized Ang2 antibodies at cell-cell contacts.
Figure 6:
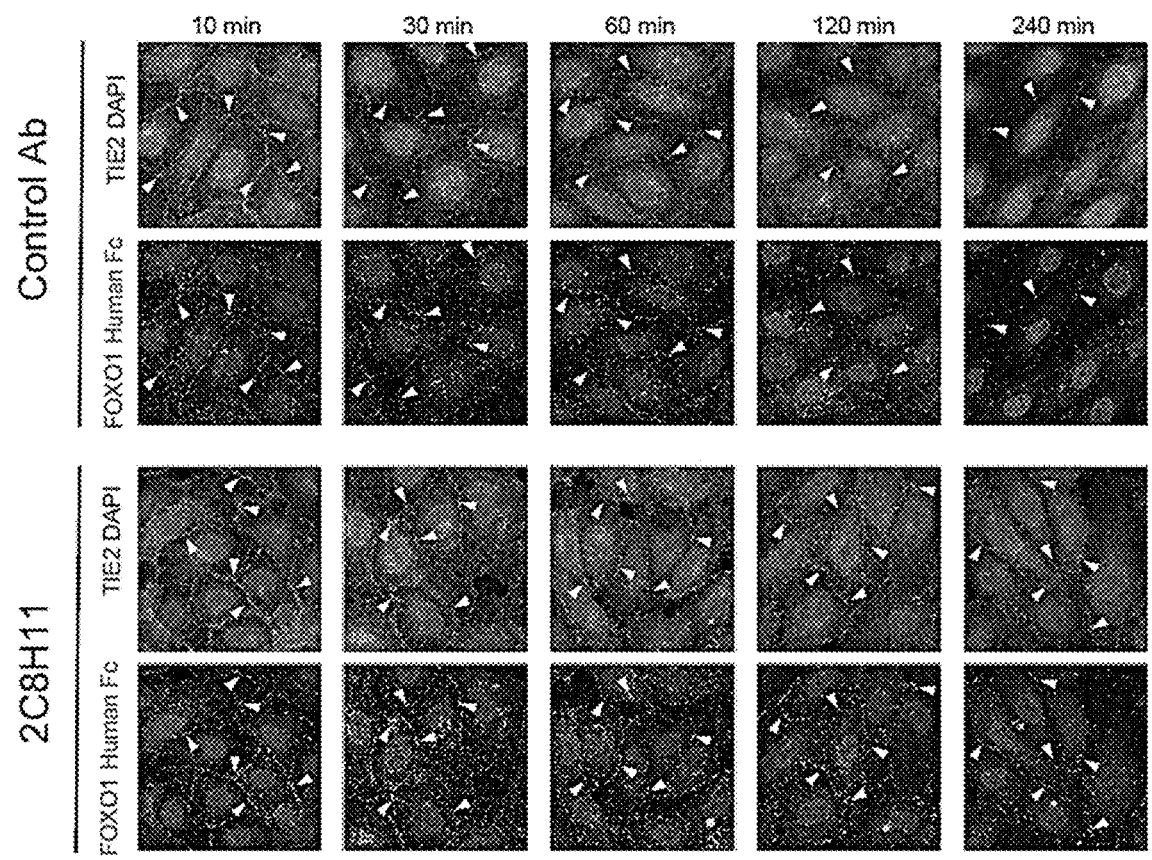
FIG. 6. Time-courses of Tie2 receptor clustering, FOXO1 translocation and localization of Ang2 antibodies in the cell-cell junctions in HUVECs. Serum-starved HUVECs were incubated with anti-Ang2 antibodies (control Ab or 2C8H11) for various time points, from 10 min to 240 min. After cell fixation, clustered Tie2 receptors at cell surface and endocytosed Tie2 receptors were investigated by staining with anti-Tie2 antibody. Humanized anti-Ang2 antibodies at cell surface and cytosol were probed with anti-human Fc antibody. Arrowheads indicate the clustered Tie2 and co-localized Ang2 antibodies at cell-cell contacts.

As shown in FIG. 5, the treatment of 2C8H11 or 4B9H11 with hAng2 induced Tie2 translocation/clustering to cell-cell contact just like Comp-Ang1 (CA1) or Control Ang2 antibody, which was known to induce Tie2 clustering and activation (Han et al., 2016, Science Translation Medicine). Consistent with a previous report showing FOXO1 localization in the cytoplasm after phosphorylation (Zhang et al, JBC 2002, 277, 45276-45284) while it was located in the nucleus under the basal, serum-starved condition, FOXO1 became markedly disappeared in nucleus with the treatment of 2C8H11+hAng2 or 4B9H11+hAng2, compared to serum-starved control. Meanwhile, Ang2 treatment negligibly induced FOXO1 translocation form nucleus to cytosol. Interestingly, 2C8H11, 4B9H11 humanized antibodies were found to be co-localized with clustered Tie2 receptor at cell-cell contact and endocytosed Tie2 receptor in cytosol (FIG. 5), indicating that anti-Ang2 antibody form a tripartite complex with Tie2 receptor through binding to Ang2. 2C8H11-induced Tie2 clustering and FOXO1 translocation was examined in a time-course study (from 10 min to 240 min). As shown in FIG. 6, in the presence of hAng2, control Ang2 Ab induced Tie2 clustering at the cell-cell contact within 10 min, and triggered the endocytosis of clustered Tie2 receptors. After 30 min treatment of control Ang2 Ab+hAng2, Tie2 receptor at cell-cell contact was markedly diminished, and Tie2 receptor was mostly disappeared in 120 min and 240 min. When control Ang2 antibody was stained with anti-human Fc antibody, it showed a similar pattern just like that of Tie2 receptor. In contrast, in the case of 2C8H11 and hAng2, Tie2 clustering at cell-cell contact was sustained even after 240 min treatment. Consistently, co-localized 2C8H11 antibody with Tie2 at cell-cell contact was also maintained until 240 min (FIG. 6).

6-4: Inhibition of Vascular Permeability by Humanized Anti-Ang2 Antibodies

Figure 7:
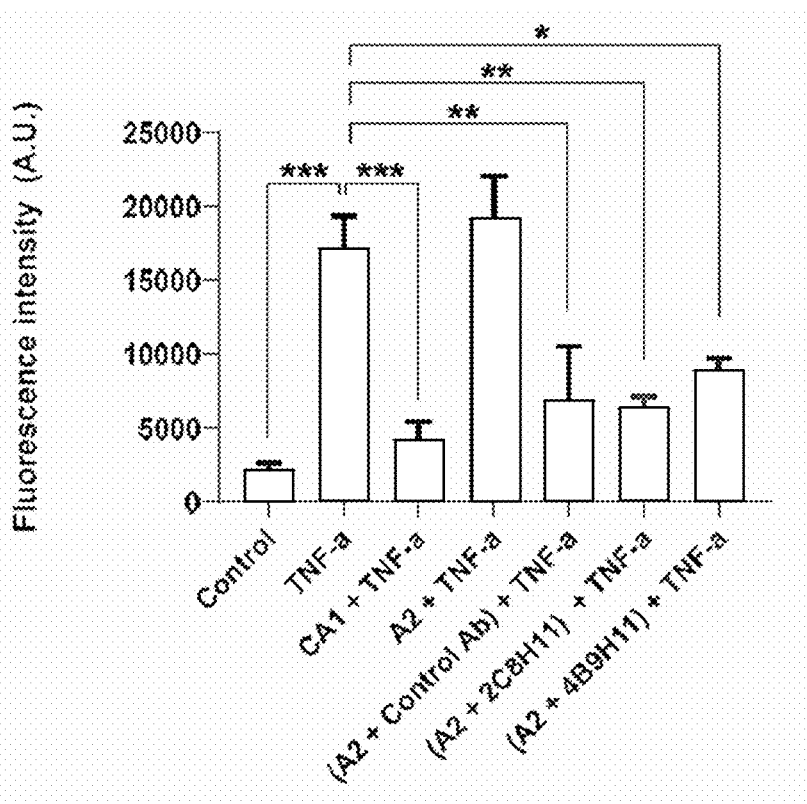
FIG. 7. Inhibition of vascular permeability by humanized anti-Ang2 antibodies. HUVECs were seeded on transwell chamber and grown for 3 days. At 100% confluency, HUVECs were pre-treated with COMP-Ang1 (CA1, 0.5 µg/ml), Ang2 (A2, 1 µg/ml), Ang2 together with Control Ab (A2+Control Ab, 1 µg/ml), 2C8H11 (A2+2C8H11, 1 µg/ml) or 4B9H11 (A2+4B9H11, 1 µg/ml) for 30 min and treated with TNF-α (100 ng/ml) for 22 hrs into the upper chamber.

Vascular leakage assay was carried out in HUVECs using In Vitro Vascular Permeability Assay Kit (Millipore®) according to the manufacturer's instruction. HUVECs were seeded into the insert of the transwell plate and cultured for 3 days for 100% confluence. The HUVECs were pre-incubated with Ang2 (1 µg/ml), Ang2 (1 µg/ml) together with Control, 2C8H11 or 4B9H11 antibody (1 µg/ml) for 30 min, and then TNF-α (100 ng/ml) was added, and the cells were incubated at 37° C. for 22 hr. FITC-dextran was added to the upper chamber and incubated for 20 min. Passage of FITC-dextran though the HUVEC monolayer was measured by a fluorescence reader at excitation and emission wavelengths of 485 and 535 nm, respectively. As shown in FIG. 7, pre-treatment of anti-Ang2 antibodies with Ang2 significantly inhibited the vascular leakage induced by vascular-leakage promoting factor TNF-α.

Example 7: Affinity Measurement of Humanized Anti-Ang2 Antibodies Against mAng2

The affinity of humanized antibodies for mouse Ang2 (mAng2) was analyzed by ELISA. Specifically, mAng2 was diluted in 30 µl of a coating buffer (0.1 M sodium carbonate buffer) at 20 ng per well in a half 96-well plate (Corning® 3690) and incubated overnight at 4° C. After washing with TBS-T solution for 3 times, the well plate was blocked with 3% skim milk at room temperature for 1 hr and then washed again. 2C8H11 and 4B9H11 were serially diluted from 3 mg/ml to 300 ng/ml. After loading 30 µl of the diluted ant-Ang2 antibodies into wells, the well plate was incubated at room temperature for 2 hrs. Next, 30 µl of a 1:3000 dilution of anti-human IgG (Fab)-HRP (Jackson) secondary antibody was added to each well and incubated at room temperature for 1 hr. After completion of all reactions, the plate was washed again with TBS-T and then treated with 30 µl of TMB solution per well. After developing for 5 min, the plate was treated with 1N sulfuric acid to stop the reaction, and absorbance was measured at 450 nm. Based on the measured OD value, the EC50 value was analyzed using WorkOut 2.5 program (PerkinElmer™). EC50 of 4B9H11 and 2C8H11 for mAng2 binding were 105 µg/ml and 97 µg/ml, respectively, (FIGS. 8A-8B).

Example 8: Evaluation of the Tumor Growth Inhibition Effect in LLC Subcutaneous Model 2C8H11 anti-Ang2 antibody was tested for its ability to inhibit tumor growth in LLC (Lewis Lung Carcinoma) cell line tumor model. Specifically, LLC cell line (ATCC) was cultured in DMEM (GIBCO™) supplemented with 10% FBS (GIBCO™). LLC cells ($1\times10^6$ in 100 µl of PBS) were subcutaneously injected into 6~8-week-old C57BL/6 mice (Jackson Laboratory) which were anesthetized with a mixture of Ketamine and Xylazine. When the volume of the tumors reached 50~100 mm$^3$, the mice were intraperitoneally administered with 10 mg/kg of 2C8H11 antibody every 2~3 days. Cisplatin (Cpt) was injected intraperitoneally once at a dose of 3 mg/kg in both monotherapy and combination therapy groups. The changes in tumor volume was tracked over the following days. Tumor volume (V) was measured using the formula:

$$V=(width^2 \times length)/2$$

$$V=(width^2 \times length)/2$$

The experiment was performed in 4 groups: Fc (control group), Fc+Cpt group, 2C8H11 group, and 2C8H11+Cpt group. As shown in FIG. 9, 2C8H11 antibody inhibited tumor growth by 29% compared with Fc, which was similar to the tumor growth inhibition effect by Fc+Cpt injection. Meanwhile, combined treatment with 2C8H11 and Cpt delayed tumor growth by 47% compared with Fc. Thus, these results demonstrate that combined treatment with 2C8H11 with Cpt inhibited tumor growth most potently.

Example 9: The Tumor Vessel Normalization Effect of 2C8H11 Antibody

In order to investigate the changes in tumor vessels by 2C811 antibody, we obtained frozen sections of tumor samples and performed immunofluorescence analyses by staining with a blood vessel-specific marker, CD31, and pericyte-specific marker, PDGFRβ. In detail, the tumor samples were harvested from the mice from the experiment described in Example 8, which were fixed in 4% paraformaldehyde (PFA, Merck), dehydrated in 30% sucrose (Junsei), embedded in OCT compound (Leica), and sectioned using a cryostat (Leica). The resulting frozen sections were blocked for 1 hr using a Protein Blocking Buffer (DAKO). Then the sections were stained with hamster anti-CD31 antibody (1:200, Millipore®) and rat anti-PDGFRB antibody (1:200, eBioscience™) in PBS at 4° C. for 8 hrs. After washing 3 times with PBS, the sections were stained with ALEXA FLUOR® 488-conjugated anti-hamster IgG antibody and Alexa ALEXA FLUOR® 594-conjugated anti-rat IgG antibody (1:1000, Jackson Immunoresearch) in PBS for 1 hr at room temperature. After another 3 washes with PBS, the sections were mounted in fluorescence mounting medium (DAKO) using a coverslip (Marienfeld). The stained sections were imaged using LSM880 confocal microscope (Zeiss).

The results are shown in FIGS. 10A-10C. Compared with tumors treated with Fc or Fc+Cpt, tumor blood vessel (BV) density was reduced by 56% in either 2C8H11 or 2C8H11+Cpt treated tumors and the morphology of these vasculature was normalized so that it was similar to a normal blood vessel (FIG. 10B). Furthermore, the tumors treated with 2C8H11 or 2C8H11+Cpt had increased PDGFRβ$^+$ pericyte coverage (2.4-fold increase) (FIG. 10C), and the blood vessel and perivascular cells were more closely associated with each other. These results show that 2C8H11 antibody can reduce the blood vessel density within a tumor mass and normalize their morphology.

Example 10: Increased Functionality of Tumor Vessels by 2C8H11 Antibody

To analyze the functionality of tumor vessels after treatment with 2C8H11, vessel perfusability and hypoxia status were evaluated. Before harvesting tumor mass, the mice were intravenously injected with 100 μl of DyLight™ 488-Lectin (Vector laboratory) and intraperitoneally injected with 60 mg/kg of Pimonidazole-HCl (HYPOXYPROBE™+) dissolved in PBS for 30 min before sacrifice. The mice were perfusion-fixed with 4% PFA. We obtained frozen sections from the tumor mass, which were stained with hamster anti-CD31 antibody (1:200, Millipore®) and 4.3.11.3 mouse Pacific blue-Mab (1:50, HYPOXYPROBE™+) in PBS. The sections were imaged using LSM880 confocal microscope (Zeiss), and the obtained images were analyzed using ImageJ software (http://rsb.info.nih.gov/ij) to quantify Lectin+area/CD31+area and HYPOXYPROBE™+area.

The results are shown in FIGS. 11A-11C. The tumors treated with 2C8H11 or 2C8H11+Cpt displayed normalized tumor vessels that had enhanced perfusion as judged by increased Lectin+area/CD31+area (approximately 3-fold increase in perfusion), compared with those treated with Fc or Fc+Cpt (FIG. 11B). Furthermore, hypoxia, as indicated by HYPOXYPROBE™+area, was decreased in tumors treated with 2C8H11 or 2C8H11+Cpt by 72%, when compared with tumors treated with Fc or Fc+Cpt (FIG. 11C). These results indicate that 2C8H11 antibody not only normalized the morphology of tumor vessels but also enhances their functionality by increasing vessel perfusability, which subsequently lead to decreased hypoxia.

Example 11: Increased Anti-Cancer Drug Delivery into the Tumor Mass by 2C8H11 Antibod The drug, Cpt, inhibits tumor growth by inhibiting DNA synthesis, and has been widely used in human cancer patients. To evaluate whether the 2C8 antibody can increase the delivery of this drug into tumors by normalizing tumor vessels, the frozen sections of tumors were stained with anti-Cisplatin-modified DNA antibody (1:100, Abcam) and hamster anti-CD31 antibody (1:200, Millipore®). As shown in FIGS. 12A and 12B, the levels of Cpt-modified DNA was significantly increased by 2.1 folds in the 2C8H11/Cpt-treated group, compared with Fc+Cpt treated group. This result shows that the delivery of Cpt to the tumor mass was enhanced due to the normalized tumor vessels by 2C8H11 antibody, which subsequently potently inhibits tumor growth.

Example 12: CNV Regression and Vascular Leakage Suppression Effect of 2C8H11

Antibody in Laser-Induced CNV Model.

2C8H11 antibody was tested for its ability to inhibit choroidal neovascularization (CNV), the hallmark of wet age-related macular degeneration (AMD) using laser-induced CNV model. After dilation of pupils with 5 mg/ml phenylephrine and 5 mg/ml tropicamide eye drops (Santen Pharmaceutical) and instillation of 0.5% proparacaine hydrochloride eye drops (Alcon) for topical anesthesia, laser photocoagulator (Lumenis Inc.) with a slit lamp delivery system was used with a glass coverslip as a contact lens to visualize the retina. Sufficient laser energy (532 nm wavelength, 250 mW power, 100 ms duration, 50 μm spot size) was delivered in 4 locations for each eye (the 3, 6, 9 and 12 o'clock positions of the posterior pole). Only burns that produced a bubble at the time of laser photocoagulation, indicating the rupture of the Bruch's membrane, were included in this study. Spots containing hemorrhage at the laser site were excluded from the analysis. To recapitulate a clinical situation, 2C8H11 (5 μg) was administered intravitreally to the mice at 7 days after laser photocoagulation (FIG. 13A). As a control or as for comparison, Fc or VEGF-Trap (5 µg each) was administered in the same manner to the mice. To intravitreally administer indicated reagents, ~1 µl (5 mg/ml) containing 5 µg of each reagent was injected into the vitreal cavity using the Nanoliter 2000 micro-injector (World Precision Instruments) fitted with a glass capillary pipette. CD31+CNV volumes of the retinal pigment epithelium (RPE)-choroid-sclera flat mounts were calculated using the MATLAB® Image Processing Toolbox™ (Math Works, a comprehensive set of reference-standard algorithms and workflow apps for image processing, analysis, visualization, and algorithm development) at 14 days after laser photocoagulation. Anti-CD31 antibody (1:200, Millipore®) was used for the detection of endothelial cells of CNV. VEGF-Trap effectively induced CNV regression by 64.4% compared with Fc, and 2C8H11 similarly induced CNV regression (65.3%) (FIG. 13B, C). Combined fluorescein angiography (FA) and indocyanine green angiography (ICGA) enabled us to measure vascular leakage at the neovessels around the laser injury site. Continuous-wave laser modules at 488 nm and 785 nm were used as excitation sources for fluorescein and ICG, respectively. A raster scanning pattern of excitation lasers was achieved by a scanner system consisting of a rotating polygonal mirror (MC-5; Lincoln Laser) and a galvanometer-based scanning mirror (6230H; Cambridge technology), and delivered to the back aperture of an imaging lens. A high numerical aperture (NA) objective lens (PlanApo λ, NA 0.75; Nikon) was used as the imaging lens to provide wide-field fundus fluorescence images. Fluorescence signals detected by photomultiplier tubes (R9110; Hamamatsu Photonics) were digitized by frame grabber and reconstructed to images with size of 512×512 pixels per frame in real time. To visualize late-phase (6 min) FA and ICGA images utilizing the angiography system, 10 mg of fluorescein sodium (Alcon) and 0.15 mg of ICG (Daiichi Pharmaceutical) were administered intraperitoneally and intravenously, respectively. The imaging procedure was performed under systemic anesthesia and pupil dilation to improve the quality of images. Leaky areas from CNV were calculated as the total measured hyperfluorescent areas in FA images divided by the total measured CNV areas in ICGA images using a Java-based imaging software (ImajeJ; National Institutes of Health). Compared with Fc, both VEGF-Trap (37.0%) and 2C8H11 (38.3%) similarly suppressed vascular leakage (FIG. 13B, D). Of note, the Fc-treated group showed no significant difference in vascular leakage between 6 and 14 days after laser photocoagulation, but VEGF-Trap and 2C8H11 markedly reduced vascular leakage (45.6% and 50.0%, respectively) (FIG. 13B, D). Thus, the magnitude of the suppression of CNV and vascular leakage was quantitatively indistinguishable between VEGF-Trap and 2C8H11 in the mouse model of laser-induced CNV.

Example 13: CNV Regression and Choriocapillary Regeneration Effect of 2C8H11 Antibod To determine the effect of 2C8H11 in CNV regression and choriocapillary regeneration after establishment of CNV, Fc, VEGF-Trap, control antibody or 2C8H11 (5 µg each) was given intravitreally to the mice by the Nanoliter 2000 micro-injector (World Precision Instruments) at 7 days after laser photocoagulation. Intra-vital optical coherence tomography angiography (OCTA) was performed at 6, 14, 21, and 35 days after laser photocoagulation (FIG. 14A). The retinochoroidal layers were imaged using a prototype high-speed swept-source optical coherence tomography (OCT) system, utilizing a custom ring cavity wavelength-swept laser centered at 1048 nm with an A-scan rate of 230 kHz. OCT images were collected in a 1.7 mm×1.7 mm field of view within the retino-choroidal layer to monitor regeneration of choroidal vasculatures at the site of laser photocoagulation after intravitreal injection of reagents. To obtain cross-sectional OCT angiograms, which allows for selective visualization of blood vessels without the retinal and choroidal parenchyma, we compared repeatedly recorded B-scan images and detected pixel-by-pixel intensity decorrelation of those images mainly caused by movement of erythrocytes inside the vessels. Then, by using automatic layer flattening and segmentation algorithms, cross-sectional OCT angiograms were flattened to RPE, and en face OCT angiograms were generated by separate projection of each flattened cross-sectional OCT angiogram in three depth ranges: inner retinal, outer retinal and choroidal layers. The outer plexiform layer and Bruch's membrane were defined as the boundaries separating inner retinal, outer retinal, and choroidal layers. The density of retina and choroid vessel was automatically calculated as the proportion of measured area occupied by flowing blood vessels defined as pixels having decorrelation values above the threshold level. Avascular pixels were detected from the en face OCT angiogram representing choroidal layer by means of the image processing toolbox of MATLAB® (Math Works). Then the total volume of the avascular space surrounding the laser injury site was calculated by summing the number of avascular pixels multiplied by the volume of one pixel. In order to analyze the changing complexion of avascular space volume, serially measured values in each eye were transformed into percentage change from baseline value. There was a slight reduction of the CNV volume in outer retinas treated with Fc, but those treated with VEGF-Trap and 2C8H11 showed markedly reduced CNV volume (FIG. 14B, C). Meanwhile, a slight reduction of the avascular space was observed in choroids treated with Fc. Intriguingly, choroids in 2C8H11-treated eyes showed serial and profound reduction of the avascular space by 30.1%, 36.4%, and 37.0% at 14, 21, and 35 days after laser photocoagulation, respectively (FIG. 14B, D). Similarly, choroids in control Ab-treated eyes showed reduction of the avascular space by 21.7%, 30.2%, and 38.0% at 14, 21, and 35 days after laser photocoagulation, respectively (FIG. 14B, D). However, choroids in VEGF-Trap-treated eyes showed increased avascular space by 11.4%, 16.0%, and 18.1% at D14, D21, and D35, respectively (FIG. 14B, D). Overall, these findings indicate that both 2C8H11 and control Ab promotes regeneration of the choriocapillaris, while VEGF-Trap leads to choriocapillary regression in the laser-induced CNV model.

Example 14: Co-Localization of 2C8H11 Antibody and CD31 in Endothelial Cells of CN To investigate whether subcutaneously injected 2C8H11 can also exert the therapeutic effects on CNV, we firstly evaluated co-localization 2C8H11 antibody and CD31 in endothelial cells of CNV. The subcutaneous administration of 2C8H11 antibody (25 mg/kg) was performed at 1 day after laser photocoagulation. As a control, Fc (25 mg/kg) was administered in the same manner to the mice. The co-localization of 2C8H11 antibody and anti-CD31 antibody (1:200, Millipore®) in endothelial cells of CNV was directly detected by anti-human IgG antibody (1:1000, Jackson ImmunoResearch Laboratories) at 2, 4, and 8 days after laser

Example 15: CNV Inhibition Effect of Subcutaneously Injected 2C8H11 Antibod

To determine the effect of subcutaneously injected 2C8H11 antibody in CNV inhibition, the subcutaneous administration of 2C8H11 antibody (25 mg/kg) was performed at 1 day after laser photocoagulation. As a control, Fc (25 mg/kg) was administered in a same manner to the mice. Anti-CD31 antibody (1:200, Millipore®) was used for the detection of endothelial cells of CNV, and CD31+CNV volumes of the RPE-choroid-sclera flat mounts were calculated using the MATLAB® Image Processing Toolbox™ (Math Works) at 8 days after laser photocoagulation (FIG. 16A). 2C8H11 effectively inhibited CNV formation by 69.9% compared with Fc (FIG. 16B, C), indicating that not only intravitreal injection but also subcutaneous injection of 2C8H11 have the inhibitory effect on CNV.

The microorganism of the present invention was named as 2C8 and deposited at the Korean Cell Line Bank (KCLB) at Cancer Research Institute, Seoul National University, College of Medicine, 28 Yongon-dong, Chongno-Gu, Seoul, 110-744, Korea on Jan. 30, 2018 (Accession No: KCLRF-BP-00417).

The microorganism of the present invention was named as 4B9 and deposited at the Korean Cell Line Bank (KCLB) at Cancer Research Institute, Seoul National University, College of Medicine, 28 Yongon-dong, Chongno-Gu, Seoul, 110-744, Korea on Jan. 30, 2018 (Accession No: KCLRF-BP-00418).

INDUSTRIAL APPLICABILITY

The present invention relates to an antibody that inhibits Ang2 and simultaneously activates Tie2 receptor resulting in promotes downstream signal transduction. It provides a method of inhibiting Ang2-induced angiogenesis and reducing vascular permeability. In addition, the antibody according to the present invention can be useful for diagnosis and treatment of abnormal angiogenesis-related diseases such as eye diseases or cancer and/or diseases caused by increased vascular permeability.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention will be defined by the accompanying claims and their equivalents.

SEQUENCE LISTING

```
Sequence total quantity: 117
SEQ ID NO: 1            moltype = AA  length = 496
FEATURE                 Location/Qualifiers
REGION                  1..496
                        note = Human Angiopoietin-2 full-length
source                  1..496
                        mol_type = protein
                        organism = synthetic construct
SEQUENCE: 1
MWQIVFFTLS CDLVLAAAYN NFRKSMDSIG KKQYQVQHGS CSYTFLLPEM DNCRSSSSPY   60
VSNAVQRDAP LEYDDSVQRL QVLENIMENN TQWLMKLENY IQDNMKKEMV EIQQNAVQNQ  120
TAVMIEIGTN LLNQTAEQTR KLTDVEAQVL NQTTRLELQL LEHSLSTNKL EKQILDQTSE  180
INKLQDKNSF LEKKVLAMED KHIIQLQSIK EEKDQLQVLV SKQNSIIEEL EKKIVTATVN  240
NSVLQKQQHD LMETVNNLLT MMSTSNSAKD PTVAKEEQIS FRDCAEVFKS GHTTNGIYTL  300
TFPNSTEEIK AYCDMEAGGG GWTIIQRRED GSVDFQRTWK EYKVGFGNPS GEYWLGNEFV  360
SQLTNQQRYV LKIHLKDWEG NEAYSLYEHF YLSSEELNYR IHLKGLTGTA GKISSISQPG  420
NDFSTKDGDN DKCICKCSQM LTGGWWFDAC GPSNLNGMYY PQRQNTNKFN GIKWYYWKGS  480
GYSLKATTMM IRPADF                                                 496

SEQ ID NO: 2            moltype = AA  length = 221
FEATURE                 Location/Qualifiers
REGION                  1..221
                        note = Human Angiopoietin-2 receptor-binding domain(RBD)
source                  1..221
                        mol_type = protein
                        organism = synthetic construct
SEQUENCE: 2
EEQISFRDCA EVFKSGHTTN GIYTLTFPNS TEEIKAYCDM EAGGGGWTII QRREDGSVDF   60
QRTWKEYKVG FGNPSGEYWL GNEFVSQLTN QQRYVLKIHL KDWEGNEAYS LYEHFYLSSE  120
ELNYRIHLKG LTGTAGKISS ISQPGNDFST KDGDNDKCIC KCSQMLTGGW WFDACGPSNL  180
NGMYYPQRQN TNKFNGIKWY YWKGSGYSLK ATTMMIRPAD F                     221

SEQ ID NO: 3            moltype = AA  length = 5
FEATURE                 Location/Qualifiers
REGION                  1..5
                        note = CDRH1
source                  1..5
                        mol_type = protein
                        organism = synthetic construct
SEQUENCE: 3
DYYMY                                                               5

SEQ ID NO: 4            moltype = AA  length = 17
FEATURE                 Location/Qualifiers
```

```
REGION                      1..17
                            note = CDRH2
source                      1..17
                            mol_type = protein
                            organism = synthetic construct
SEQUENCE: 4
TISVGGSFTY YPDSVKG                                                       17

SEQ ID NO: 5                moltype = AA   length = 10
FEATURE                     Location/Qualifiers
REGION                      1..10
                            note = CDRH3
source                      1..10
                            mol_type = protein
                            organism = synthetic construct
SEQUENCE: 5
DWGLRPWFVY                                                               10

SEQ ID NO: 6                moltype = AA   length = 11
FEATURE                     Location/Qualifiers
REGION                      1..11
                            note = CDRL1
source                      1..11
                            mol_type = protein
                            organism = synthetic construct
SEQUENCE: 6
KASQDVSTAV A                                                             11

SEQ ID NO: 7                moltype = AA   length = 7
FEATURE                     Location/Qualifiers
REGION                      1..7
                            note = CDRL2
source                      1..7
                            mol_type = protein
                            organism = synthetic construct
SEQUENCE: 7
WASTRHT                                                                   7

SEQ ID NO: 8                moltype = AA   length = 9
FEATURE                     Location/Qualifiers
REGION                      1..9
                            note = CDRL3
source                      1..9
                            mol_type = protein
                            organism = synthetic construct
SEQUENCE: 8
QQHYSTPPT                                                                 9

SEQ ID NO: 9                moltype = AA   length = 119
FEATURE                     Location/Qualifiers
REGION                      1..119
                            note = Heavy Chain Variable Region
source                      1..119
                            mol_type = protein
                            organism = synthetic construct
SEQUENCE: 9
EVQLVESGGG LVKPGGSLKL SCAASGFTFS DYYMWVRQT PEKRLEWVAT ISVGGSFTYY          60
PDSVKGRFTI SRDNAKNNLY LQMSSLKSED TAMYYCARDW GLRPWFVYWG QGTLVTVSA        119

SEQ ID NO: 10               moltype = DNA   length = 357
FEATURE                     Location/Qualifiers
misc_feature                1..357
                            note = Heavy Chain Variable Region
source                      1..357
                            mol_type = other DNA
                            organism = synthetic construct
SEQUENCE: 10
gaagtgcagc tggtggagtc tgggggaggc ttagtgaagc tggagggtc cctgaaactc          60
tcctgtgcag cctctggatt cactttcagt gactattaca tgtattgggt tcgccagact       120
ccggaaaaga ggctggagtg gtcgcaacc attagtgttg gtggtagttt cacctactat        180
ccagacagtg tgaaggggcg attcaccatc tccagagaca tgccaagaa caacctgtac        240
ctgcaaatga gcagtctgaa gtctgaggac acagccatgt attactgtgc aagagactgg       300
ggattacgac cctggtttgt ttactgggc caagggactc tggtcactgt ctctgca           357

SEQ ID NO: 11               moltype = AA   length = 107
FEATURE                     Location/Qualifiers
REGION                      1..107
                            note = Light Chain Variable Region
source                      1..107
```

```
                          mol_type = protein
                          organism = synthetic construct
SEQUENCE: 11
DIVMTQSHKF MSTSVGDRVS ITCKASQDVS TAVAWYQQKP GQSPKLLIYW ASTRHTGVPD    60
RFTGSGSGTD YTLTISSVQA EDLALYYCQQ HYSTPPTFGS GTKLEIK                 107

SEQ ID NO: 12             moltype = DNA    length = 321
FEATURE                   Location/Qualifiers
misc_feature              1..321
                          note = Light Chain Variable Region
source                    1..321
                          mol_type = other DNA
                          organism = synthetic construct
SEQUENCE: 12
gacattgtga tgacccagtc tcacaaattc atgtccacat cagtaggaga cagggtcagc    60
atcacctgca aggccagtca ggatgtgagt actgctgtag cctggtatca acaaaaacca   120
gggcaatctc ctaaactact gatttactgg gcatccaccc ggcacactgg agtccctgat   180
cgcttcacag gcagtggatc tgggacagat tatactctca ccatcagcag tgtgcaggct   240
gaagacctgg cactttatta ctgtcagcaa cattatagca ctcctcccac gttcggctcg   300
gggacaaagt tggaaataaa a                                             321

SEQ ID NO: 13             moltype = AA    length = 5
FEATURE                   Location/Qualifiers
REGION                    1..5
                          note = CDRH1
source                    1..5
                          mol_type = protein
                          organism = synthetic construct
SEQUENCE: 13
SYWMH                                                                 5

SEQ ID NO: 14             moltype = AA    length = 17
FEATURE                   Location/Qualifiers
REGION                    1..17
                          note = CDRH2
source                    1..17
                          mol_type = protein
                          organism = synthetic construct
SEQUENCE: 14
MIDPSDSETR LNQKFKD                                                   17

SEQ ID NO: 15             moltype = AA    length = 12
FEATURE                   Location/Qualifiers
REGION                    1..12
                          note = CDRH3
source                    1..12
                          mol_type = protein
                          organism = synthetic construct
SEQUENCE: 15
RFYYGSDWYF DV                                                        12

SEQ ID NO: 16             moltype = AA    length = 11
FEATURE                   Location/Qualifiers
REGION                    1..11
                          note = CDRL1
source                    1..11
                          mol_type = protein
                          organism = synthetic construct
SEQUENCE: 16
KASQDVGTAV A                                                         11

SEQ ID NO: 17             moltype = AA    length = 7
FEATURE                   Location/Qualifiers
REGION                    1..7
                          note = CDRL2
source                    1..7
                          mol_type = protein
                          organism = synthetic construct
SEQUENCE: 17
WASTRHT                                                               7

SEQ ID NO: 18             moltype = AA    length = 9
FEATURE                   Location/Qualifiers
REGION                    1..9
                          note = CDRL3
source                    1..9
                          mol_type = protein
                          organism = synthetic construct
SEQUENCE: 18
```

QQYSSYPLT                                                                          9

```
SEQ ID NO: 19          moltype = AA  length = 121
FEATURE                Location/Qualifiers
REGION                 1..121
                       note = Heavy Chain Variable Region
source                 1..121
                       mol_type = protein
                       organism = synthetic construct
SEQUENCE: 19
QVQLQQSGPQ LVRPGASVKI SCKASGYSFT SYWMHWVKQR PGQGLEWIGM IDPSDSETRL    60
NQKFKDKASL TVDKSSSTAY MQLSSPTSGD SAVYYCARRF YYGSDWYFDV WGAGSTVTVS   120
S                                                                  121

SEQ ID NO: 20          moltype = DNA  length = 363
FEATURE                Location/Qualifiers
misc_feature           1..363
                       note = Heavy Chain Variable Region
source                 1..363
                       mol_type = other DNA
                       organism = synthetic construct
SEQUENCE: 20
caggtgcaac tgcagcagtc tgggcctcag ctggttaggc ctggggcttc agtgaagata    60
tcctgcaagg cttctggtta ctcattcacc agctactgga tgcactgggt gaagcagagg   120
cctggacaag gtcttgagtg gattggcatg attgatcctt ccgatagtga aactaggtta   180
aatcagaagt tcaaggacaa ggcctcattg actgtagaca atcctccag cacagcctac    240
atgcaactca gcagcccgac actggggac tctgcggtct attactgtgc aagacgtttt    300
tactacgggt cggactggta cttcgatgtc tggggcgcag ggtccacggt caccgtctcc   360
tca                                                                363

SEQ ID NO: 21          moltype = AA  length = 107
FEATURE                Location/Qualifiers
REGION                 1..107
                       note = Light Chain Variable Region
source                 1..107
                       mol_type = protein
                       organism = synthetic construct
SEQUENCE: 21
DIVMTQSHKF MSTSVGDRVS ITCKASQDVG TAVAWYQQKP GQSPKLLIYW ASTRHTGVPD    60
RFTGSGSGTD FTLTISNVQS EDLADYFCQQ YSSYPLTFGS GTKLEIK                107

SEQ ID NO: 22          moltype = DNA  length = 321
FEATURE                Location/Qualifiers
misc_feature           1..321
                       note = Light Chain Variable Region
source                 1..321
                       mol_type = other DNA
                       organism = synthetic construct
SEQUENCE: 22
gacattgtga tgacccagtc tcacaaattc atgtccacat cagtaggaga cagggtcagc    60
atcacctgca aggccagtca ggatgtgggt actgctgtag cctggtatca acagaaacca   120
ggtcaatctc ctaaactact gatttactgg gcatccaccc ggcacactgg agtccctgat   180
cgcttcacag gcagtggatc tgggacagat ttcactctca ccattagcaa tgtgcagtct   240
gaagacttgg cagattattt ctgtcagcaa tatagcagct atcctctcac gttcggctcg   300
gggacaaagt tggaaataaa a                                             321

SEQ ID NO: 23          moltype = AA  length = 5
FEATURE                Location/Qualifiers
REGION                 1..5
                       note = CDRH1
source                 1..5
                       mol_type = protein
                       organism = synthetic construct
SEQUENCE: 23
DYYMY                                                                5

SEQ ID NO: 24          moltype = AA  length = 17
FEATURE                Location/Qualifiers
REGION                 1..17
                       note = CDRH2
source                 1..17
                       mol_type = protein
                       organism = synthetic construct
SEQUENCE: 24
TINDGGSYTY YPDSVKG                                                  17

SEQ ID NO: 25          moltype = AA  length = 10
FEATURE                Location/Qualifiers
REGION                 1..10
```

```
                        note = CDRH3
source                  1..10
                        mol_type = protein
                        organism = synthetic construct
SEQUENCE: 25
DWGLRPWFVY                                                                10

SEQ ID NO: 26           moltype = AA  length = 11
FEATURE                 Location/Qualifiers
REGION                  1..11
                        note = CDRL1
source                  1..11
                        mol_type = protein
                        organism = synthetic construct
SEQUENCE: 26
KASQDVSTAV A                                                              11

SEQ ID NO: 27           moltype = AA  length = 7
FEATURE                 Location/Qualifiers
REGION                  1..7
                        note = CDRL2
source                  1..7
                        mol_type = protein
                        organism = synthetic construct
SEQUENCE: 27
WASTRHT                                                                   7

SEQ ID NO: 28           moltype = AA  length = 9
FEATURE                 Location/Qualifiers
REGION                  1..9
                        note = CDRL3
source                  1..9
                        mol_type = protein
                        organism = synthetic construct
SEQUENCE: 28
QQHYTTPPT                                                                 9

SEQ ID NO: 29           moltype = AA  length = 119
FEATURE                 Location/Qualifiers
REGION                  1..119
                        note = Heavy Chain Variable Region
source                  1..119
                        mol_type = protein
                        organism = synthetic construct
SEQUENCE: 29
QVQLVESGGG LVKPGGSLKL SCAASGFTFS DYYMYWIRQT PEKRLEWVAT INDGGSYTYY          60
PDSVKGRFTI SRDNAKNNLY LQMSSLKSED TAMYYCARDW GLRPWFVYWG QGTLVTVSA          119

SEQ ID NO: 30           moltype = DNA  length = 357
FEATURE                 Location/Qualifiers
misc_feature            1..357
                        note = Heavy Chain Variable Region
source                  1..357
                        mol_type = other DNA
                        organism = synthetic construct
SEQUENCE: 30
gaagtgcagc tggtggagtc tgggggaggc ttagtgaagc tggaggtc cctgaaactc           60
tcctgtgcag cctctggatt cactttcagt gactattaca tgtattggat cgccagact         120
ccggaaaaga ggctggagtg ggtcgcaacc attaatgatg gtggtagtaa cacctactat        180
ccagacagtg tgaaggggcg attcaccatc tccagagaca atgccaagaa caacctgtac        240
ctgcaaatga gcagtctgaa gtctgaggac acagccatgt attactgtgc aagagactgg        300
ggattacgac cctggtttgt ttactggggc caagggactc tggtcactgt ctctgca          357

SEQ ID NO: 31           moltype = AA  length = 107
FEATURE                 Location/Qualifiers
REGION                  1..107
                        note = Light Chain Variable Region
source                  1..107
                        mol_type = protein
                        organism = synthetic construct
SEQUENCE: 31
DIVMTQSHKF MSTSVGDRVS ITCKASQDVS TAVAWYQQKP GQSPKLLIYW ASTRHTGVPD          60
RFTGSGSGTD YTLTISSVQA EDLALYYCQQ HYTTPPTFGS GTKLEIK                      107

SEQ ID NO: 32           moltype = DNA  length = 321
FEATURE                 Location/Qualifiers
misc_feature            1..321
                        note = Light Chain Variable Region
source                  1..321
```

```
                              mol_type = other DNA
                              organism = synthetic construct
SEQUENCE: 32
gacattgtga tgacccagtc tcacaaattc atgtccacat cagtaggaga cagggtcagc    60
atcacctgca aggccagtca ggatgtgagt actgctgtag cctggtatca acaaaaacca   120
gggcaatctc ctaaactact gatttactgg gcatccaccc ggcacactgg agtccctgat   180
cgcttcacag gcagtggatc tgggacagat tatactctca ccatcagcag tgtgcaggct   240
gaagacctgg cactttatta ctgtcagcaa cattatacca ctcctcccac gttcggctcg   300
gggacaaagt tggaaataaa a                                             321

SEQ ID NO: 33              moltype = AA  length = 5
FEATURE                    Location/Qualifiers
REGION                     1..5
                           note = CDRH1
source                     1..5
                           mol_type = protein
                           organism = synthetic construct
SEQUENCE: 33
GYNMN                                                                 5

SEQ ID NO: 34              moltype = AA  length = 17
FEATURE                    Location/Qualifiers
REGION                     1..17
                           note = CDRH2
source                     1..17
                           mol_type = protein
                           organism = synthetic construct
SEQUENCE: 34
NIDPYYGGTS YNQKFKG                                                   17

SEQ ID NO: 35              moltype = AA  length = 7
FEATURE                    Location/Qualifiers
REGION                     1..7
                           note = CDRH3
source                     1..7
                           mol_type = protein
                           organism = synthetic construct
SEQUENCE: 35
YGNYVDY                                                               7

SEQ ID NO: 36              moltype = AA  length = 11
FEATURE                    Location/Qualifiers
REGION                     1..11
                           note = CDRL1
source                     1..11
                           mol_type = protein
                           organism = synthetic construct
SEQUENCE: 36
KASQDVSTAV A                                                         11

SEQ ID NO: 37              moltype = AA  length = 7
FEATURE                    Location/Qualifiers
REGION                     1..7
                           note = CDRL2
source                     1..7
                           mol_type = protein
                           organism = synthetic construct
SEQUENCE: 37
WASTRHT                                                               7

SEQ ID NO: 38              moltype = AA  length = 9
FEATURE                    Location/Qualifiers
REGION                     1..9
                           note = CDRL3
source                     1..9
                           mol_type = protein
                           organism = synthetic construct
SEQUENCE: 38
QQHYNTPPT                                                             9

SEQ ID NO: 39              moltype = AA  length = 116
FEATURE                    Location/Qualifiers
REGION                     1..116
                           note = Heavy Chain Variable Region
source                     1..116
                           mol_type = protein
                           organism = synthetic construct
SEQUENCE: 39
EVQLQQSGPE LEKPGASVKI SCKASGYSFT GYNMNWVKQS NGKSLEWIGN IDPYYGGTSY    60
```

```
NQKFKGKATL TVDKSSSTAY MQLKSLTSED SAVYYCVRYG NYVDYWGQGT TLTVSS          116

SEQ ID NO: 40              moltype = DNA  length = 342
FEATURE                    Location/Qualifiers
misc_feature               1..342
                           note = Heavy Chain Variable Region
source                     1..342
                           mol_type = other DNA
                           organism = synthetic construct
SEQUENCE: 40
cagctgcagc agtctggacc tgagctggag aagcctggcg cttcagtgaa gatatcctgc      60
aaggcttctg gttactcatt cactggctac aacatgaact gggtgaagca gagcaatgga     120
aagagccttg agtggattgg aaatattgat ccttactatg gtggtactag ctacaaccag     180
aagttcaagg gcaaggccac attgactgta gacaaatcct ccagcacagc ctacatgcag     240
ctcaagagcc tgacatctga ggactctgca gtctattact gtgtaaggta tggtaactac     300
gtggactact ggggccaagg caccactctc acagtctcct ca                        342

SEQ ID NO: 41              moltype = AA  length = 107
FEATURE                    Location/Qualifiers
REGION                     1..107
                           note = Light Chain Variable Region
source                     1..107
                           mol_type = protein
                           organism = synthetic construct
SEQUENCE: 41
DIVMTQSHKF MSTSVGDRVS ITCKASQDVS TAVAWYQQKP GQSPKLLIYW ASTRHTGVPD      60
RFTGSGSGTD YTLTISSVQA EDLALYYCQQ HYNTPPTFGS GTKLEIK                   107

SEQ ID NO: 42              moltype = DNA  length = 321
FEATURE                    Location/Qualifiers
misc_feature               1..321
                           note = Light Chain Variable Region
source                     1..321
                           mol_type = other DNA
                           organism = synthetic construct
SEQUENCE: 42
gacattgtga tgacccagtc ccacaaattc atgtccacat cagtaggaga cagggtcagc      60
atcacctgca aggccagtca ggatgtgagt actgctgtag cctggtatca acaaaaacca     120
gggcaatctc ctaaactact gatttactgg gcatccactc ggcacactgg agtccctgac     180
cgcttcacag gcagtggatc tgggacagat tatactctca ccatcagcag tgtgcaggct     240
gaagacctgg cactttatta ctgtcagcaa cattataaca ctcctcccac gttcggctcg     300
gggacaaagt tggaaataaa a                                               321

SEQ ID NO: 43              moltype = AA  length = 119
FEATURE                    Location/Qualifiers
REGION                     1..119
                           note = VH
source                     1..119
                           mol_type = protein
                           organism = synthetic construct
SEQUENCE: 43
QVQLVESGGG LVKPGGSLRL SCAASGFTFS DYYMYWIRQA PGKGLEWVST ISVGGSFTYY      60
PDSVKGRFTI SRDNAKNSLY LQMNSLRAED TAVYYCARDW GLRPWFVYWG QGTLVTVSS     119

SEQ ID NO: 44              moltype = AA  length = 107
FEATURE                    Location/Qualifiers
REGION                     1..107
                           note = VL
source                     1..107
                           mol_type = protein
                           organism = synthetic construct
SEQUENCE: 44
DIQMTQSPSS LSASVGDRVT ITCKASQDVS TAVAWYQQKP GKAPKLLIYW ASTRHTGVPS      60
RFSGSGSGTD FTLTISSLQP EDFATYYCQQ HYSTPPTFGQ GTKVEIK                   107

SEQ ID NO: 45              moltype = DNA  length = 357
FEATURE                    Location/Qualifiers
misc_feature               1..357
                           note = VH
source                     1..357
                           mol_type = other DNA
                           organism = synthetic construct
SEQUENCE: 45
caggtacagc tcgtggagtc tggtggaggc ttggtgaaac ctggagggtc cctgagactt      60
agctgtgcag cttccggctt cacatttttca gactattata tgtattggat cagacaggct    120
cccgggaagg gcttggagtg ggtttcaacc attagtgttg gcggatcttt acttactac      180
ccagacagtg tgaaggggag attcacaatc tccaggata acgcgaaaaa cagcctgtat      240
ctccaaatga atagcctgag agccgaagat accgccgtgt actactgcgc cagagactgg    300
ggattacggc cctggttcgt gtactgggggc caggggaaccc tggtcaccgt ctcctca     357
```

```
SEQ ID NO: 46           moltype = DNA  length = 321
FEATURE                 Location/Qualifiers
misc_feature            1..321
                        note = VL
source                  1..321
                        mol_type = other DNA
                        organism = synthetic construct
SEQUENCE: 46
gacatccaga tgacacagtc cccaagctcc ctgtctgcat ctgtgggaga ccgggtgacc    60
atcacttgta aggcctcaca ggatgtttct actgctgtcg catggtacca gcaaaagccg   120
ggtaaagctc ccaagctttt gatatactgg gccagcacca ggcacacagg cgtgccatca   180
agattcagtg gtccggatc cggcacggat tttacactca ctattagctc actgcaacct    240
gaagactttg ccacctatta ctgccagcag cattatagca cccctcccac cttcggtcag   300
ggcactaaag tagaaatcaa a                                             321

SEQ ID NO: 47           moltype = AA  length = 119
FEATURE                 Location/Qualifiers
REGION                  1..119
                        note = VH
source                  1..119
                        mol_type = protein
                        organism = synthetic construct
SEQUENCE: 47
QVQLVESGGG LVKPGGSLRL SCAASGFTFS DYYMYWVRQA PGKGLEWVST ISVGGSFTYY    60
PDSVKGRFTI SRDNAKNSLY LQMNSLRAED TAVYYCARDW GLRPWFVYWG QGTLVTVSS    119

SEQ ID NO: 48           moltype = AA  length = 107
FEATURE                 Location/Qualifiers
REGION                  1..107
                        note = VL
source                  1..107
                        mol_type = protein
                        organism = synthetic construct
SEQUENCE: 48
DIQMTQSPSS LSASVGDRVT ITCKASQDVS TAVAWYQQKP GKAPKLLIYW ASTRHTGVPS    60
RFSGSGSGTD FTLTISSLQP EDFATYYCQQ HYSTPPTFGQ GTKVEIK                 107

SEQ ID NO: 49           moltype = DNA  length = 357
FEATURE                 Location/Qualifiers
misc_feature            1..357
                        note = VH
source                  1..357
                        mol_type = other DNA
                        organism = synthetic construct
SEQUENCE: 49
caggtccagc tggtggaatc cggcggaggc ttggtgaagc ctggaggcag cctaagactc    60
tcctgtgcag cctctggctt cacccttctct gactattaca tgtattgggt ccgccaggct   120
ccagggaaag ggctcgagtg ggtttcaaca attagtgtag gtggaagctt cacctactat   180
cctgactccg tgaaaggaag atttacgatc tctaggata atgccaagaa ctcactgtac    240
cttcagatga acagcctgag agcggaggac acagccgtgt actactgcgc tagagattgg   300
ggattaagac cctggtttgt ttattgggc agggaaccc tggtcaccgt ctcctca       357

SEQ ID NO: 50           moltype = DNA  length = 321
FEATURE                 Location/Qualifiers
misc_feature            1..321
                        note = VL
source                  1..321
                        mol_type = other DNA
                        organism = synthetic construct
SEQUENCE: 50
gacatccaga tgacacagtc cccaagctcc ctgtctgcat ctgtgggaga ccgggtgacc    60
atcacttgta aggcctcaca ggatgtttct actgctgtcg catggtacca gcaaaagccg   120
ggtaaagctc ccaagctttt gatatactgg gccagcacca ggcacacagg cgtgccatca   180
agattcagtg gtccggatc cggcacggat tttacactca ctattagctc actgcaacct    240
gaagactttg ccacctatta ctgccagcag cattatagca cccctcccac cttcggtcag   300
ggcactaaag tagaaatcaa a                                             321

SEQ ID NO: 51           moltype = AA  length = 119
FEATURE                 Location/Qualifiers
REGION                  1..119
                        note = VH
source                  1..119
                        mol_type = protein
                        organism = synthetic construct
SEQUENCE: 51
QVQLVESGGG LVKPGGSLRL SCAASGFTFS DYYMYWVRQA PGKGLEWVAT ISVGGSFTYY    60
PDSVKGRFTI SRDNAKNSLY LQMNSLRAED TAVYYCARDW GLRPWFVYWG QGTLVTVSS    119
```

| SEQ ID NO: 52 | moltype = AA length = 107 |
| --- | --- |
| FEATURE | Location/Qualifiers |
| REGION | 1..107 |
| | note = VL |
| source | 1..107 |
| | mol_type = protein |
| | organism = synthetic construct |

SEQUENCE: 52
```
DIQMTQSPSS LSASVGDRVT ITCKASQDVS TAVAWYQQKP GKAPKLLIYW ASTRHTGVPS   60
RFSGSGSGTD FTLTISSLQP EDFATYYCQQ HYSTPPTFGQ GTKVEIK               107
```

| SEQ ID NO: 53 | moltype = DNA length = 357 |
| --- | --- |
| FEATURE | Location/Qualifiers |
| misc_feature | 1..357 |
| | note = VH |
| source | 1..357 |
| | mol_type = other DNA |
| | organism = synthetic construct |

SEQUENCE: 53
```
caggtgcagc tggtcgaatc tggaggaggc ttggtgaaac ctgggggggtc cctgagactc    60
tcttgtgcag cctccggctt tacctttct gactactaca tgtattgggt tcgccaggct   120
cccggtaagg ggttagagtg ggtggctacc attagtgttg gcggttcatt tacttattac   180
ccagatagtg tgaaaggacg gttcaccatc agcaggaca atgcaaagaa ctcactctat   240
ctacaaatga atagcctgag agccgaggat acagcgtgt attactcgc cagagattgg   300
ggacttcgac catggttcgt ctactggggc cagggaaccc tggtcaccgt ctcctca     357
```

| SEQ ID NO: 54 | moltype = DNA length = 321 |
| --- | --- |
| FEATURE | Location/Qualifiers |
| misc_feature | 1..321 |
| | note = VL |
| source | 1..321 |
| | mol_type = other DNA |
| | organism = synthetic construct |

SEQUENCE: 54
```
gacatccaga tgacacagtc cccaagctcc ctgtctgcat ctgtgggaga ccgggtgacc    60
atcacttgta aggcctcaca ggatgttct actgctgtcg catggtacca gcaaaagccg   120
ggtaaagctc ccaagctttt gatatactgg gccagcacca ggcacacagg cgtgccatca   180
agattcagtg gtccggatc cggcacggat tttacactca ctattagctc actgcaacct   240
gaagactttg ccacctatta ctgccagcag cattatagca cccctcccac cttcggtcag   300
ggcactaaag tagaaatcaa a                                              321
```

| SEQ ID NO: 55 | moltype = AA length = 121 |
| --- | --- |
| FEATURE | Location/Qualifiers |
| REGION | 1..121 |
| | note = VH |
| source | 1..121 |
| | mol_type = protein |
| | organism = synthetic construct |

SEQUENCE: 55
```
QVQLVQSGAE VKKPGASVKV SCKASGYTFT SYWMHWVRQA PGQGLEWMGM IDPSDSETRL    60
NQKFKDRVTM TRDTSTSTVY MELSSLRSED TAVYYCARRF YYGSDWYFDV WGQGTLVTVS   120
S                                                                   121
```

| SEQ ID NO: 56 | moltype = AA length = 107 |
| --- | --- |
| FEATURE | Location/Qualifiers |
| REGION | 1..107 |
| | note = VL |
| source | 1..107 |
| | mol_type = protein |
| | organism = synthetic construct |

SEQUENCE: 56
```
DIQLTQSPSF LSASVGDRVT ITCKASQDVG TAVAWYQQKP GKAPKLLIYW ASTRHTGVPS    60
RFSGSGSGTE FTLTISSLQP EDFATYYCQQ YSSYPLTFGQ GTKVEIK                 107
```

| SEQ ID NO: 57 | moltype = DNA length = 363 |
| --- | --- |
| FEATURE | Location/Qualifiers |
| misc_feature | 1..363 |
| | note = VH |
| source | 1..363 |
| | mol_type = other DNA |
| | organism = synthetic construct |

SEQUENCE: 57
```
caggtgcagc tggtgcagag tggagctgag gtaaaaaagc ccggcgccag tgtgaaggtt    60
agttgcaagg cctctggata caccttcaca agctattgga tgcactgggt gcgacaagct   120
cctgggcagg gcttgagtg gatgggaatg atcgacccat ccgattcaga aactaggctc   180
aaccagaaat tcaaagatag agtgactatg accaggaca cctccacgag cacagtctac   240
atggaattgt caagcctgcg ctctgaggac acagccgtgt actattgtgc aagacggttt   300
tactatggta gcgattggta ctttgatgtt tggggccagg gaaccctggt caccgtctcc   360
tca                                                                 363
```

```
SEQ ID NO: 58             moltype = DNA  length = 321
FEATURE                   Location/Qualifiers
misc_feature              1..321
                          note = VL
source                    1..321
                          mol_type = other DNA
                          organism = synthetic construct
SEQUENCE: 58
gacatacagt tgacccagtc tccttccttc ctgtccgcct ccgtgggcga tagagttacc    60
attacttgca aagctagtca ggacgtgggt accgcagtgg cctggtatca gcagaaacca   120
ggtaaagccc ctaagctcct gatctactgg gcatcaacac ggcacacagg ggtcccaagc   180
aggttttctg gcagcggatc aggaaccgaa tttacactga cgatctcgtc tctgcagccc   240
gaggatttcg ctacttacta ctgtcaacaa tatagtagct atccctcac tttcggtcag    300
ggcactaaag tagaaatcaa a                                             321

SEQ ID NO: 59             moltype = AA  length = 121
FEATURE                   Location/Qualifiers
REGION                    1..121
                          note = VH
source                    1..121
                          mol_type = protein
                          organism = synthetic construct
SEQUENCE: 59
QVQLVQSGAE VKKPGASVKV SCKASGYSFT SYWMHWVRQA PGQGLEWIGM IDPSDSETRL    60
NQKFKDRVTM TRDTSTSTVY MELSSLRSED TAVYYCARRF YYGSDWYFDV WGQGTLVTVS   120
S                                                                   121

SEQ ID NO: 60             moltype = AA  length = 107
FEATURE                   Location/Qualifiers
REGION                    1..107
                          note = VL
source                    1..107
                          mol_type = protein
                          organism = synthetic construct
SEQUENCE: 60
DIQLTQSPSF LSASVGDRVT ITCKASQDVG TAVAWYQQKP GKAPKLLIYW ASTRHTGVPS    60
RFSGSGSGTE FTLTISSLQP EDFATYYCQQ YSSYPLTFGQ GTKVEIK                 107

SEQ ID NO: 61             moltype = DNA  length = 363
FEATURE                   Location/Qualifiers
misc_feature              1..363
                          note = VH
source                    1..363
                          mol_type = other DNA
                          organism = synthetic construct
SEQUENCE: 61
caggtgcaac tcgtgcagtc tggagctgaa gtgaagaaac ccggggcctc agtgaaggtg    60
agttgcaaag catctgggta ctcatttacc agctattgga tgcactgggt gcggcaggcc   120
ccaggacaag gcctggagtg gattggcatg atcgacccct ccgatagtga aacgaggctg   180
aaccagaaat ttaaagatcg cgtcaccatg accagggaca agtacttc tacagtctac     240
atggagttga gcagcctgag atcagaggac acagccgttt actactgtgc tagacgattc   300
tattatggca cgactggta tttcgatgta tggggccagg gaaccctggt caccgtctcc   360
tca                                                                 363

SEQ ID NO: 62             moltype = DNA  length = 321
FEATURE                   Location/Qualifiers
misc_feature              1..321
                          note = VL
source                    1..321
                          mol_type = other DNA
                          organism = synthetic construct
SEQUENCE: 62
gacatacagt tgacccagtc tccttccttc ctgtccgcct ccgtgggcga tagagttacc    60
attacttgca aagctagtca ggacgtgggt accgcagtgg cctggtatca gcagaaacca   120
ggtaaagccc ctaagctcct gatctactgg gcatcaacac ggcacacagg ggtcccaagc   180
aggttttctg gcagcggatc aggaaccgaa tttacactga cgatctcgtc tctgcagccc   240
gaggatttcg ctacttacta ctgtcaacaa tatagtagct atccctcac tttcggtcag    300
ggcactaaag tagaaatcaa a                                             321

SEQ ID NO: 63             moltype = AA  length = 121
FEATURE                   Location/Qualifiers
REGION                    1..121
                          note = VH
source                    1..121
                          mol_type = protein
                          organism = synthetic construct
SEQUENCE: 63
QVQLVQSGAE VKKPGASVKV SCKASGYSFT SYWMHWVRQA PGQGLEWIGM IDPSDSETRL    60
```

```
NQKFKDKASM TRDTSTSTVY MELSSLRSED TAVYYCARRF YYGSDWYFDV WGQGTLVTVS   120
S                                                                 121

SEQ ID NO: 64           moltype = AA  length = 107
FEATURE                 Location/Qualifiers
REGION                  1..107
                        note = VL
source                  1..107
                        mol_type = protein
                        organism = synthetic construct
SEQUENCE: 64
DIQLTQSPSF LSASVGDRVT ITCKASQDVG TAVAWYQQKP GKAPKLLIYW ASTRHTGVPS   60
RFSGSGSGTE FTLTISSLQP EDFATYYCQQ YSSYPLTFGQ GTKVEIK                107

SEQ ID NO: 65           moltype = DNA  length = 363
FEATURE                 Location/Qualifiers
misc_feature            1..363
                        note = VH
source                  1..363
                        mol_type = other DNA
                        organism = synthetic construct
SEQUENCE: 65
caggtgcaac tggtgcagtc tgtgctgagg tgaagaaaac caggcgcttc agtcaaggta   60
agctgcaaag caagtggata ctccttcacc tcttattgga tgcactgggt tagacaggcc   120
cctggtcaag gcctcgagtg gattggcatg atcgacccct ctgacagcga aactaggctg   180
aatcagaaat ttaaggacaa ggcctccatg acacgggata catccacaag caccgtttac   240
atggaactga gctcgctgag aagtgaggac actgccgtgt attactgtgc gagacgcttt   300
tattacgggt cagattggta cttcgatgtg tggggccagg gaaccctggt caccgtctcc   360
tca                                                                363

SEQ ID NO: 66           moltype = DNA  length = 321
FEATURE                 Location/Qualifiers
misc_feature            1..321
                        note = VL
source                  1..321
                        mol_type = other DNA
                        organism = synthetic construct
SEQUENCE: 66
gacatacagt tgacccagtc tccttccttc ctgtccgcct ccgtgggcga tagagttacc   60
attacttgca aagctagtca ggacgtgggt accgcagtgg cctggtatca gcagaaacca   120
ggtaaagccc ctaagctcct gatctactgg gcatcaacac ggcacacagg ggtcccaagc   180
aggttttctg gcagcggatc aggaaccgaa tttacactga cgatctcgtc tctgcagccc   240
gaggatttcg ctacttacta ctgtcaacaa tatagtagct atcccctcac tttcggtcag   300
ggcactaaag tagaaatcaa a                                            321

SEQ ID NO: 67           moltype = AA  length = 121
FEATURE                 Location/Qualifiers
REGION                  1..121
                        note = VH
source                  1..121
                        mol_type = protein
                        organism = synthetic construct
SEQUENCE: 67
QVQLVQSGAE VKKPGASVKV SCKASGYSFT SYWMHWVKQA PGQGLEWIGM IDPSDSETRL   60
NQKFKDKASM TRDTSTSTVY MELSSLRSED TAVYYCARRF YYGSDWYFDV WGQGTLVTVS   120
S                                                                 121

SEQ ID NO: 68           moltype = AA  length = 107
FEATURE                 Location/Qualifiers
REGION                  1..107
                        note = VL
source                  1..107
                        mol_type = protein
                        organism = synthetic construct
SEQUENCE: 68
DIQLTQSPSF LSASVGDRVT ITCKASQDVG TAVAWYQQKP GKAPKLLIYW ASTRHTGVPS   60
RFSGSGSGTE FTLTISSLQP EDFATYYCQQ YSSYPLTFGQ GTKVEIK                107

SEQ ID NO: 69           moltype = DNA  length = 363
FEATURE                 Location/Qualifiers
misc_feature            1..363
                        note = VH
source                  1..363
                        mol_type = other DNA
                        organism = synthetic construct
SEQUENCE: 69
caggtgcagc tggtgcagtc tggggctgag gtgaaaaagc caggcgcttc cgtcaaagtt   60
tcctgcaagg catctggtta ctcttttaca agctattgga tgcactgggt gaagcaggcc   120
cccggacaag ggctcgagtg gattggcatg atcgatcctc cgatagtga aacacgcttg   180
```

```
aatcagaaat tcaaggacaa ggccagtatg accagggata ctagcacaag cactgtatat    240
atggagctta gctcactgag atcagaagac acggccgtgt actactgtgc gagacgtttt    300
tactatggct ccgactggta tttcgacgtc tggggccagg gaaccctggt caccgtctcc    360
tca                                                                  363

SEQ ID NO: 70          moltype = DNA   length = 321
FEATURE                Location/Qualifiers
misc_feature           1..321
                       note = VL
source                 1..321
                       mol_type = other DNA
                       organism = synthetic construct
SEQUENCE: 70
gacatacagt tgacccagtc tccttccttc ctgtccgcct ccgtgggcga tagagttacc     60
attacttgca aagctagtca ggacgtgggt accgcagtgg cctggtatca gcagaaacca    120
ggtaaagccc ctaagctcct gatctactgg gcatcaacac ggcacacagg gtcccaagc     180
aggttttctg gcagcggatc aggaaccgaa tttacactga cgatctcgtc tctgcagccc    240
gaggatttcg ctacttacta ctgtcaacaa tatagtagct atcccctcac tttcggtcag    300
ggcactaaag tagaaatcaa a                                              321

SEQ ID NO: 71          moltype = AA    length = 121
FEATURE                Location/Qualifiers
REGION                 1..121
                       note = VH
source                 1..121
                       mol_type = protein
                       organism = synthetic construct
SEQUENCE: 71
QVQLVQSGAE VKKPGASVKV SCKASGYSFT SYWMHWVKQA PGQGLEWIGM IDPSDSETRL     60
NQKFKDKASL TVDTSTSTVY MELSSLRSED TAVYYCARRF YYGSDWYFDV WGQGTLVTVS    120
S                                                                    121

SEQ ID NO: 72          moltype = AA    length = 107
FEATURE                Location/Qualifiers
REGION                 1..107
                       note = VL
source                 1..107
                       mol_type = protein
                       organism = synthetic construct
SEQUENCE: 72
DIQLTQSPSF LSASVGDRVT ITCKASQDVG TAVAWYQQKP GKAPKLLIYW ASTRHTGVPS     60
RFSGSGSGTE FTLTISSLQP EDFATYYCQQ YSSYPLTFGQ GTKVEIK                  107

SEQ ID NO: 73          moltype = DNA   length = 363
FEATURE                Location/Qualifiers
misc_feature           1..363
                       note = VH
source                 1..363
                       mol_type = other DNA
                       organism = synthetic construct
SEQUENCE: 73
caggtgcagc tggtgcagtc tggcgctgag gtgaagaaac ctggggcctc agtgaaggtt     60
tcctgtaaag caagtggata ctctttcacc agctactgga tgcactgggt gaaacaggcc    120
cccggccaag gcttgagtg gattggtatg atcgatccat ccgacagcga aactaggctc    180
aaccagaagt tcaaggataa agcgtccttg acagtagaca catccacgag cacagtttat    240
atggagctgt ctagtctgcg gtctgaagac acggccgtgt attattgcgc tagacgcttt    300
tattacggct cggactggta ctttgacgtc tggggccagg gaaccctggt caccgtctcc    360
tca                                                                  363

SEQ ID NO: 74          moltype = DNA   length = 321
FEATURE                Location/Qualifiers
misc_feature           1..321
                       note = VL
source                 1..321
                       mol_type = other DNA
                       organism = synthetic construct
SEQUENCE: 74
gacatacagt tgacccagtc tccttccttc ctgtccgcct ccgtgggcga tagagttacc     60
attacttgca aagctagtca ggacgtgggt accgcagtgg cctggtatca gcagaaacca    120
ggtaaagccc ctaagctcct gatctactgg gcatcaacac ggcacacagg gtcccaagc     180
aggttttctg gcagcggatc aggaaccgaa tttacactga cgatctcgtc tctgcagccc    240
gaggatttcg ctacttacta ctgtcaacaa tatagtagct atcccctcac tttcggtcag    300
ggcactaaag tagaaatcaa a                                              321

SEQ ID NO: 75          moltype = AA    length = 121
FEATURE                Location/Qualifiers
REGION                 1..121
                       note = VH
source                 1..121
```

```
                           mol_type = protein
                           organism = synthetic construct
SEQUENCE: 75
QVQLVQSGAE VKKPGASVKV SCKASGYTFT SYWMHWVRQA PGQGLEWMGM IDPSDSETRL    60
NQKFKDRVTM TRDTSTSTVY MELSSLRSED TAVYYCARRF YYGSDWYFDV WGQGTLVTVS   120
S                                                                  121

SEQ ID NO: 76              moltype = AA  length = 107
FEATURE                    Location/Qualifiers
REGION                     1..107
                           note = VL
source                     1..107
                           mol_type = protein
                           organism = synthetic construct
SEQUENCE: 76
DIQLTQSPSF LSASVGDRVS ITCKASQDVG TAVAWYQQKP GKAPKLLIYW ASTRHTGVPD    60
RFSGSGSGTE FTLTISSLQP EDFATYYCQQ YSSYPLTFGQ GTKVEIK                 107

SEQ ID NO: 77              moltype = DNA  length = 363
FEATURE                    Location/Qualifiers
misc_feature               1..363
                           note = VH
source                     1..363
                           mol_type = other DNA
                           organism = synthetic construct
SEQUENCE: 77
caggtgcagc tggtgcagag tggagctgag gtaaaaaagc ccggcgccag tgtgaaggtt    60
agttgcaagg cctctggata caccttcaca agctattgga tgcactgggt gcgacaagct   120
cctgggcagg ggcttgagtg gatgggaatg atcgacccat ccgattcaga aactaggctc   180
aaccagaaat tcaaagatag agtgactatg accagggaca cctccacgag cacagtctac   240
atggaattgt caagcctgcg ctctgaggac acagccgtgt actattgtgc aagacggttt   300
tactatggta gcgattggta ctttgatgtt tggggccagg gaaccctggt caccgtctcc   360
tca                                                                363

SEQ ID NO: 78              moltype = DNA  length = 321
FEATURE                    Location/Qualifiers
misc_feature               1..321
                           note = VL
source                     1..321
                           mol_type = other DNA
                           organism = synthetic construct
SEQUENCE: 78
gatattcaac tcacccagag tccatccttc ctgtctgcct cagtgggcga cagagtgtca    60
atcacatgca aggcaagcca ggatgttggc actgctgtgg cttggtatca gcaaaaacca   120
ggtaaggccc ccaaactgct tatttactgg gcatcaaccc ggcacacggg tgtccccgac   180
aggttcagcg gcagtggatc tgggacagag tttaccctga ctatcagctc cctgcagcct   240
gaaagctttg ccacttatta ctgtcagcag tactctagct atcctctcac cttcggtcag   300
ggcactaaag tagaaatcaa a                                            321

SEQ ID NO: 79              moltype = AA  length = 121
FEATURE                    Location/Qualifiers
REGION                     1..121
                           note = VH
source                     1..121
                           mol_type = protein
                           organism = synthetic construct
SEQUENCE: 79
QVQLVQSGAE VKKPGASVKV SCKASGYSFT SYWMHWVRQA PGQGLEWIGM IDPSDSETRL    60
NQKFKDRVTM TRDTSTSTVY MELSSLRSED TAVYYCARRF YYGSDWYFDV WGQGTLVTVS   120
S                                                                  121

SEQ ID NO: 80              moltype = AA  length = 107
FEATURE                    Location/Qualifiers
REGION                     1..107
                           note = VL
source                     1..107
                           mol_type = protein
                           organism = synthetic construct
SEQUENCE: 80
DIQLTQSPSF LSASVGDRVS ITCKASQDVG TAVAWYQQKP GKAPKLLIYW ASTRHTGVPD    60
RFSGSGSGTE FTLTISSLQP EDFATYYCQQ YSSYPLTFGQ GTKVEIK                 107

SEQ ID NO: 81              moltype = DNA  length = 363
FEATURE                    Location/Qualifiers
misc_feature               1..363
                           note = VH
source                     1..363
                           mol_type = other DNA
                           organism = synthetic construct
```

```
SEQUENCE: 81
caggtgcaac tcgtgcagtc tggagctgaa gtgaagaaac cggggcctc  agtgaaggtg    60
agttgcaaag catctgggta ctcatttacc agctattgga tgcactgggt gcggcaggcc   120
ccaggacaag gcctggagtg gattggcatg atcgacccct tccgatagtga acgaggctg   180
aaccagaagt ttaaagatcg cgtcaccatg accagggaca caagcacttc tacagtctac   240
atggagttga gcagcctgag atcagaggac acagccgttt actactgtgc tagacgattc   300
tattatggca cgactggta  tttcgatgta tggggccagg gaaccctggt caccgtctcc   360
tca                                                                363

SEQ ID NO: 82            moltype = DNA length = 321
FEATURE                  Location/Qualifiers
misc_feature             1..321
                         note = VL
source                   1..321
                         mol_type = other DNA
                         organism = synthetic construct
SEQUENCE: 82
gatattcaac tcacccagag tccatccttc ctgtctgcct cagtgggcga cagagtgtca    60
atcacatgca aggcaagcca ggatgttggc actgctgtgg cttggtatca gcaaaaacca   120
ggtaaggccc ccaaactgct tatttactgg gcatcaaccc ggcacacggg tgtccccgac   180
aggttcagcg gcagtggatc tgggacagag tttaccctga ctatcagctc cctgcagcct   240
gaagactttg ccacttatta ctgtcagcag tactctagct atcctctcac cttcggtcag   300
ggcactaaag tagaaatcaa a                                             321

SEQ ID NO: 83            moltype = AA length = 121
FEATURE                  Location/Qualifiers
REGION                   1..121
                         note = VH
source                   1..121
                         mol_type = protein
                         organism = synthetic construct
SEQUENCE: 83
QVQLVQSGAE VKKPGASVKV SCKASGYSFT SYWMHWVRQA PGQGLEWIGM IDPSDSETRL    60
NQKFKDKASM TRDTSTSTVY MELSSLRSED TAVYYCARRF YYGSDWYFDV WGQGTLVTVS   120
S                                                                  121

SEQ ID NO: 84            moltype = AA length = 107
FEATURE                  Location/Qualifiers
REGION                   1..107
                         note = VL
source                   1..107
                         mol_type = protein
                         organism = synthetic construct
SEQUENCE: 84
DIQLTQSPSF LSASVGDRVS ITCKASQDVG TAVAWYQQKP GKAPKLLIYW ASTRHTGVPD    60
RFSGSGSGTE FTLTISSLQP EDFATYYCQQ YSSYPLTFGQ GTKVEIK                 107

SEQ ID NO: 85            moltype = DNA length = 363
FEATURE                  Location/Qualifiers
misc_feature             1..363
                         note = VH
source                   1..363
                         mol_type = other DNA
                         organism = synthetic construct
SEQUENCE: 85
caggtgcaac tggtgcagtc tggtgctgag gtgaagaaac caggcgcttc agtcaaggta    60
agctgcaaag caagtggata ctccttcacc tcttattgga tgcactgggt tagacaggcc   120
cctggtcaag gcctcgagtg gattggcatg atcgacccct ctgacagcga aactaggctg   180
aatcagaaat ttaaggacaa ggcctccatg acacgggata tccacaagac cgtttac     240
atggaactga gctcgctgag aagtgaggac actgccgtgt attactgc  gagacgcttt   300
tattacgggt cagattggta cttcgatgtg tggggccagg gaaccctggt caccgtctcc   360
tca                                                                363

SEQ ID NO: 86            moltype = DNA length = 321
FEATURE                  Location/Qualifiers
misc_feature             1..321
                         note = VL
source                   1..321
                         mol_type = other DNA
                         organism = synthetic construct
SEQUENCE: 86
gatattcaac tcacccagag tccatccttc ctgtctgcct cagtgggcga cagagtgtca    60
atcacatgca aggcaagcca ggatgttggc actgctgtgg cttggtatca gcaaaaacca   120
ggtaaggccc ccaaactgct tatttactgg gcatcaaccc ggcacacggg tgtccccgac   180
aggttcagcg gcagtggatc tgggacagag tttaccctga ctatcagctc cctgcagcct   240
gaagactttg ccacttatta ctgtcagcag tactctagct atcctctcac cttcggtcag   300
ggcactaaag tagaaatcaa a                                             321

SEQ ID NO: 87            moltype = AA length = 121
```

```
FEATURE                 Location/Qualifiers
REGION                  1..121
                        note = VH
source                  1..121
                        mol_type = protein
                        organism = synthetic construct
SEQUENCE: 87
QVQLVQSGAE VKKPGASVKV SCKASGYSFT SYWMHWVKQA PGQGLEWIGM IDPSDSETRL    60
NQKFKDKASM TRDTSTSTVY MELSSLRSED TAVYYCARRF YYGSDWYFDV WGQGTLVTVS   120
S                                                                  121

SEQ ID NO: 88           moltype = AA   length = 107
FEATURE                 Location/Qualifiers
REGION                  1..107
                        note = VL
source                  1..107
                        mol_type = protein
                        organism = synthetic construct
SEQUENCE: 88
DIQLTQSPSF LSASVGDRVS ITCKASQDVG TAVAWYQQKP GKAPKLLIYW ASTRHTGVPD    60
RFSGSGSGTE FTLTISSLQP EDFATYYCQQ YSSYPLTFGQ GTKVEIK                 107

SEQ ID NO: 89           moltype = DNA   length = 363
FEATURE                 Location/Qualifiers
misc_feature            1..363
                        note = VH
source                  1..363
                        mol_type = other DNA
                        organism = synthetic construct
SEQUENCE: 89
caggtgcagc tggtgcagtc tggggctgag gtgaaaaagc caggcgcttc cgtcaaagtt    60
tcctgcaagg catctggtta ctcttttaca agctattgga tgcactgggt gaagcaggcc   120
cccgacaag ggctcgagtg gattggcatg atcgatcctt ccgatagtga aacacgcttg    180
aatcagaaat tcaaggacaa ggccagtatg accaggtata ctagcacaag cactgtatat   240
atggagctta gctcactgag atcagaagac acggccgtgt actactgtgc gagacggttt   300
tactatggct ccgactggta tttcgacgtc tggggccagg gaacccttggt caccgtctcc   360
tca                                                                363

SEQ ID NO: 90           moltype = DNA   length = 321
FEATURE                 Location/Qualifiers
misc_feature            1..321
                        note = VL
source                  1..321
                        mol_type = other DNA
                        organism = synthetic construct
SEQUENCE: 90
gatattcaac tcacccagag tccatccttc ctgtctgcct cagtgggcga cagagtgtca    60
atcacatgca aggcaagcca ggatgttggc actgctgtgg cttggtatca gcaaaaacca   120
ggtaaggccc ccaaactgct tatttactgg gcatcaaccc ggcacacggg tgtccccgac   180
aggttcagcg gcagtggatc tgggacagag tttaccctga ctatcagctc cctgcagcct   240
gaaagacttt gccacttatta ctgtcagcag tactctagct atcctctcac cttcggtcag   300
ggcactaaag tagaaatcaa a                                            321

SEQ ID NO: 91           moltype = AA   length = 121
FEATURE                 Location/Qualifiers
REGION                  1..121
                        note = VH
source                  1..121
                        mol_type = protein
                        organism = synthetic construct
SEQUENCE: 91
QVQLVQSGAE VKKPGASVKV SCKASGYSFT SYWMHWVKQA PGQGLEWIGM IDPSDSETRL    60
NQKFKDKASL TVDTSTSTVY MELSSLRSED TAVYYCARRF YYGSDWYFDV WGQGTLVTVS   120
S                                                                  121

SEQ ID NO: 92           moltype = AA   length = 107
FEATURE                 Location/Qualifiers
REGION                  1..107
                        note = VL
source                  1..107
                        mol_type = protein
                        organism = synthetic construct
SEQUENCE: 92
DIQLTQSPSF LSASVGDRVS ITCKASQDVG TAVAWYQQKP GKAPKLLIYW ASTRHTGVPD    60
RFSGSGSGTE FTLTISSLQP EDFATYYCQQ YSSYPLTFGQ GTKVEIK                 107

SEQ ID NO: 93           moltype = DNA   length = 363
FEATURE                 Location/Qualifiers
misc_feature            1..363
```

```
                           note = VH
source                     1..363
                           mol_type = other DNA
                           organism = synthetic construct
SEQUENCE: 93
caggtgcagc tggtgcagtc tggcgctgag gtgaagaaac ctggggcctc agtgaaggtt    60
tcctgtaaag caagtggata ctctttcacc agctactgga tgcactgggt gaaacaggcc   120
cccgccaag ggcttgagtg gattggtatg atcgatccat ccgacagcga aactaggctc    180
aaccagaagt tcaaggataa agcgtccttg acagtagata catccacgag cacagtttat   240
atggctgtg ctagtctgcg gtctgaagac accgccgtgt attattgcgc tagacgcttt    300
tattacggct cggactggta ctttgacgtc tggggccagg gaaccctggt caccgtctcc   360
tca                                                                 363

SEQ ID NO: 94              moltype = DNA   length = 321
FEATURE                    Location/Qualifiers
misc_feature               1..321
                           note = VL
source                     1..321
                           mol_type = other DNA
                           organism = synthetic construct
SEQUENCE: 94
gatattcaac tcacccagag tccatccttc ctgtctgcct cagtgggcga cagagtgtca    60
atcacatgca aggcaagcca ggatgttggc actgctgtgg cttggtatca gcaaaaacca   120
ggtaaggccc ccaaactgct tatttactgg gcatcaaccc ggcacacggg tgtccccgac   180
aggttcagcg gcagtggatc tgggacagag tttaccctga ctatcagctc cctgcagcct   240
gaagactttg ccacttatta ctgtcagcag tactctagct atcctctcac cttcggtcag   300
ggcactaaag tagaaatcaa a                                             321

SEQ ID NO: 95              moltype = AA   length = 121
FEATURE                    Location/Qualifiers
REGION                     1..121
                           note = VH
source                     1..121
                           mol_type = protein
                           organism = synthetic construct
SEQUENCE: 95
QVQLVQSGAE VKKPGASVKV SCKASGYTFT SYWMHWVRQA PGQGLEWMGM IDPSDSETRL    60
NQKFKDRVTM TRDTSTSTVY MELSSLRSED TAVYYCARRF YYGSDWYFDV WGQGTLVTVS   120
S                                                                   121

SEQ ID NO: 96              moltype = AA   length = 107
FEATURE                    Location/Qualifiers
REGION                     1..107
                           note = VL
source                     1..107
                           mol_type = protein
                           organism = synthetic construct
SEQUENCE: 96
DIQLTQSPSF LSASVGDRVS ITCKASQDVG TAVAWYQQKP GKAPKLLIYW ASTRHTGVPD    60
RFSGSGSGTE FTLTISSLQP EDFADYFCQQ YSSYPLTFGQ GTKVEIK                 107

SEQ ID NO: 97              moltype = DNA   length = 363
FEATURE                    Location/Qualifiers
misc_feature               1..363
                           note = VH
source                     1..363
                           mol_type = other DNA
                           organism = synthetic construct
SEQUENCE: 97
caggtgcagc tggtgcagag tggagctgag gtaaaaaagc ccggcgccag tgtgaaggtt    60
agttgcaagg cctctggata caccttcaca agctattgga tgcactgggt gcgacaagct   120
cctgggcagg ggcttgagtg gatgggaatg atcgacccat ccgattcaga aactaggctc   180
aaccagaaat tcaaagatag agtgactatg accaggaca cctccacgag cacagtctac    240
atggaattgt caagcctgcg ctctgaggac acagccgtgt actattgtgc aagacggttt    300
tactatggta gcgattggta ctttgatgtt tggggccagg gaaccctggt caccgtctcc   360
tca                                                                 363

SEQ ID NO: 98              moltype = DNA   length = 321
FEATURE                    Location/Qualifiers
misc_feature               1..321
                           note = VL
source                     1..321
                           mol_type = other DNA
                           organism = synthetic construct
SEQUENCE: 98
gacatccagt tgacccaatc accatccttt ctgtctgcct ctgtgggaga tagagtctcc    60
attacttgca aggccagtca ggatgtgggg accgctgttg cctggtacca gcaaaaaccc   120
ggaaaggcac ctaaactcct tatctactgg gcatccaccc ggcacacagg agtgccagac   180
aggtttagcg ggtcaggctc tgggacagag ttcactctga caatttctag cctgcagcct   240
```

```
gaagacttcg ctgattattt ctgtcagcag tatagcagtt accccctcac gttcggtcag    300
ggcactaaag tagaaatcaa a                                              321

SEQ ID NO: 99            moltype = AA  length = 121
FEATURE                  Location/Qualifiers
REGION                   1..121
                         note = VH
source                   1..121
                         mol_type = protein
                         organism = synthetic construct
SEQUENCE: 99
QVQLVQSGAE VKKPGASVKV SCKASGYSFT SYWMHWVRQA PGQGLEWIGM IDPSDSETRL    60
NQKFKDRVTM TRDTSTSTVY MELSSLRSED TAVYYCARRF YYGSDWYFDV WGQGTLVTVS    120
S                                                                    121

SEQ ID NO: 100           moltype = AA  length = 107
FEATURE                  Location/Qualifiers
REGION                   1..107
                         note = VL
source                   1..107
                         mol_type = protein
                         organism = synthetic construct
SEQUENCE: 100
DIQLTQSPSF LSASVGDRVS ITCKASQDVG TAVAWYQQKP GKAPKLLIYW ASTRHTGVPD    60
RFSGSGSGTE FTLTISSLQP EDFADYFCQQ YSSYPLTFGQ GTKVEIK                  107

SEQ ID NO: 101           moltype = DNA  length = 363
FEATURE                  Location/Qualifiers
misc_feature             1..363
                         note = VH
source                   1..363
                         mol_type = other DNA
                         organism = synthetic construct
SEQUENCE: 101
caggtgcaac tcgtgcagtc tggagctgaa gtgaagaaac ccggggcctc agtgaaggtg    60
agttgcaaag catctgggta ctcatttacc agctattgga tgcactgggt gcggcaggcc    120
ccaggacaag gcctggagtg gattggcatg atcgaccctt ccgatagtga aacgaggctg    180
aaccagaagt ttaaagatcg cgtcaccatg accagggaca caagtacttc tacagtctac    240
atggagttga gcagcctgag atcagaggac acagccgttt actactgtgc tagacgattc    300
tattatggca gcgactggta tttcgatgta tggggccagg gaaccctggt caccgtctcc    360
tca                                                                  363

SEQ ID NO: 102           moltype = DNA  length = 321
FEATURE                  Location/Qualifiers
misc_feature             1..321
                         note = VL
source                   1..321
                         mol_type = other DNA
                         organism = synthetic construct
SEQUENCE: 102
gacatccagt tgacccaatc accatccttt ctgtctgcct ctgtgggaga tagagtctcc    60
attacttgca aggccagtca ggatgtgggg accgctgttg cctggtacca gcaaaaaccc    120
ggaaaggcac ctaaactcct tatctactgg gcatccaccc ggcacacagg agtgccagac    180
aggtttagcg gtcaggctc tggtacagag ttcactctga caatttctag cctgcagcct    240
gaagacttcg ctgattattt ctgtcagcag tatagcagtt accccctcac gttcggtcag    300
ggcactaaag tagaaatcaa a                                              321

SEQ ID NO: 103           moltype = AA  length = 121
FEATURE                  Location/Qualifiers
REGION                   1..121
                         note = VH
source                   1..121
                         mol_type = protein
                         organism = synthetic construct
SEQUENCE: 103
QVQLVQSGAE VKKPGASVKV SCKASGYSFT SYWMHWVRQA PGQGLEWIGM IDPSDSETRL    60
NQKFKDKASM TRDTSTSTVY MELSSLRSED TAVYYCARRF YYGSDWYFDV WGQGTLVTVS    120
S                                                                    121

SEQ ID NO: 104           moltype = AA  length = 107
FEATURE                  Location/Qualifiers
REGION                   1..107
                         note = VL
source                   1..107
                         mol_type = protein
                         organism = synthetic construct
SEQUENCE: 104
DIQLTQSPSF LSASVGDRVS ITCKASQDVG TAVAWYQQKP GKAPKLLIYW ASTRHTGVPD    60
RFSGSGSGTE FTLTISSLQP EDFADYFCQQ YSSYPLTFGQ GTKVEIK                  107
```

```
SEQ ID NO: 105          moltype = DNA  length = 363
FEATURE                 Location/Qualifiers
misc_feature            1..363
                        note = VH
source                  1..363
                        mol_type = other DNA
                        organism = synthetic construct
SEQUENCE: 105
caggtgcaac tggtgcagtc tggtgctgag gtgaagaaac caggcgcttc agtcaaggta    60
agctgcaaag caagtggata ctccttcacc tcttattgga tgcactgggt tagacaggcc   120
cctggtcaag gcctcgagtg gattggcatg atcgacccct ctgacagcga aactaggctg   180
aatcagaaat ttaaggacaa ggcctccatg acacgggata catccacaag caccgtttac   240
atggaactga gctcgctgag aagtgaggac actgccgtgt attactgcgc gagacgcttt   300
tattacgggt cagattggta cttcgatgtg tggggccagg aacccctggt caccgtctcc   360
tca                                                                 363

SEQ ID NO: 106          moltype = DNA  length = 321
FEATURE                 Location/Qualifiers
misc_feature            1..321
                        note = VL
source                  1..321
                        mol_type = other DNA
                        organism = synthetic construct
SEQUENCE: 106
gacatccagt tgacccaatc accatccttt ctgtctgcct ctgtgggaga tagagtctcc    60
attacttgca aggccagtca ggatgtgggg accgctgttg cctggtacca gcaaaaaccc   120
ggaaaggcac ctaaactcct tatctactgg gcatccaccc ggcacacagg agtgccagac   180
aggtttagcg ggtcaggctc tggtacagag ttcactctga caatttctag cctgcagcct   240
gaagacttcg ctgattattt ctgtcagcag tatagcagtt accccctcac gttcggtcag   300
ggcactaaag tagaaatcaa a                                             321

SEQ ID NO: 107          moltype = AA  length = 121
FEATURE                 Location/Qualifiers
REGION                  1..121
                        note = VH
source                  1..121
                        mol_type = protein
                        organism = synthetic construct
SEQUENCE: 107
QVQLVQSGAE VKKPGASVKV SCKASGYSFT SYWMHWVKQA PGQGLEWIGM IDPSDSETRL    60
NQKFKDKASM TRDTSTSTVY MELSSLRSED TAVYYCARRF YYGSDWYFDV WGQGTLVTVS   120
S                                                                   121

SEQ ID NO: 108          moltype = AA  length = 107
FEATURE                 Location/Qualifiers
REGION                  1..107
                        note = VL
source                  1..107
                        mol_type = protein
                        organism = synthetic construct
SEQUENCE: 108
DIQLTQSPSF LSASVGDRVS ITCKASQDVG TAVAWYQQKP GKAPKLLIYW ASTRHTGVPD    60
RFSGSGSGTE FTLTISSLQP EDFADYFCQQ YSSYPLTFGQ GTKVEIK                 107

SEQ ID NO: 109          moltype = DNA  length = 363
FEATURE                 Location/Qualifiers
misc_feature            1..363
                        note = VH
source                  1..363
                        mol_type = other DNA
                        organism = synthetic construct
SEQUENCE: 109
caggtgcagc tggtgcagtc tggggctgag gtgaagaaag caggcgcttc cgtcaaagtt    60
tcctgcaagg catctggtta ctcttttaca agctattgga tgcactgggt gaagcaggcc   120
cccgacaagg gctcgagtg gattggcatg atcgatcctt ccgatagtga aacacgcttg   180
aatcagaaat tcaaggacaa ggccagtatg accagggata ctagcacaag cactgtatat   240
atggagctta gctcactgag atcagaagac acggccgtgt actactgtgc gagacggttt   300
tactatggct ccgactggta tttcgacgtc tggggccagg aacccctggt caccgtctcc   360
tca                                                                 363

SEQ ID NO: 110          moltype = DNA  length = 321
FEATURE                 Location/Qualifiers
misc_feature            1..321
                        note = VL
source                  1..321
                        mol_type = other DNA
                        organism = synthetic construct
SEQUENCE: 110
```

```
gacatccagt tgacccaatc accatccttt ctgtctgcct ctgtgggaga tagagtctcc    60
attacttgca aggccagtca ggatgtgggg accgctgttg cctggtacca gcaaaaaccc   120
ggaaaggcac ctaaactcct tatctactgg gcatccaccc ggcacacagg agtgccagac   180
aggtttagcg ggtcaggctc tggtacagag ttcactctga caatttctag cctgcagcct   240
gaagacttcg ctgattattt ctgtcagcag tatagcagtt accccctcac gttcggtcag   300
ggcactaaag tagaaatcaa a                                              321

SEQ ID NO: 111           moltype = AA   length = 121
FEATURE                  Location/Qualifiers
REGION                   1..121
                         note = VH
source                   1..121
                         mol_type = protein
                         organism = synthetic construct
SEQUENCE: 111
QVQLVQSGAE VKKPGASVKV SCKASGYSFT SYWMHWVKQA PGQGLEWIGM IDPSDSETRL    60
NQKFKDKASL TVDTSTSTVY MELSSLRSED TAVYYCARRF YYGSDWYFDV WGQGTLVTVS   120
S                                                                   121

SEQ ID NO: 112           moltype = AA   length = 107
FEATURE                  Location/Qualifiers
REGION                   1..107
                         note = VL
source                   1..107
                         mol_type = protein
                         organism = synthetic construct
SEQUENCE: 112
DIQLTQSPSF LSASVGDRVS ITCKASQDVG TAVAWYQQKP GKAPKLLIYW ASTRHTGVPD    60
RFSGSGSGTE FTLTISSLQP EDFADYFCQQ YSSYPLTFGQ GTKVEIK                 107

SEQ ID NO: 113           moltype = DNA   length = 363
FEATURE                  Location/Qualifiers
misc_feature             1..363
                         note = VH
source                   1..363
                         mol_type = other DNA
                         organism = synthetic construct
SEQUENCE: 113
caggtgcagc tggtgcagtc tggcgctgag gtgaagaaac ctggggcctc agtgaaggtt    60
tcctgtaaag caagtggata ctcttttcacc agctactgga tgcactgggt gaaacaggcc   120
cccggccaag ggcttgagtg gattggtatg atcgatccat ccgacagcga aactaggctc   180
aaccagaagt tcaaggataa agcgtccttg acagtagata catccacgag cacagtttat   240
atggagctgt ctagtctgcg gtctgaagac accgccgtgt attattgcgc tagacgtttt   300
tattacggct cggactggta ctttgacgtc tggggccagg gaaccctggt caccgtctcc   360
tca                                                                 363

SEQ ID NO: 114           moltype = DNA   length = 321
FEATURE                  Location/Qualifiers
misc_feature             1..321
                         note = VL
source                   1..321
                         mol_type = other DNA
                         organism = synthetic construct
SEQUENCE: 114
gacatccagt tgacccaatc accatccttt ctgtctgcct ctgtgggaga tagagtctcc    60
attacttgca aggccagtca ggatgtgggg accgctgttg cctggtacca gcaaaaaccc   120
ggaaaggcac ctaaactcct tatctactgg gcatccaccc ggcacacagg agtgccagac   180
aggtttagcg ggtcaggctc tggtacagag ttcactctga caatttctag cctgcagcct   240
gaagacttcg ctgattattt ctgtcagcag tatagcagtt accccctcac gttcggtcag   300
ggcactaaag tagaaatcaa a                                              321

SEQ ID NO: 115           moltype = AA   length = 18
FEATURE                  Location/Qualifiers
REGION                   1..18
                         note = epitope
source                   1..18
                         mol_type = protein
                         organism = synthetic construct
SEQUENCE: 115
QRTWKEYKVG FGNPSGEY                                                  18

SEQ ID NO: 116           moltype = AA   length = 11
FEATURE                  Location/Qualifiers
REGION                   1..11
                         note = epitope
source                   1..11
                         mol_type = protein
                         organism = synthetic construct
SEQUENCE: 116
```

```
KSGHTTNGIY T                                                               11

SEQ ID NO: 117      moltype = AA  length = 7
FEATURE             Location/Qualifiers
REGION              1..7
                    note = epitope
source              1..7
                    mol_type = protein
                    organism = synthetic construct
SEQUENCE: 117
EAGGGGW                                                                    7
```

The invention claimed is:

1. An antibody or antigen-binding fragment thereof that specifically binds human Angiopoietin-2 and induces Tie2 activation, wherein the antibody or antigen-binding fragment thereof comprises:
   (a) the complementarity determining regions (CDRs) of a heavy chain variable region comprising HCDR1 amino acid sequence of SEQ ID NO: 3, the HCDR2 amino acid sequence of SEQ ID NO: 4, and the HCDR3 amino acid sequence of SEQ ID NO: 5; and
   (b) the CDRs of a light chain variable region comprising the LCDR1 amino acid sequence of SEQ ID NO: 6, the LCDR2 amino acid sequence of SEQ ID NO: 7, and the LCDR3 amino acid sequence of SEQ ID NO: 8.

2. The antibody or antigen-binding fragment thereof of claim 1, wherein the antibody or antigen-binding fragment thereof binds to amino acids of SEQ ID NO: 116 and/or amino acids of SEQ ID NO: 117.

3. The antibody or antigen-binding fragment thereof of claim 1, wherein the antigen-binding fragment is scFv or Fab.

4. The antibody or antigen-binding fragment thereof of claim 1, wherein the antibody is humanized.

5. The antibody or antigen-binding fragment thereof of claim 1, comprising:
   a heavy chain variable region selected from SEQ ID NOs: 9, 43, 47, or 51; and
   a light chain variable region selected from SEQ ID NOs: 11, 44, 48, or 52.

6. A pharmaceutical composition comprising the antibody or antigen-binding fragment thereof of claim 1 and a pharmaceutically acceptable carrier.

7. The pharmaceutical composition of claim 6, further comprising a small molecule inhibitor, wherein the small molecule inhibitor is a chemotherapy agent.

8. The pharmaceutical composition of claim 6, further comprising a vascular endothelial growth factor (VEGF) antagonist.

9. The pharmaceutical composition of claim 8, wherein the VEGF antagonist is an anti-VEGF antibody, a VEGF inhibiting fusion protein, or a small molecule kinase inhibitor.

10. A composition comprising an antibody of claim 1, wherein the antibody is monoclonal.

11. A monoclonal antibody or antigen-binding fragment thereof that specifically binds human Angiopoietin-2 and induces Tie2 activation, wherein the antibody or antigen-binding fragment thereof comprises the complementary determining regions (CDRs) of an antibody produced from a cell line deposited with accession number KCLRF-BP-00418.

* * * * *